(12) United States Patent
Beliveau et al.

(10) Patent No.: US 8,853,353 B2
(45) Date of Patent: Oct. 7, 2014

(54) MEMBRANE TYPE-1 MATRIX METALLOPROTEIN INHIBITORS AND USES THEREOF

(75) Inventors: Richard Beliveau, Montreal (CA); Denis Gingras, Montreal (CA); Carine Nyalendo, Montreal (CA)

(73) Assignee: Angiochem, Inc., Montreal (CA)

( * ) Notice: Subject to any disclaimer, the term of this patent is extended or adjusted under 35 U.S.C. 154(b) by 186 days.

(21) Appl. No.: 13/139,931

(22) PCT Filed: Dec. 17, 2009

(86) PCT No.: PCT/CA2009/001858
§ 371 (c)(1),
(2), (4) Date: Sep. 1, 2011

(87) PCT Pub. No.: WO2010/069074
PCT Pub. Date: Jun. 24, 2010

(65) Prior Publication Data
US 2011/0305750 A1    Dec. 15, 2011

Related U.S. Application Data

(60) Provisional application No. 61/138,375, filed on Dec. 17, 2008.

(51) Int. Cl.
*A61K 38/55*    (2006.01)
*C07K 4/00*     (2006.01)
*C12N 9/64*     (2006.01)
*A61K 38/48*    (2006.01)

(52) U.S. Cl.
CPC .......... *A61K 38/4886* (2013.01); *C12N 9/6491* (2013.01)
USPC ........................................ 530/300; 424/20.1

(58) Field of Classification Search
None
See application file for complete search history.

(56) References Cited

U.S. PATENT DOCUMENTS

| | | | |
|---|---|---|---|
| 4,671,958 A | 6/1987 | Rodwell et al. |
| 4,801,575 A | 1/1989 | Pardridge |
| 4,902,505 A | 2/1990 | Pardridge et al. |
| 4,942,184 A | 7/1990 | Haugwitz et al. |
| 5,028,697 A | 7/1991 | Johnson et al. |
| 5,041,424 A | 8/1991 | Saulnier et al. |
| 5,118,668 A | 6/1992 | Auerswald et al. |
| 5,126,249 A | 6/1992 | Becker et al. |
| 5,204,354 A | 4/1993 | Chakravarty et al. |
| 5,223,409 A | 6/1993 | Ladner et al. |
| 5,258,499 A | 11/1993 | Konigsberg et al. |
| 5,362,831 A | 11/1994 | Mongelli et al. |
| 5,578,451 A | 11/1996 | Nishimoto |
| 5,627,270 A | 5/1997 | Kahne et al. |
| RE35,524 E | 6/1997 | Saulnier et al. |
| 5,683,694 A | 11/1997 | Bagshawe et al. |
| 5,780,265 A | 7/1998 | Dennis et al. |
| 5,807,980 A | 9/1998 | Lasters et al. |
| 5,948,750 A | 9/1999 | Garsky et al. |
| 5,948,888 A | 9/1999 | de la Monte et al. |
| 5,955,444 A | 9/1999 | Ingram et al. |
| 5,981,564 A | 11/1999 | Page et al. |
| 6,093,692 A | 7/2000 | Shen et al. |
| 6,126,965 A | 10/2000 | Kasid et al. |
| 6,245,359 B1 | 6/2001 | Milstein et al. |
| 6,310,039 B1 | 10/2001 | Kratz |
| 6,316,024 B1 | 11/2001 | Allen et al. |
| 6,348,207 B1 | 2/2002 | Milstein et al. |
| 6,376,648 B2 | 4/2002 | White et al. |
| 6,391,305 B1 | 5/2002 | Feng et al. |
| 6,469,047 B1 | 10/2002 | Jackson et al. |
| 6,475,481 B2 | 11/2002 | Talmadge |
| 6,475,781 B1 | 11/2002 | Mercola et al. |
| 6,495,513 B1 | 12/2002 | Rueger et al. |
| 6,613,890 B2 | 9/2003 | White et al. |
| 6,660,525 B2 | 12/2003 | Martin et al. |
| 6,713,454 B1 | 3/2004 | Ekwuribe et al. |
| 6,906,033 B2 | 6/2005 | White et al. |
| 7,019,123 B2 | 3/2006 | Tamburini et al. |
| 7,049,058 B2 | 5/2006 | Singh |
| 7,067,632 B2 | 6/2006 | Elliott |
| 7,101,844 B2 | 9/2006 | Kim et al. |
| 7,115,707 B2 | 10/2006 | Ben-Sasson et al. |
| 7,192,921 B2 | 3/2007 | Laakkonen et al. |
| 7,208,174 B2 | 4/2007 | Huwyler et al. |
| 7,214,657 B2 | 5/2007 | Kream |
| 7,319,090 B2 | 1/2008 | Katz |
| 7,557,182 B2 | 7/2009 | Béliveau et al. |

(Continued)

FOREIGN PATENT DOCUMENTS

| CA | 2283474 A1 | 9/1998 |
|---|---|---|
| CA | 2525236 A1 | 1/2005 |

(Continued)

OTHER PUBLICATIONS

UniProtKB/Swiss-Prot Acc. No. P50281. Downloaded Jun. 4, 2013.*

(Continued)

*Primary Examiner* — Sheridan Swope
(74) *Attorney, Agent, or Firm* — Clark & Elbing LLP; Kristina Bieker-Brady

(57) ABSTRACT

Based on the discovery that a soluble polypeptide including a nonphosphorylatable form of the MT1-MMP cytoplasmic domain is capable of inhibiting MT1-MMP in a dominant negative manner, the present invention provides compositions including MT1-MMP inhibitors such as peptide inhibitors, and methods for treating diseases associated with MT1-MMP activity. Such diseases include cancer, arthritis, and heart disease, and vascular disease.

17 Claims, 8 Drawing Sheets

(56) References Cited

U.S. PATENT DOCUMENTS

| | | |
|---|---|---|
| 8,530,429 B2 | 9/2013 | Robbins et al. |
| 8,569,323 B2 | 10/2013 | Ren et al. |
| 2003/0129186 A1 | 7/2003 | Béliveau et al. |
| 2004/0077540 A1 | 4/2004 | Quay |
| 2004/0087499 A1 | 5/2004 | Laakkonen et al. |
| 2004/0101904 A1 | 5/2004 | Pardridge et al. |
| 2004/0102369 A1 | 5/2004 | Wu et al. |
| 2004/0146549 A1 | 7/2004 | Ben-Sasson et al. |
| 2004/0162284 A1 | 8/2004 | Harris et al. |
| 2004/0220132 A1 | 11/2004 | Kaemmerer |
| 2005/0026823 A1 | 2/2005 | Zankel et al. |
| 2005/0042227 A1 | 2/2005 | Zankel et al. |
| 2005/0058702 A1 | 3/2005 | Ben-Sasson et al. |
| 2005/0100986 A1 | 5/2005 | Verma et al. |
| 2005/0178395 A1 | 8/2005 | Hunter et al. |
| 2005/0183731 A1 | 8/2005 | Hunter et al. |
| 2006/0019347 A1 | 1/2006 | Cho et al. |
| 2006/0029609 A1 | 2/2006 | Zankel et al. |
| 2006/0182684 A1 | 8/2006 | Beliveau |
| 2006/0189515 A1 | 8/2006 | Béliveau et al. |
| 2006/0251713 A1 | 11/2006 | Ben-Sasson et al. |
| 2007/0149444 A1 | 6/2007 | Laakkonen et al. |
| 2007/0167365 A1 | 7/2007 | Beliveau et al. |
| 2007/0172462 A1 | 7/2007 | Bohn et al. |
| 2007/0197460 A1 | 8/2007 | Fougerolles et al. |
| 2007/0207958 A1 | 9/2007 | Bridon et al. |
| 2008/0014143 A1 | 1/2008 | Ruoslahti et al. |
| 2008/0199436 A1 | 8/2008 | Sawada |
| 2008/0213185 A1 | 9/2008 | Hong et al. |
| 2008/0299039 A1 | 12/2008 | Beliveau et al. |
| 2009/0016959 A1 | 1/2009 | Beliveau et al. |
| 2009/0021883 A1 | 1/2009 | Delida |
| 2009/0082277 A1 | 3/2009 | Beliveau et al. |
| 2009/0215883 A1 | 8/2009 | Bouzada et al. |
| 2010/0284921 A1 | 11/2010 | Gordon et al. |
| 2011/0059187 A1 | 3/2011 | Basu et al. |
| 2012/0156130 A1 | 6/2012 | Hettmann et al. |
| 2012/0245169 A1 | 9/2012 | Ren et al. |
| 2013/0022546 A1 | 1/2013 | Wall et al. |
| 2013/0029982 A1 | 1/2013 | Castro et al. |
| 2013/0029984 A1 | 1/2013 | Castro et al. |
| 2013/0034572 A1 | 2/2013 | Stanimirovic et al. |
| 2013/0035069 A1 | 2/2013 | Fisher |
| 2013/0045873 A1 | 2/2013 | Hood et al. |
| 2013/0150314 A1 | 6/2013 | Myers et al. |
| 2013/0177499 A1 | 7/2013 | Brahmbhatt et al. |
| 2013/0195761 A1 | 8/2013 | Pereira et al. |

FOREIGN PATENT DOCUMENTS

| | | |
|---|---|---|
| CA | 2637893 A1 | 7/2007 |
| CA | 2638034 A1 | 7/2007 |
| CN | 101262890 A | 9/2008 |
| CN | 102406949 A | 4/2012 |
| CN | 102552928 A | 7/2012 |
| CN | 102614105 A | 8/2012 |
| DE | 19953696 A1 | 5/2001 |
| EP | 0495049 B1 | 7/1992 |
| EP | 1982699 A1 | 10/2008 |
| EP | 2333074 A1 | 6/2011 |
| JP | 2007-509977 A | 4/2007 |
| RU | 2172323 C2 | 10/1999 |
| WO | WO-87/05702 A1 | 9/1987 |
| WO | WO-96/31531 A2 | 10/1996 |
| WO | WO-96/39160 A1 | 12/1996 |
| WO | WO-00/01417 A1 | 1/2000 |
| WO | WO-01/30319 A1 | 5/2001 |
| WO | WO-02/33090 A2 | 4/2002 |
| WO | WO-02/43765 A2 | 6/2002 |
| WO | WO 02/085923 A2 | 10/2002 |
| WO | WO-03/009815 A2 | 2/2003 |
| WO | WO-03/102583 A1 | 12/2003 |
| WO | WO-2004/060403 A2 | 7/2004 |
| WO | WO-PCT/JP2004/011668 | 8/2004 |
| WO | WO-2004/093897 A1 | 11/2004 |
| WO | WO-2004/108071 A2 | 12/2004 |
| WO | WO-2005/002515 A2 | 1/2005 |
| WO | WO-2005/014625 A1 | 2/2005 |
| WO | WO-2005/021579 A2 | 3/2005 |
| WO | WO-2005/042029 A2 | 5/2005 |
| WO | WO-2006/086870 A1 | 8/2006 |
| WO | WO-2006/089290 A1 | 8/2006 |
| WO | WO-2006/108052 A2 | 10/2006 |
| WO | WO-2006/138343 A2 | 12/2006 |
| WO | WO-2007/009229 A1 | 1/2007 |
| WO | WO-2007/020085 A2 | 2/2007 |
| WO | WO-2007/035716 A2 | 3/2007 |
| WO | WO-2007/044323 A2 | 4/2007 |
| WO | WO-2007/082978 A1 | 7/2007 |
| WO | WO-2007/082979 A1 | 7/2007 |
| WO | WO-2008/012629 A2 | 1/2008 |
| WO | WO-2008/036682 A2 | 3/2008 |
| WO | WO-2008/046228 A1 | 4/2008 |
| WO | WO-2008/116171 A1 | 9/2008 |
| WO | WO 2008/144919 A1 | 12/2008 |
| WO | WO-2009/039188 A2 | 3/2009 |
| WO | WO-2009/046220 A2 | 4/2009 |
| WO | WO-2009/070597 A2 | 6/2009 |
| WO | WO-2009/079790 A1 | 7/2009 |
| WO | WO-2009/105671 A2 | 8/2009 |
| WO | WO-2009/127072 A1 | 10/2009 |
| WO | WO-2010/006239 A2 | 1/2010 |
| WO | WO-2010/043047 A1 | 4/2010 |
| WO | WO-2010/043049 A1 | 4/2010 |
| WO | WO-2010/063122 A1 | 6/2010 |
| WO | WO-2010/063123 A1 | 6/2010 |
| WO | WO-2010/063124 A1 | 6/2010 |
| WO | WO-2010/121379 A1 | 10/2010 |
| WO | WO-2010/142035 A1 | 12/2010 |
| WO | WO-2011/000095 A1 | 1/2011 |
| WO | WO-2011/008823 A2 | 1/2011 |
| WO | WO-2011/041897 A1 | 4/2011 |
| WO | WO-2011/063507 A1 | 6/2011 |
| WO | WO-2011/112635 A1 | 9/2011 |
| WO | WO-2011/153642 A1 | 12/2011 |
| WO | WO-2012/000118 A1 | 1/2012 |
| WO | WO-2012/006239 A1 | 1/2012 |
| WO | WO-2012/037687 A1 | 3/2012 |
| WO | WO-2012/064973 A2 | 5/2012 |
| WO | WO-2012/068531 A2 | 5/2012 |
| WO | WO-2012/097000 A1 | 7/2012 |
| WO | WO-2012/118376 A1 | 9/2012 |
| WO | WO-2012/135025 A2 | 10/2012 |
| WO | WO-2012/138694 A2 | 10/2012 |
| WO | WO-2012/153286 A1 | 11/2012 |
| WO | WO-2012/162807 A1 | 12/2012 |
| WO | WO-2013/004716 A1 | 1/2013 |
| WO | WO-2013/012915 A1 | 1/2013 |
| WO | WO-2013/023184 A1 | 2/2013 |
| WO | WO-2013/032591 A1 | 3/2013 |
| WO | WO-2013/049332 A1 | 4/2013 |
| WO | WO-2013/056096 A1 | 4/2013 |
| WO | WO-2013/063468 A1 | 5/2013 |
| WO | WO-2013/071272 A1 | 5/2013 |
| WO | WO-2013/078562 A2 | 6/2013 |
| WO | WO-2013/078564 A2 | 6/2013 |
| WO | WO-2013/090861 A1 | 6/2013 |
| WO | WO-2013/120107 A1 | 8/2013 |
| WO | WO-2013/131032 A1 | 9/2013 |
| WO | WO-2013/151774 A1 | 10/2013 |
| WO | WO-2013/162757 A1 | 10/2013 |
| WO | WO-2013/185235 A1 | 12/2013 |

OTHER PUBLICATIONS

Derossi et al, The third helix of the Antennapedia homeodomain translocates through biological membranes. J Biol Chem. Apr. 8, 1994;269(14):10444-50.*

Nyalendo et al, Src-dependent Phosphorylation of Membrane Type I Matrix Metalloproteinase on Cytoplasmic Tyrosine 573: Role in Endothelial and Tumor Cell Migration. J. Biol. Chem. 2007, 282:15690-15699. Published online Mar. 27, 2007.*

Belkin et al., "Matrix-dependent proteolysis of surface transglutaminase by membrane-type metalloproteinase regulates

(56) References Cited

OTHER PUBLICATIONS cancer cell adhesion and locomotion," *J. Biol. Chem.* 276: 1 8415-184122 (2001).
U.S. Appl. No. 61/138,375, filed Dec. 17, 2008, Béliveau et al.
Brady and Dodson, "Reflections on a peptide," *Nature* 368: 692-693 (1994).
Carell et al., "A novel procedure for the synthesis of libraries containing small organic molecules," *Angew. Chem. Int. Ed. Engl.* 33: 2059-2061 (1994).
Carell et al., "A solution-phase screening procedure for the isolation of active compounds from a library of molecules," *Angew. Chem. Int. Ed. Engl.* 33: 2061-2064 (1994).
Cho et al., "An unnatural biopolymer," *Science* 3: 1303-1305 (1993).
Cull et al., "Screening for receptor ligands using large libraries of peptides linked to the C terminus of the *lac* repressor," *Proc. Natl. Acad. Sci. USA*. 89: 1865-1869 (1992).
D'Ortho et al., "Membrane-type matrix metalloproteinases 1 and 2 exhibit broad-spectrum proteolytic capacities comparable to many matrix metalloproteinases," *Eur. J. Biochem.* 250: 751-757 (1997).
DeWitt et al., ""Diversomers": An approach to nonpeptide, nonoligomeric chemical diversity," *Proc. Natl. Acad. Sci.* USA 90: 6909-6913 (1993).
Erb et al., "Recursive deconvoluation of combinatorial chemical libraries," *Proc. Natl. Acad. Sci. USA* 91: 11422-11426 (1994).
Evans et al., "Design of nonpeptidal ligands for the peptide receptor: cholecystokinin antagonists," *J. Med. Chem.* 30: 1229-1239 (1987).
Fauchere et al., "Association with the HeLa cells of *Campylobacter jejuni* and *Campylobacter coli* isolated from human feces," *Infect. Immun.* 54: 283-287 (1986).
Fodor et al., "Multiplexed biochemical assays with biological chips," *Nature* 364: 555-556 (1993).
Gallop et al., "Application of combinatorial technologies to drug discovery. 1. Background and peptide combinatorial libraries," *J. Med. Chem.* 37: 1233-1251 (1994).
Halab et al., "Design, synthesis, and conformational analysis of azacycloalkane amino acids as conformationally constrained probes for mimicry of peptide secondary structures," *Biopoly.* 55: 101-122 (2000).
Hanessian et al., "Synthesis of (4S)-hydroxymethyl-(2R)-(2-propyl)-butyrolactone: A quest for a practical route to an important hydroxyethylene isostere chiron," *Tetrahedron* 53: 6281-6294 (1997).
Hijova, E., "Matrix metalloproteinases: their biological functions and clinical implication," *Bratisl Lek. Listy.* 106: 127-132 (2005).
Hiraoka et al., "Matrix metalloproteinases regulate neovascularization by acting as a pericellular fibrinolysins" *Cell* 95: 365-377 (1998).
Hong et al., "Coexpression of cyclooxygenase-2 and matrix metalloproteinases in human aortic atheroscletoric lesions," *Yonsei Med. J.* 41:82-88 (2000).
Hotary et al., "Membrane type I matrix metalloproteinase usurps tumor growth control imposed by the three-dimensional extracellular matrix," *Cell* 114: 33-45 (2003).
Hudson et al., "Methionine enkephalin and isosteric analogues. I. Synthesis on a phenolic resin support," *Int. J. Pept. Protein. Res.* 14: 177-185 (1979).
Imai et al., "Expressions of membrane-type 1 matrix metalloproteinase and activation of progelatinase A in human osteoarthritic cartilage," *Am. J. of Pathol.* 151: 245-256 (1997).
Jameson et al., "A rationally designed CD4 analouge inhibits experimental allergic encephalomyelitis," *Nature* 368: 744-746 (1994).
Kajita et al., "Membrane-type 1 matrix metalloproteinase cleaves CD44 and promotes cell migration," *Journal of Cell Biol.* 153: 893-904 (2001).
Kamps et al., "Uptake of long-circulating immunoliposomes, directed against colon adenocarcinoma cells, by liver metastases of colon cancer," *J. Drug Targeting* 8: 235-245 (2000).
Kirpotin et al., "Sterically stabilized anti-HER2 immunoliposomes: Design and targeting to human breast cancer cells in vitro," *Biochem.* 36: 66-75(1997).

Konttinen et al., "Analysis of 16 different matrix metalloproteinases (MMP-1 to MMP-20) in the synovial membrane: different profiles in trauma and rheumatoid arthritis." *Ann. Rheum. Dis.* 58 :691-697 (1999).
Lam, K., "Application of combinatorial library methods in cancer research and drug discovery," *Anti-cancer Drug Des.* 12: 145-167 (1997).
Lam et al., "A new type of synthetic peptide library for identifying ligand-binding activity," *Nature* 354 :82-84 (1991).
Langer, R., "New methods of drug delivery," *Science* 249: 1527-1533 (1990).
Moase et al., "Anti-MUC-1 immunoliposomal doxorubicin in the treatment of murine models of metastatic breast cancer," *Biochim. Biophys. Acta.* 1510: 43-55 (2001).
Nakada et al., "Expression and tissue localization of membrane-type 1, 2, and 3 matrix metalloproteinases in human astrocytic tumors," *American Journal of Pathology* 154: 417-428 (1999).
Nam et al., "Sterically stabilized anti-$G_{M3}$, anti-Le$^x$ immunoliposomes: targeting to B16BL6, HRT-18 cancer cells," *Oncol. Res.* 11:9-16 (1999).
Nyalendo et al., "Src-dependent phosphorylation of membrane type I matrix metalloproteinase on cytoplasmic tyrosine 573: role in endothelial and tumor cell migration," *J. Biol. Chem.* 282: 15690-15699 (2007).
Nyalendo et al., "Impaired tyrosine phosphorylation of membrane type 1-matrix metalloproteinase reduces tumor cell proliferation in three-dimensional matrices and abrogates tumor growth in mice," *Carcinogenisis* 29: 1655-1664 (2008).
Pardridge et al., "Selective transport of an anti-transferrin receptor antibody through the blood-brain barrier in vivo," *J. Pharacol. Exp. Ther.* 259 :66-70 (1991).
Park et al., "Development of anti-p185$^{HER2}$ immunoliposomes for cancer therapy," *Proc. Natl. Acad. Sci. USA*. 92 :1327-1331 (1995).
Pei and Weiss, "Transmembrane-deletion mutants of the membrane-type matrix metalloproteinase-1 process progelatinase A and express intrinsic matrix-degrading activity," *J. Biol. Chem.* 271: 9135-9140 (1996).
Powell et al., "Peptide stability in drug development. II. Effect of single amino acid substitution and glycosylation on peptide reactivity in human serum," *Pharm. Res.* 10: 1268-1273 (1993).
Rizo and Gierasch, "Constrained peptides: models of bioactive peptides and protein substructure," *Annu. Rev. Biochem*. 61: 387-418 (1992).
Sabeh et al., "Tumor cell traffic through the extracellular matrix is controlled by the membrane-anchored collagenase MT1-MMP," *J.Cell Biol.* 167: 769-781 (2004).
Sahm et al., "Receptor binding affinities and biological activities of linear and cyclic melanocortins in B16 murine melanoma cells expressing the native MC1 receptor," *J. Pharm. Pharmacol.* 48: 197-200 (1996).
Scott and Smith, "Searching for peptide ligans with an epitope library," *Science* 249: 386-390 (1990).
Spatola et al., "Structure-activity relationships of enkephalins containing serially replaced thiomethylene amide bond surrogates," *Life Sci*. 38: 1243-1249 (1986).
Tilstra et al., "Protein transduction: identification, characterization and optimization," *Biochem. Soc. Trans.* 35: 811-815 (2007).
Tripathi et al., "Membrane type 1 matrix metalloproteinase expression in human atherosclerotic plaques: evidence for activation by proinflammatory mediators," *Circulation* 99: 3103-3109 (1999).
Uekita et al., "Cytoplasmic tail-dependent internalization of membrane-type 1 matrix metalloproteinase is important for its invasion-promoting activity," *J. Cell Biol.* 155: 1345-1356 (2001).
Uekita et al., "Membrane-type 1 matrix metalloproteinase cytoplasmic tail-binding protein-1 is a new member of the cupin superfamily: A possible multifunctional protein acting as an invasion suppressor down-regulated in tumors," *J. Biol. Chem.* 279: 12734-12743 (2004).
Zhai et al., "Expression of membrane type 1 matrix metalloproteinase is associated with cervical carcinoma progression and invasion," *Cancer Res*. 65: 6543-6550 (2005).

(56) References Cited

OTHER PUBLICATIONS

Zuckermann et al., "Discovery of nanomolar ligands for 7-transmembrane G-protein-coupled receptors from a diverse N-(substituted) glycine peptoid library," *J. Med. Chem.* 37:2678-2685 (1994).
American College of Rheumatology Subcommittee on Rheumatoid Arthritis Guidelines, "Guidelines for management of rheumatoid arthritis: 2002 update," *Arthritis & Rheumatism* 46:328-346 (2002).
European Search Report for Application No. EP09832788.5 mailed Jul. 26, 2012 (6 pages).
International Search Report and Written Opinion for PCT/CA2009/001858 mailed Mar. 23, 2010 (15 pages).
Author manuscript of Howes et al., "Rapid induction of therapeutic hypothermia using convective-immersion surface cooling: Safety, efficacy and outcomes," published in final edited form as: Resuscitation. 81(4):388-392 (2010); (13 pages).
Ballabh et al., "The blood-brain barrier: an overview structure, regulation, and clinical implications," Neurobiol Dis. 16:1-13 (2004).
Bickel et al., "Delivery of peptides and proteins through the blood-brain barrier," Adv Drug Deliv Rev. 46:247-279 (2001).
Boado et al., "GDNF fusion protein for targeted-drug delivery across the human blood-brain barrier," Biotechnol Bioeng. 100(2):387-96 (2008).
Boado, "Blood-brain barrier transport of non-viral gene and RNAi therapeutics," Pharm Res. 24(9):1772-87 (2007).
Bork et al., "Go hunting in sequence databases but watch out for the traps," Trends Genet. 12:425-427 (1996).
Bork, "Powers and pitfalls in sequence analysis: the 70% hurdle," Genome Res. 10:398-400 (2000).
Boules et al., "Bioactive analogs of neurotensin: focus on CNS effects," Peptides. 27(10): 2523-2533 (2006).
Brenner, "Errors in genome annotation," Trends Genet. 15:132-133 (1999).
Buvanendran et al., "Recent advances in nonopioid analgesics for acute pain management," Tech Reg Anesth Pain Man. 11(1):19-26 (2007).
Castex et al., "2-Pyrrolinodoxorubicin and its peptide-vectorized form bypass multidrug resistance," Anticancer Drugs. 15:609-617 (2004).
Chen et al., "Synthesis of doxorubicin conjugates through hydrazone bonds to melanotransferrin P97," Synth Commun. 33(14):2377-2390 (2003).
Chu et al., "Detection of soluble P-glycoprotein in culture media and extracellular fluids," Biochem Biophys Res Commun. 203(1):506-512 (1994).
Coon et al., "Solutol HS 15, nontoxic polyoxyethylene esters of 12-hydroxystearic acid, reverses multidrug resistance," Cancer Res. 51:897-902 (1991).
Cui et al., "PAMAM-drug complex for delivering anticancer drug across blood-brain barrier in-vitro and in-vivo," Afr J Pharm Pharmacol. 3(5):227-233 (2009).
D'Onofrio et al., "Glycomimetics as decorating motifs for oligonucleotides: solid-phase synthesis, stability, and hybridization properties of carbopeptoid-oligonucleotide conjugates," Bioconjug Chem. 16:1299-1309 (2005).
Dagenais et al., "Development of an in situ mouse brain perfusion model and its application to mdr1a P-glycoprotein-deficient mice," J Cereb Blood Flow Metab. 20:381-386 (2000).
Deane et al., "LRP/Amyloid β-Peptide interaction mediates differential brain efflux of Aβ isoforms," Neuron. 43:333-344 (2004).
Declaration of Michel Demeule in European Patent Application No. 11010125 dated Sep. 24, 2012 (4 pages).
Dehouck et al., "A new function for the LDL receptor: transcytosis of LDL across the blood-brain barrier," J Cell Biol. 138(4):877-889 (1997).
Dehouck et al., "An easier, reproducible, and mass-production method to study the blood-brain barrier in vitro," J Neurochem. 54(5):1798-1801 (1990).
Dehouck et al., "Drug transfer across the blood-brain barrier: correlation between in vitro and in vivo models," J Neurochem. 58(5):1790-1797 (1992).
Demeule et al., "High transcytosis of melanotransferrin (P97) across the blood-brain barrier," J Neurochem. 83:924-933 (2002).
Demeule et al., "Identification and design of peptides as a new drug delivery system for the brain," J Pharmacol Exp Ther. 324(3):1064-1072 (2008).
Demeule et al., "Isolation of endothelial cells from brain, lung, and kidney: expression of the multidrug resistance P-Glycoprotein isoforms," Biochem Biophys Res Commun. 281:827-834 (2001).
Demule et al., "ANG2002: A new Angiochem-modified neurotensin with increased brain penetration and analgesic properties," Program No. 374.11/QQ6 2010 Neuroscience Meeting Planner, San Diego, CA: Society for Neuroscience (2010) (5 pages).
Doerks et al., "Protein annotation: detective work for function prediction," Trends Genet. 14:248-250 (1998).
Fillebeen et al., "Receptor-mediated transcytosis of lactoferrin through the blood-brain barrier," J Biol Chem. 274:7011-7017 (1999).
Fioretti et al., "Aprotinin-like isoinhibitors in bovine organs," Biol Chem Hoppe Seyler. 369 Suppl:37-42 (1988).
Fromm, "P-glycoprotein: a defense mechanism limiting oral bioavailability and CNS accumulation of drugs," Int J Clin Pharmacol Ther. 38:69-74 (2000).
Furuta et al., "Structure-antinociceptive activity studies with neurotensin," Br J Pharmacol. 83(1):43-48 (1984).
Gabathuler, "Approcaches to transport therapeutic drugs across the blood-brain barrier to treat brain diseases," Neurobiol Dis. 37(1):48-57 (2010).
Gelmon, "The taxoids: paclitaxel and docetaxel," Lancet. 344:1267-1272 (1994).
Gewirtz, "A critical evaluation of the mechanisms of action proposed for the antitumor effects of the anthracycline antibiotics adriamycin and daunorubicin," Biochem Pharmacol. 57:727-741 (1999).
Grabb et al., "Neoplastic and pharmacological influence on the permeability of an in vitro blood-brain barrier," J Neurosurg. 82:1053-1058 (1995).
Guillot et al., "Angiotensin peptide regulation of bovine brain microvessel endothelial cell monolayer permeability," J Cardiovasc Pharmacol. 18:212-218 (1991).
Gumbleton et al., "Progress and limitations in the use of in vitro cell cultures to serve as a permeability screen for the blood-brain barrier," J Pharm Sci. 90:1681-1698 (2001).
Hawkins et al., "The blood-brain barrier/neurovascular unit in health and disease," Pharmacol Rev. 57:173-185 (2005).
Hein et al., "Click chemistry, a powerful tool for pharmaceutical sciences," Pharm Res. 25(10):2216-2230 (2008).
Huang et al., "Production of bioactive human beta-defensin 5 and 6 in *Escherichia coli* by soluble fusion expression," Protein Expr Purif. 61(2):168-174 (2008).
Hussain et al., "The mammalian low-density lipoprotein receptor family," Annu Rev Nutr. 19:141-172 (1999).
Ito et al., "Functional characterization of the brain-to-blood efflux clearance of human amyloid-β peptide (1-40) across the rat blood-brain barrier," Neurosci Res. 56:246-252 (2006).
Itoh et al., "MT1-MMP: a potent modifier of pericellular microenvironment," J Cell Physiol. 206(1):1-8 (2006).
Ke et al., "Gene delivery targeted to the brain using an angiopep-conjugated polyethyleneglycol-modified polyamidoamine dendrimer," Biomaterials. 30(36):6976-85 (2009).
Kesari et al., "Phase II study of temozolomide, thalidomide, and celecoxib for newly diagnosed glioblastoma in adults," Neuro Oncol. 10(3):300-308 (2008).
Kiernan et al., "Fluorescent-labelled aprotinin: A new reagent for the histochemical detection of acid mucosubstances," Histochemie. 34: 77-84 (1973).
Kilic et al., "Intravenous Tat-Gdnf is protective after focal cerebral ischemia in mice," Stroke. 34(5):1304-10 (2003).
Kobayashi et al., "The protease inhibitor bikunin, a novel anti-metastatic agent," Biol Chem. 384:749-754 (2003).

(56) References Cited

OTHER PUBLICATIONS

Koo et al., "Differential expression of amyloid precursor protein mRNAs in cases of alzheimer's disease and in aged nonhuman primates," Neuron. 2:97-104 (1990).
Kounnas et al, "LDL receptor-related protein, a multifu nctional ApoE receptor, binds secreted beta-amyloid precursor protein and mediates Its degradation," Cell. 82:331-340 (1995).
Koziara et al., "In situ blood-brain barrier transport of nanoparticles," Pharm Res. 20:1772-1778 (2003).
Kreuter et al., "Apolipoprotein-mediated transport of nanoparticle-bound drugs across the blood-brain barrier," J Drug Target. 10:317-325 (2002).
Kreuter et al., "Direct evidence that polysorbate-80-coated poly(Butylcyanoacrylate) nanoparticles deliver drugs to the CNS via specific mechanisms requiring prior binding of drug to the nanoparticles," Pharm Res. 20:409-416 (2003).
Kreuter, "Nanoparticulate carriers for drug delivery to the brain," Nanoparticles as Drug Carriers, Torchilin VP, Imperial College Press, London pp. 527-547 (2006).
Kurzrock et al., "ANG1005, an Angiopep-2/paclitaxel conjugate: The first clinical trial in patients with advanced cancer and brain metastases: Preliminary safety and tolerability data," 20th EORTC-NCI-AACR Symposium on "Molecular Targets and Cancer Therapeutics", Euro J of Cancer. 6(12):133, Abstract 424 (2008).
Kurzrock et al., "ANG1005: Results of a Phase I study in patients with advanced solid tumors and metastatic brain cancer," Poster B168, ACCR/NCI/EORTC Annual Meeting (2009) (2 pages).
Laccabue et al., "A novel taxane active against an orthotopically growing human glioma xenograft," Cancer. 92:3085-3092 (2001).
Lachowicz et al., "Analgesic properties of a novel brain-penetrant Angiopep-2-neurotensin derivative (ANG2002) for treating chronic pain," Program No. 173.28/AA9 2012 Neuroscience Meeting Planner, New Orleans, LA: Society for Neuroscience (2012).
Lai et al., "The critical component to establish in vitro BBB model: pericyte," Brain Res Rev. 50:258-265 (2005).
Larionova et al., "Carbohydrate-containing derivatives of the trypsin-kallikrein inhibitor aprotinin from bovine organs II. inhibitor coupled to the (Carboxymethyl)dextran derivatives of D-galactose," Biol Chem Hoppe-Seyler. 366:743-748 (1985).
Larsson, "Megalin, an endocytic receptor with signalling potential," Acta Universitatis Upsaliensis Uppsala 1-58 (2006).
Ma et al., "Cationic charge-dependent hepatic delivery of amidated serum albumin," J Control Release. 102:583-594 (2005).
Mamot et al., "Epidermal growth factor receptor (EGFR)-targeted immunoliposomes mediate specific and efficient drug delivery to EGFR- and EGFRvIII-overexpressing tumor cells," Cancer Res. 63(12):3154-61 (2003).
Marinò et al., "Megalin-mediated transcytosis of thyroglobulin by thyroid cells is a calmodulin-dependent process," Thyroid. 10(6):461-469 (2000).
Marinò et al., "Transcytosis of retinol-binding protein across renal proximal tubule cells after megalin (gp 330)-mediated endocytosis," J Am Soc Nephrol. 12:637-648 (2001).
Markman et al., "Phase II trial of weekly single-agent paclitaxel in platinum/paclitaxel-refractory ovarian cancer," J Clin Oncol. 20(9):2365-9 (2002).
Martel et al., "Transport of apolipoproteins E and J at the blood-brain barrier relevance to Alzheimer's disease," S.T.P. Pharma Sciences. 7(1):28-36 (1997).
Martinez-Fong et al., "Neurotensin-SPDP-poly-L-lysine conjugate: a nonviral vector for targeted gene delivery to neural cells," Molecular Brain Research 69:249-262 (1999).
Mazel et al., "Doxorubicin-peptide conjugates overcome multidrug resistance," Anticancer Drugs. 12:107-116 (2001).
McCarty, "Cell biology of the neurovascular unit: implications for drug delivery across the blood-brain barrier," Assay Drug Dev Technol. 3(1):89-95 (2005).
Michaud et al., "Risks and benefits of taxanes in breast and ovarian cancer," Drug Saf. 23(5):401-28 (2000).

Moestrup et al., "Evidence that epithelial glycoprotein 330/Megalin mediates uptake of polybasic drugs," J.Clin. Invest. 96:1404-1413 (1995).
Moore et al., "The role of flexible tethers in multiple ligand-receptor bond formation between curved surfaces," Biophys J. 91:1675-1687 (2006).
Muratovska et al., "Conjugate for efficient delivery of short interfering RNA (siRNA) into mammalian cells," FEBS Lett. 558:63-68 (2004).
Ngo et al., "Computational complexity: protein structure prediction, and the levinthal paradox," The Protein Folding Problem and Tertiary Structure Prediction Merz, Jr. and Le Grand, Eds. 491-495 (1994).
Niola et al., "A plasmid-encoded VEGF siRNA reduces glioblastoma angiogenesis and Its combination with interleukin-4 Blocks tumor growth in a xenograft mouse model," Cancer Biol Ther. 5:174-179 (2006).
Office Action and its English translation for Chinese Patent Application No. 200980155900.0, dated Jun. 4, 2012 (13 pages).
Orlando et al., "Identification of the second cluster of ligand-binding repeats in megalin as a site for receptor-ligand interactions," Proc Natl Acad Sci USA. 94:2368-2373 (1997).
Pan et al., "Efficient transfer of receptor-associated protein (RAP) across the blood-brain barrier," J Cell Sci. 117(21):5071-5078 (2004).
Pardridge et al. "Combined use of carboxyl-directed protein pegylation and vector-mediated blood-brain barrier drug delivery system optimizes brain uptake of brain-derived neurotrophic factor following intravenous administration," Pharm Res. 15(4):576-582 (1998).
Pardridge, "Blood-brain barrier biology and methodology," J Neurovirol. 5:556-569 (1999).
Pardridge, "CNS drug design based on principles of blood-brain barrier transport," J Neurochem. 70:1781-1792 (1998).
Pardridge, "Drug targeting to the brain," Pharm Res. 24(9):1733-1744 (2007).
Pardridge, "Vector-mediated drug delivery to the brain," Adv Drug Deliv Rev. 36(2-3):299-321 (1999).
Park et al., "Recombinant expression of biologically active rat leptin in *Escherichia coli*," Protein Expr Purif. 22(1):60-69 (2001).
Pathan et al. "CNS drug delivery systems: novel approaches," Recent Pat Drug Deliv Formul. 3(1):71-89 (2009).
Peri et al., "D-Glucose as a regioselectively addressable scaffold for combinatorial chemistry on solid phase," J Carbohydr Chem. 22(1):57-71 (2003).
Prince et al., "Lipoprotein receptor binding, cellular uptake, and lysosomal delivery of fusions between the receptor-associated protein (RAP) and alpha-L-Iduronidase or Acid alpha-Glucosidase," J Biol Chem. 279(33):35037-35046 (2004).
Qu et al., "Carbohydrate-based micelle clusters which enhance hydrophobic drug bioavailability by up to 1 order of magnitude," Biomacromolecules. 7:3452-3459 (2006).
Rajavashisth et al., "Membrane type 1 matrix metalloproteinase expression in human atherosclerotic plaques: evidence for activation by proinflammatory mediators," Circulation. 99(24):3103-9 (1999).
Ramakrishnan, "The role of P-glycoprotein in the blood-brain barrier," Einstein Q J Biol Med. 19:160-165 (2003).
Rawat et al., "Lipid carriers: a versatile delivery vehicle for proteins and peptides," Yakugaku Zasshi. 128(2):269-280 (2008).
Rose et al., "Metastatic patterns in histologic variants of ovarian cancer. An autopsy study," Cancer. 64(7):1508-13 (1989).
Rudikoff et al., "Single amino acid substitution altering antigen-binding specificity," Proc Natl Acad Sci USA. 79:1979-83 (1982).
Régina et al., "Antitumour activity of ANG1005, a conjugate between paclitaxel and the new brain delivery vector angiopep-2," Br J Pharmacol. 155:185-197 (2008).
Régina et al., "Differences in multidrug resistance phenotype and matrix metalloproteinases activity between endothelial cells from normal brain and glioma," J Neurochem. 84:316-324 (2003).
Scherrmann, "Drug delivery to brain via the blood-brain barrier," Vascul Pharmacol. 38:349-354 (2002).
Schinkel, "P-Glycoprotein, a gatekeeper in the blood-brain barrier," Adv Drug Deliv Rev. 36:179-194 (1999).
Seidel et al., "Effects of trasylol on the blood-brain barrier in rats," Naunyn Schmiedebergs Arch Pharmacol. 284:R73 (1974).

(56) References Cited

OTHER PUBLICATIONS

Seiden et al., "A phase II study of the MDR inhibitor biricodar (INCEL, VX-710) and paclitaxel in women with advanced ovarian cancer refractory to paclitaxel therapy," Gynecol Oncol. 86(3):302-10 (2002).
Shao et al., "Angiopep-2 modified PE-PEG based polymeric micelles for amphotericin B delivery targeted to the brain," J Control Release. 147(1):118-26 (2010).
Shibata et al., "Clearance of Alzheimer's amyloid-ss(1-40) peptide from brain by LDL receptor-related protein-1 at the blood-brain barrier," J Clin Invest. 106(12):1489-1499 (2000).
Shiiki et al., "Brain insulin impairs amyloid-beta(1-40) clearance from the brain," J Neurosci. 24(43):9632-9637 (2004).
Shimura et al., "Transport mechanism of a new behaviorally highly potent adrenocorticotropic hormone (ACTH) analog, ebiratide, through the blood-brain barrier," J Pharmacol Exp Ther. 258(2):459-465 (1991).
Skolnick et al., "From genes to protein structure and function: novel applications of computational approaches in the genomic era," Trends Biotechnol. 18:34-39 (2000).
Smith et al., "The challenges of genome sequence annotation or 'The devil is in the details'," Nat Biotechnol. 15:1222-1223 (1997).
Smith, "Brain perfusion systems for studies of drug uptake and metabolism in the central nervous system," Pharm Biotechnol. 8:285-307 (1996).
Steiniger et al., "Chemotherapy of glioblastoma in rats using doxorubicin-loaded nanoparticles," Int J Cancer. 109:759-767 (2004).
Svenson et al., "Dendrimers in biomedical applications—reflections on the field," Adv Drug Deliv Rev. 57(15):2106-2129 (2005).
Tamai et al., "Structure-internalization relationship for absorptive-mediated endocytosis of basic peptides at the blood-brain barrier," J Pharmacol Exp Ther. 280(1):410-415 (1997).
Temsamani et al., "Vector-mediated drug delivery to the brain," Expert Opin Biol Ther. 1(5):773-782 (2001).
Terasaki et al., "New approaches to in vitro models of blood-brain barrier drug transport," Drug Discov Today. 8(20):944-954 (2003).
Triguero et al., "Capillary depletion method for quantification of blood-brain barrier transport of circulating peptides and plasma proteins," J Neurochem. 54(6):1882-1888 (1990).
Turner et al., "RNA targeting with peptide conjugates of oligonucleotides, siRNA and PNA," Blood Cells Mol Dis. 38:1-7 (2007).
UniProt Consortium, "P08183 (MDR1_HUMAN)," <http://www.uniprot.org/uniprot/P08183>, retrieved on Sep. 18, 2013 (16 pages).
Veronese et al., "PEGylation, successful approach to drug delivery," Drug Discov Today. 10:1451-1458 (2005).
Vincent, "Neurotensin receptors: binding properties, transduction pathways, and structure," Cell Mol Neurobiol. 15(5):501-512 (1995).
Wang et al., "Dna/dendrimer complexes mediate gene transfer into murine cardiac transplants ex Vivo," Mol Ther. 2(8):602-608 (2000).
Wang et al., "Polyamidoamine dendrimers with a modified Pentaerythritol core having high efficiency and low cytotoxicity as gene carriers," Biomacromolecules. 10(3):617-622 (2009).
Wang et al., "Synthesis and antinociceptive effects of endomorphin-1 analogs with C-terminal linked by oligoarginine," Peptides. 32(2):293-9 (2011).
Wells, "Additivity of mutational effects in proteins," Biochemistry. 29(37):8509-8517 (1990).
Williamson et al., "Expression and purification of recombinant neurotensin in *Escherichia coli*," Protein Expr Purif. 19(2):271-5 (2000).
Witt et al., "Peptide drug modifications to enhance bioavailability and blood-brain barrier permeability," Peptides. 22:2329-2343 (2001).
Xu et al., "In vitro and in vivo evaluation of actively targetable nanoparticles for paclitaxel delivery," Int J Pharm. 288:361-368 (2005).
Yano et al., "Simultaneous activation of two different receptor systems by enkephalin/neurotensin conjugates having spacer chains of various lengths," Eur J Pharm Sci. 7:41-48 (1998).
Yepes et al., "Tissue-type plasminogen activator induces opening of the blood-brain barrier via the Ldl receptor-related protein," J Clin Invest. 112(10):1533-1540 (2003).
Zhang et al. "In vitro gene delivery using polyamidoamine dendrimers with a trimesyl core," Biomacromolecules. 6(1):341-350 (2005).
Zhang et al., "Intravenous RNA interference gene therapy targeting the human epidermal growth factor receptor prolongs survival in intracranial brain cancer," Clin Cancer Res. 10:3667-3677 (2004).
Zhang et al., "Silencing the epidermal growth factor receptor gene with RNAi may be developed as a potential therapy for non small cell lung cancer," Genet Vaccines Ther. 3(5):1-12 (2005).
Zhang et al., "siRNA-containing liposomes modified with polyarginine effectively silence the targeted gene," J Control Release. 112:229-239 (2006).
Zlokovic et al., "Glycoprotein 330/Megalin: probable role in receptor-mediated transport of apolipoprotein J alone and in a complex with Alzheimer disease amyloid Beta at the blood-brain and blood cerebrospinal fluid barriers," Proc Natl Acad Sci U S A. 93:4229-4234 (1996).

\* cited by examiner

Dose: 10 mg/kg
Cells: Fibrosarcoma (HT-1080)
scACM-14: scrambled ACM-14

Dose: 10 mg/kg
Cells: Fibrosarcoma (HT-1080)
scACM-14: scrambled ACM-14

US 8,853,353 B2

MEMBRANE TYPE-1 MATRIX METALLOPROTEIN INHIBITORS AND USES THEREOF

CROSS-REFERENCE TO RELATED APPLICATIONS

This application is the U.S. national stage filing under 35 U.S.C. §371 of international application PCT/CA2009/001858, filed Dec. 17, 2009, which claims benefit of Provisional Patent Application 61/138,375, filed Dec. 17, 2008.

BACKGROUND OF THE INVENTION

The invention relates to compounds capable of inhibiting the membrane type-1 metalloproteinase (MT1-MMP or MMP-14), and methods treating diseases such as cancer, heart and vascular disease, and arthritis using these compounds.

Breakdown and remodeling of the extracellular matrix (ECM) has been implicated in disease processes, including cancer, heart and vascular disease, and arthritis.

Cancer is a disease marked by the uncontrolled growth of abnormal cells. Cancer cells have overcome the barriers imposed in normal cells, which have a finite lifespan, to grow indefinitely. As the growth of cancer cells continue, genetic alterations may persist until the cancerous cell manifests an even more aggressive growth phenotype. If left untreated, metastasis, the spread of cancer cells to distant areas of the body by way of the lymph system or bloodstream, may ensue, destroying healthy tissue.

Cancer metastasis requires that the cancer cells leave the original tumor site, usually by entering the blood or lymphatic system, and spread to other regions of the body. Metastatic cells therefore must become free from the tissues in which they originally developed. This process can involve breakdown of ECM structures.

Arthritis also associated with changes in the ECM. In osteoarthritis, degradation of the ECM of articular cartilage occurs, resulting symptoms such as pain, stiffness, limited motion, tenderness, and swelling.

Changes in the ECM are also associated with cardiovascular diseases such as atherosclerosis, especially in the early stages of the disease.

Thus, new approaches to controlling changes in or degradation of the ECM are desirable.

SUMMARY OF THE INVENTION

We have made the surprising discovery that a soluble polypeptide containing a nonphosphorylatable form of the cytoplasmic domain of membrane type-1 metalloproteinase (MT1-MMP) is capable of inhibiting MT1-MMP activity and that such inhibition does not require either the transmembrane or extracellular portions of the MT1-MMP sequence. The invention therefore features compositions capable of inhibiting MT1-MMP activity, such as soluble polypeptides including the MT1-MMP cytoplasmic sequence with a mutation or deletion at position 573 of the MT1-MMP sequence. MT1-MMP activity has been associated with collagen degradation, with increased motility and invasiveness of cancer cells, and with diseases such as heart disease, vascular disease, and arthritis. Thus, these compositions can be useful in the treatment of these diseases, or any disease where decreased MT1-MMP activity is desirable. Such compositions may also be administered in conjunction with standard therapeutics used to treat these diseases, as described herein.

Accordingly, in a first aspect, the invention features a composition including a polypeptide (e.g., a soluble polypeptide) including an amino acid sequence substantially identical to the cytoplasmic domain of membrane-type 1 matrix metalloproteinase (MT1-MMP) or a fragment thereof, where the polypeptide is capable of inhibiting (e.g., selectively inhibiting) MT1-MMP activity. The amino acid sequence may lack a phosphorylatable tyrosine at the amino acid position corresponding to position 573 of the human MT1-MMP sequence such as a substitution, deletion, or modification at the position 573. In certain embodiments, the substitution made using a naturally occurring amino acid (e.g., phenylalanine), a non-naturally occurring amino acid, or a modified form thereof. The amino acid sequence may have 0, 1, 2, 3, 4, 5, 6, or 7 substitutions as compared to the corresponding sequence of the cytoplasmic domain of human MT1-MMP. In a particular embodiment, the amino acid sequence is at least 80% (e.g., 85%, 90%, 95%, or 98%) identical to the sequence of cytoplasmic domain of human MT1-MMP, or the cytoplasmic domain of human MT1-MMP having a deletion, substitution, or modification at the position corresponding to position 573 of the human MT1-MMP sequence (e.g., RRHGTPRRLL-FCQRSLLDKV (SEQ ID NO:118) or an MT1-MMP inhibitory fragment thereof).

In other embodiments, the polypeptide includes a delivery vector (e.g., an amino acid sequence capable of penetrating a cellular membrane, capable of entering a particular cell type, or capable of crossing the blood-brain barrier (BBB), such as any of those described herein). The amino acid sequence capable of penetrating a cellular membrane may be substantially identical to a polypeptide selected from the group consisting of the third helix of the homeodomain of the antennapedia protein (SEQ ID NO:119, the antennapedia leader peptide (CT) (SEQ ID NO:120), the antennapedia peptide amide (SEQ ID NO:121), Cys(Npys)-antennapedia peptide amide (SEQ ID NO:122), a cytoplasmic transduction peptide (CTP) (e.g., those described herein), HSV-1 VP22, (Arg)$_9$ (SEQ ID NO:137), Cys(Npys)-(Arg)$_9$ (SEQ ID NO:138), Cys(Npys)-(D-Arg)$_9$, [Cys58]105Y cell penetrating peptide (SEQ ID NO:139), peptide 105Y (SEQ ID NO:140), buforin (SEQ ID NO:141), chimeric rabies virus glycoprotein fragment (RVG-9R; SEQ ID NO:142), Cys(Npys)-TAT(47-57) (SEQ ID NO:143), Cys-TAT(47-57) (SEQ ID NO:144), lipid membrane translocating peptide (SEQ ID NO:145), D-isomer-lipid membrane translocating peptide, mastoparan (SEQ ID NO:146), mastoparan 7 (SEQ ID NO:147), mastoparan X (SEQ ID NO:148), MEK 1 derived peptide inhibitor 1 (SEQ ID NO:149), myristoyl-MEK1 derived peptide inhibitor 1 (SEQ ID NO:150), stearyl-MEK-1 derived peptide inhibitor 1 amide (SEQ ID NO:151), membrane-permeable sequence (SEQ ID NO:152), HIV related MPG ((SEQ ID NO:153), aminopeptidase N ligand (CD13), NGR peptide (SEQ ID NO:154), NGR peptide 1, NGR peptide 2 (SEQ ID NO:155), NGR peptide 3 (SEQ ID NO:156), NGR peptide 4, Pep-1 (Chariot™; SEQ ID NO:157), SynB1 (SEQ ID NO:158), biotin-TAT(47-57) (SEQ ID NO:159), TAT(47-57) (SEQ ID NO:160), TAT(47-57) GGG-Cys(Npys) (SEQ ID NO:161), TAT(48-57) (SEQ ID NO:162), Tat-C(48-57) (SEQ ID NO:163), transdermal peptide (SEQ ID NO:164), transportan (SEQ ID NO:165), and transportan 10 (SEQ ID NO:166). In certain embodiments, the polypeptide includes the sequences RQIKIWFQNRRMKWKK (SEQ ID NO:119) and RRHGT-PRRLLFCQRSLLDKV (SEQ ID NO:118) (e.g., the sequence RQIKIWFQNRRMKWKKRRHGTPRRLLFC-QRSLLDKV (SEQ ID NO:176)). In certain embodiments, the amino acid sequence capable of crossing the BBB is an antibody or is at least 90% identical (e.g., 100% identical) to Angiopep-2 (SEQ ID NO:97) or Angiopep-1 (SEQ ID NO:67). The polypeptide may include both Angiopep-2 (SEQ ID NO:97) and the sequence RRHGTPRRLLFCQRSLL-DKV (SEQ ID NO:118) (e.g., the sequence TFFYGGSRGKRNNFKTEEYRRHGT-PRRLLFCQRSLLDKV (SEQ ID NO:178)). In still other embodiments, the amino acid sequence capable of entering a particular cell type is at least 90% identical (e.g., 100% identical) to Angiopep-7 (SEQ ID NO:112).

The composition may be formulated as a liposomal formulation. The liposome may include a delivery vector (e.g., any described herein). The delivery vector may be on the exterior surface of the liposome.

Any of the compositions may be formulated with a pharmaceutically acceptable carrier (e.g., any of those described herein).

In another aspect, the invention features a method of reducing MT1-MMP phosphorylation in a cell. The method includes administering a composition of the above aspect (e.g., any composition described herein) to the cell. The cell may be in a subject (e.g., a human).

In another aspect, the invention features a method of treating (e.g., prophylactically) a disease characterized by increased MT1-MMP activity. The method includes administering a composition of the first aspect (e.g., any composition described herein) to the subject in an amount sufficient to treat the disease (e.g., cancer, heart or vascular disease, or arthritis).

In another aspect, the invention features a method of treating (e.g., prophylactically) a subject having a cancer. The method includes administering a composition of the first aspect (e.g., any composition described herein) to the subject in an amount sufficient to treat the cancer (e.g., a cancer selected from the group consisting of brain cancer, acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia, polycythemia vera, Hodgkin's disease, non-Hodgkin's disease, Waldenstrom's macroglobulinemia, heavy chain disease, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, craniopharyngioma, pinealoma, hemangioblastoma, acoustic neuroma, schwannoma, melanoma, neuroblastoma, retinoblastoma, lung cancer, squamous cell carcinoma, adenocarcinoma, large cell carcinoma, and colon cancer; or a brain cancer selected from the group consisting of glioblastoma, astrocytoma, glioma, meduloblastoma, oligodendroma, neuroglioma, ependymoma, and meningioma).

In another aspect, the invention features a method of treating (e.g., prophylactically) a subject having heart disease or vascular disease. The method includes administering a composition of the first aspect (e.g., any composition described herein) to the subject in an amount sufficient to treat the disease (e.g., where the vascular disease is selected from the group consisting of atherosclerosis, restinosis, abdominal aortic aneurysm, thoracic aortic aneurysm, carotid artery disease, peripheral arterial disease, and renal artery disease or where the heart disease is hypertensive heart disease).

In another aspect, the invention features a method of treating a subject having arthritis. The method includes administering a composition of the first aspect (e.g., any composition described herein) to the subject in an amount sufficient to treat the arthritis (e.g., osteoarthritis, rheumatoid arthritis, or any form of arthritis described herein).

In any of the methods described above, the subject may be a human.

By "MT1-MMP inhibitor" is meant a compound (e.g., a soluble polypeptide or polypeptide mimetic) capable of decreasing (e.g., by at least 1%, 5%, 10%, 15%, 25%, 50%, 75%, 85%, 90%, 9%, 98%, 99%, 99.9%) at least one MT1-MMP activity. MT1-MMP activities include activation of proMMP-2 and degradation of proteins including collagen I, collagen II, collagen III, gelatin, fibronectin, Ln-1, vitronectin, aggrecan, tenascin, nidogen, perlecan, fibrinogen/fibrin, fibrillin, α1PI, α2M, Ln-5, CD44, and tTG. Other MT1-MMP activities are described herein and are known in the art.

By an MT1-MMP inhibitor that "selectively inhibits" is meant an inhibitor that is capable of decreasing at least one MT1-MMP activity (e.g., by binding MT1-MMP), but does not substantially reduce activity of (e.g., does not substantially bind to) other proteins (e.g., other membrane metalloproteinases).

By "delivery vector" is meant a moiety or compound, when attached to a therapeutic, that is capable of increasing transport of the therapeutic across a biological barrier (e.g., across a cell membrane or across the blood-brain barrier), as compared to in the absence of the moiety or compound (e.g., a polypeptide).

By a delivery vector that is "efficiently transported across the BBB" is meant a vector that is able to cross the BBB at least as efficiently as Angiopep-6 (i.e., greater than 38.5% that of Angiopep-1 (250 nM) in the in situ brain perfusion assay described in WO 2008/144919). Accordingly, a vector or conjugate that is "not efficiently transported across the BBB" is transported to the brain at lower levels (e.g., transported less efficiently than Angiopep-6).

By a vector or conjugate which is "efficiently transported to a particular cell type" is meant a vector or conjugate that is able to accumulate (e.g., either due to increased transport into the cell, decreased efflux from the cell, or a combination thereof) in that cell type at least 10% (e.g., 25%, 50%, 100%, 200%, 500%, 1,000%, 5,000%, or 10,000%) greater extent than either a control substance, or, in the case of a conjugate, as compared to the unconjugated agent (e.g., MT1-MMP inhibitor).

By "substantial identity" or "substantially identical" is meant a polypeptide or polynucleotide sequence that has the same polypeptide or polynucleotide sequence, respectively, as a reference sequence, or has a specified percentage of amino acid residues or nucleotides, respectively, that are the same at the corresponding location within a reference sequence when the two sequences are optimally aligned. For example, an amino acid sequence that is "substantially identical" to a reference sequence has at least 50%, 60%, 70%, 75%, 80%, 85%, 90%, 95%, 96%, 97%, 98%, 99%, or 100% identity to the reference amino acid sequence. For polypeptides, the length of comparison sequences will generally be at least 5, 6, 7, 8, 9, 10, 11, 12, 13, 14, 15, 16, 17, 18, 19, 20, 25, 50, 75, 90, 100, 150, 200, 250, 300, or 350 contiguous amino acids (e.g., a full-length sequence). For nucleic acids, the length of comparison sequences will generally be at least 5, 10, 11, 12, 13, 14, 15, 16, 17, 18, 19, 20, 21, 22, 23, 24, or 25 contiguous nucleotides (e.g., the full-length nucleotide sequence). Sequence identity may be measured using sequence analysis software on the default setting (e.g., Sequence Analysis Software Package of the Genetics Computer Group, University of Wisconsin Biotechnology Center, 1710 University Avenue, Madison, Wis. 53705). Such software may match similar sequences by assigning degrees of homology to various substitutions, deletions, and other modifications.

By "substantially pure" or "isolated" is meant a compound (e.g., a polypeptide or conjugate) that has been separated from other chemical components. Typically, the compound is substantially pure when it is at least 30%, by weight, free from other components. In certain embodiments, the preparation is at least 50%, 60%, 75%, 85%, 90%, 95%, 96%, 97%, 98%, or 99% by weight, free from other components. A purified polypeptide may be obtained, for example, by expression of a recombinant polynucleotide encoding such a polypeptide or by chemically synthesizing the polypeptide. Purity can be measured by any appropriate method, for example, column chromatography, polyacrylamide gel electrophoresis, or by HPLC analysis.

By "increased" is meant an increase of at least 5%, 10%, 25%, 25%, 50%, 75%, 100%, 150%, 200%, 500%, or 1000% as compared to a control value.

By "control" is meant a value or amount associated with a healthy or normal subject (e.g., a subject not having a cancer or disease associated with increased MT1-MMP activity).

By "treating" a disease, disorder, or condition in a subject is meant reducing at least one symptom of the disease, disorder, or condition by administrating a therapeutic agent to the subject.

By "treating prophylactically" a disease, disorder, or condition in a subject is meant reducing the frequency of occurrence or severity of a disease, disorder, or condition (e.g., preventing) by administering a therapeutic agent to the subject prior to manifestation of the disease.

By "an effective amount" is meant the amount of a compound, alone or in combination with another therapeutic regimen, required to treat a patient in a clinically relevant manner.

By "subject" is meant a human or non-human animal (e.g., a mammal).

By "vascular disease" is meant any disease associated with changes to the vascular structure. Such diseases include atherosclerosis, restinosis, abdominal aortic aneurysm (AAA), thoracic aortic aneurysm, carotid artery disease, peripheral arterial disease (PAD), and renal artery disease.

Other features and advantages of the invention will be apparent from the following Detailed Description, the drawings, and the claims.

DETAILED DESCRIPTION

Figure 1:
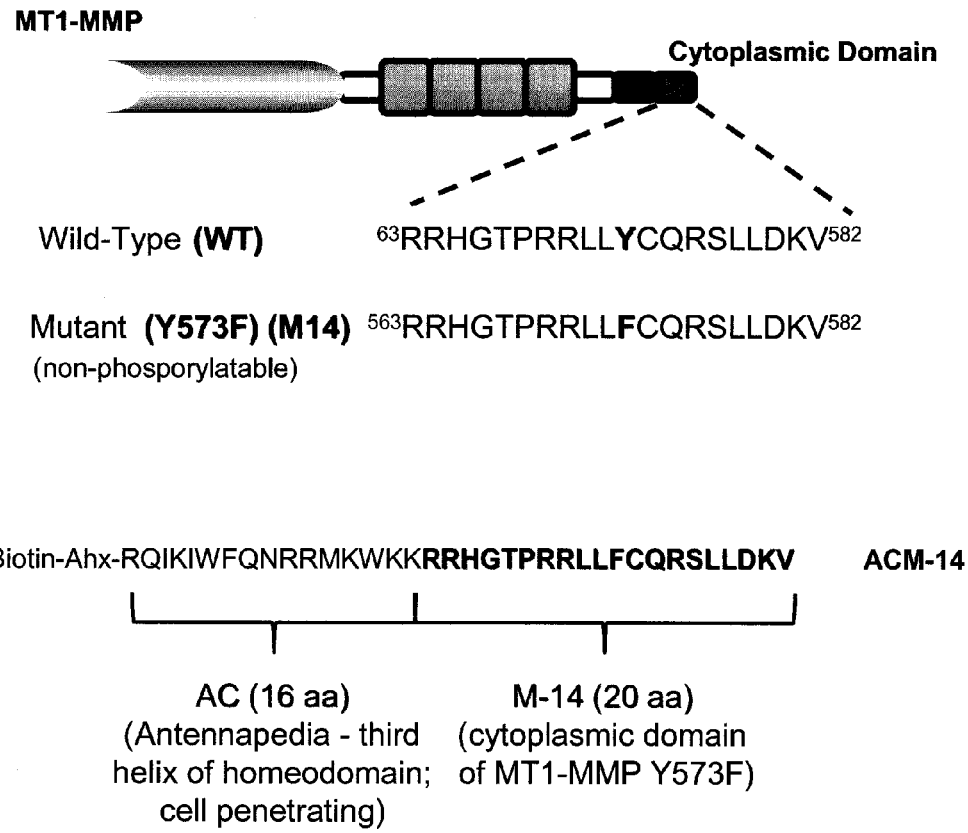
FIG. 1 is a schematic diagram showing the structure of MT1-MMP (SEQ ID NO: 117) and the sequence of the M14 (SEQ ID NO: 118), ACM-14 (SEQ ID NO: 176), and scACM-14SEQ ID NO: 177) polypeptides.

We have discovered that a soluble polypeptide containing a nonphosphorylatable form of the cytoplasmic domain of membrane-type 1 metalloproteinase (MT1-MMP) is capable of inhibiting MT1-MMP activity. As MT1-MMP activity is associated with diseases including cancer, arthritis, fibrosis, and atherosclerosis cells, the MT1-MMP inhibitors described herein can be used in treatment of these diseases.

We have further shown that an MT1-MMP inhibitory polypeptide, when conjugated to a vector capable of delivery the polypeptides to the cytoplasm of cells, is capable of inhibiting cancer growth upon administration to a mammal. Such vectors include the third helix of the homeodomain of the Antennapedia protein, which is capable of penetrating cell membranes. The MT1-MMP polypeptide/antennapedia third helix homeodomain fusion protein inhibits tumor formation and increases survival in mice having cancer tumors, thus providing proof-of-principle that such proteins can be used to treat diseases where decreased MT1-MMP activity is desired, such as cancer, heart and vascular disease, and arthritis.

MT1-MMP and Its Biological Activities

MT1-MMP is a membrane-bound collagenase. Its activities are described, for example, in Itoh et al., J Cell Physiol 206:108, 2006. Increases in MT1-MMP activity are associated with increased degradation of the extracellular matrix and increased cancer invasion, growth, and angiogenesis. MT1-MMP is involved in activation of membrane metalloproteinase-2, which degrades type IV collagen, a component of basement membrane. MT1-MMP is negatively regulated by proteolytic processing, which removes the catalytic domain. This processing results in MT1-MMP downregulation.

Substrates of MT1-MMP include collagen I, collagen II, collagen III, gelatin, fibronectin, Ln-1, vitronectin, aggrecan, tenascin, nidogen, perlecan, fibrinogen/fibrin, fibrillin, α1PI, α2M, Ln-5, CD44, and tTG (see, e.g., Hijova et al., Bratisl Lek Listy 106:127-132, 2005).

MT1-MMP is phosphorylated by Src kinase at $Tyr^{573}$. MT1-MMP phosphorylation is increased in HT-1080 fibrosarcoma cells when stimulated with the chemoattractant sphingosine-1-phosphate (S1P). S1P increases endothelial cell micrgration and differentiation into capillary-like structures.

Further, subcellular localization of phosphorylated MT1-MMP to the cell periphery is induced when the cells are stimulated with S1P. Finally, phosphorylation of MT1-MMP is important growth in 3D collagen matrices and in anchorage-independent growth of tumor cells (Nyalendo et al., Carcinogenesis 29:1655-1664, 2008).

MT1-MMP and Disease

MT1-MMP has been linked to diseases involving degradation of extracellular matrix (ECM) proteins. MT1-MMP activity has, for example, been shown to play important role in tumor cell migration and invasion. MT1-MMP proteolyses ECM proteins (d'Ortho et al., Eur J Biochem 250:751-757, 1997; Hiraoka et al., Cell 95:365-377, 1998; Pei et al., J Biol Chem 271:9135-9140, 1996) as well as a number of cell surface-associated adhesion receptors (Belkin et al., J Biol Chem 276:18415-18422, 2001; Kajita et al., J Cell Biol 153: 893-904, 2001). MT1-MMP is overexpressed in many types of tumors (Nakada et al., Am J Pathol 154, 417-428, 1999; Zhai et al., Cancer Res 65, 6543-6550, 2005) and pericellular proteolysis of the dense cross-linked meshwork of type I collagen fibrils mediated by the enzyme confers neoplastic cells with tissue-invasive activity (Sabeh et al., J Cell Biol 167, 769-781, 2004) and sustains tumor cell growth in otherwise growth-restrictive three-dimensional (3D) matrices (Hotary et al., Cell 114, 33-45, 2003).

MT1-MMP expression has also been linked to arthritis, including osteoarthritis and rheumatoid arthritis. Degradation of ECM proteins, such as collagen, in cartilage, is a feature of arthritis. Elevated levels of MT1-MMP, which can act a collagenase, have been observed in both osteoarthritis (Imai et al., Am J Pathol 151:245-256, 1997) and rheumatoid arthritis (Konttinen et al., Ann Rheum Dis 58:691-697, 1999). MT1-MMP activity is thus believed to play a role in arthritic diseases.

MT1-MMP activity has also been linked to vascular disease. MT1-MMP is expressed in smooth muscle cells and in macrophages in atherosclerotic plaques. MT1-MMP expression is upregulated by proinflammatory molecules in these cells (Tripathi et al., Circulation 99:3103-3109, 1999). As vascular diseases include changes in endothelial cells and smooth muscle structure, MT1-MMP is believed to be involved in the progression of atherosclerosis.

MT1-MMP Inhibitors

The compositions of the invention include an MT1-MMP inhibitor, such as a polypeptide or peptidomimetic capable of inhibiting MT1-MMP activity (e.g., any MT1-MMP activity described herein). In certain embodiments, the polypeptide includes an amino acid sequence substantially identical (e.g., 60%, 70%, 80%, 85%, 90%, 95%, 98%) to the cytoplasmic domain of human MT1-MMP (RRHGTPRRLLYCQRSLL-DKV; SEQ ID NO:117). The polypeptide may have a substitution, modification, or deletion at the tyrosine at the position corresponding to position 573 of the human MT1-MMP sequence. The tyrosine may be substituted with any naturally occurring amino acid (e.g., Ala, Arg, Asn, Asp, Cys, Gln, Glu, Gly, His, Ile, Leu, Lys, Met, Phe, Pro, Ser, Thr, Trp, and Val), a non-naturally occurring amino acid, or a modified form thereof. In certain embodiments, the tyrosine is substituted with a phenylalanine (e.g., RRHGTPRRLLFCQRSLLDKV; SEQ ID NO:118). In other embodiments, the tyrosine is substituted with a tyrosine analog. Exemplary tyrosine analogs are described in U.S. Pat. No. 6,469,047 and in PCT Publication WO 2002/085923 (e.g., FIG. 26).

In other embodiments, the MT1-MMP inhibitor polypeptide includes an amino acid sequence substantially identical to a fragment of the MT1-MMP cytoplasmic domain. The fragment may have a substitution, modification, or deletion at the $Tyr^{573}$ of the human MT1-MMP sequence (e.g., those described herein). In certain embodiments, the fragment has 0, 1, 2, 3, 4, 5, 6, 7, 8, 9, 10, 11, 12, 13, 14, or 15 amino acids deleted from the N-terminus of the MT1-MMP cytoplasmic domain, 0, 1, 2, 3, 4, 5, 6, 7, 8, 9, 10, 11, 12, 13, 14, or 15 amino acids deleted from the C-terminus of the MT1-MMP cytoplasmic domain, or a combination thereof. In certain embodiments, the fragment contains an amino acid at the position corresponding to residue 573 of the human MT1-MMP sequence.

Any of the MT1-MMP inhibitory polypeptides may have 0, 1, 2, 3, 4, 5, 6, or 7 substitutions (e.g., conservative or nonconservative) as compared to the human wild-type sequence. In certain embodiments, the polypeptide may be a peptidomimetic (e.g., those described herein).

Delivery Vectors

The MT1-MMP inhibitory therapeutics described herein may be present in conjunction with a delivery vector capable of enhancing delivery of the therapeutic to target cell(s), or to improve transport of the therapeutic across a biological barrier such as the blood-brain barrier (BBB). Delivery vectors include cell-penetrating peptides, peptides capable of being transported across the BBB, and liposomes capable of enhancing delivery to particular cell types. In certain embodiments, a polypeptide delivery vector forms a fusion protein with the MT1-MMP inhibitor. In other embodiments, the delivery vector is chemically conjugated to the MT1-MMP inhibitor.

Cell Penetrating Peptide Vectors

In certain embodiments, the delivery vector is a cell penetrating peptide. Such peptides are capable, upon couple of the cell penetrating peptide to the therapeutic, of delivering the therapeutic across the cell membrane. In certain embodiments, the cell penetrating peptide is the third helix of the homeodomain of the antennapedia protein (RQIKIWFQNR-RMKWKK; SEQ ID NO:119)), or a related peptide (e.g., antennapedia leader peptide (CT) (KKWKMRRNQF-WVKVQRG; SEQ ID NO:120), antennapedia peptide amide (RQIKIWFQNRRMKWKK-$NH_2$; SEQ ID NO:121), and Cys(Npys)-antennapedia peptide amide (C(Npys)-RQIKIW-FQNRRMKWKK-$NH_2$: SEQ ID NO:122).

In certain embodiments, the peptide is a cytoplasmic transduction peptide (CTP). Such peptides are described in U.S. Pat. No. 7,101,844 and include the amino acid sequences YGRRARRRRRR (SEQ ID NO:123), YGRRARRRARR (SEQ ID NO:124), YGRRARRRARR (SEQ ID NO:125), YKRKARRAARR (SEQ ID NO:126), YARKARRAARR (SEQ ID NO:127), YKRAARRAARR (SEQ ID NO:128), YEREARRAARR (SEQ ID NO:129), YAREARRAARR (SEQ ID NO:130), YGRAARRAARR (SEQ ID NO:131), YRRAARRAARA (SEQ ID NO:132), YPRAARRAARR (SEQ ID NO:133), PARAARRAARR (SEQ ID NO:134), YGRRRRRRRRR (SEQ ID NO:135), and YRRRRRRRRRR (SEQ ID NO:136).

In other embodiments, the peptide is HSV-1 VP22, $(Arg)_9$ (SEQ ID NO:137), Cys(Npys)-$(Arg)_9$ (SEQ ID NO:138), Cys(Npys)-(D-Arg)$_9$, [$Cys^{58}$]105Y cell penetrating peptide (CSIPPEVKFNKPFVYLI; SEQ ID NO:139), peptide 105Y (SIPPEVKFNKPFVYLI; SEQ ID NO:140), buforin (TRSS-RAGLQFPVGRVHRLLRK; SEQ ID NO:141), chimeric rabies virus glycoprotein fragment (RVG-9R) (YTIW-MPENPRPGTPCDIFTNSRGKRAS-NGGGGRRRRRRRRR; SEQ ID NO:142), Cys(Npys)-TAT (47-57) (C(Npys)YGRKKRRQRRR-$NH_2$; SEQ ID NO:143), Cys-TAT(47-57) (CYGRKKRRQRRR-$NH_2$; SEQ ID NO:144), lipid membrane translocating peptide (KKAAAVLLPVLLAAP; SEQ ID NO:145), D-isomer-lipid membrane translocating peptide ("All D" KKAAAVLLPV-LLAAP), mastoparan (INLKALAALAKKIL-NH$_2$; SEQ ID NO:146), mastoparan 7 (INLKALAALAKALL-NH$_2$; SEQ ID NO:147), mastoparan X (INWKGIAAMAKKLL-NH$_2$; SEQ ID NO:148), MEK1 derived peptide inhibitor I (MP-KKKPTPIQLNP; SEQ ID NO:149), myristoyl-MEK1 derived peptide inhibitor 1 (Myr-MPKKKPTPIQLNP; SEQ ID NO:150), stearyl-MEK-1 derived peptide inhibitor 1 amide (Ste-MPKKKPTPIQLNP-NH$_2$; SEQ ID NO:151), membrane-permeable sequence (MPS; AAVALLPAVLLAL-LAK; SEQ ID NO:152), HIV related MPG (GALFLGFL-GAAGSTMGAWSQPKSKRKV; SEQ ID NO:153), aminopeptidase N ligand (CD13), NGR peptide (CNGRCG, Cys1-Cys5 disulfide bridge; SEQ ID NO:154), NGR peptide 1 (Cys-Asn-Gly-Arg-Cys-Gly-Gly-D-Lys-D-Leu-D-Ala-D-Lys-D-Leu-D-Ala-D-Lys-D-Lys-D-Leu-D-Ala-D-Lys-D-Leu-D-Ala-D-Lys-NH$_2$ (Disulfide bridge: 1-5)), NGR peptide 2 (CNGRCGGLVTT (disulfide bridge: 1-5); SEQ ID NO:155), NGR peptide 3 (CNGRC-NH$_2$ (Disulfide bridge: 1-5); SEQ ID NO:156), NGR peptide 4 (Cys-Asn-Gly-Arg-Cys-Gly-Gly-D-Lys-D-Lys-D-Leu-D-Lys-D-Leu-D-Leu-D-Leu-D-Lys-D-Leu-D-Leu-OH (Disulfide bridge: 1-5)), Pep-1 (Chariot™; KETWWETWWTEWSQPKKKRKV; SEQ ID NO:157), SynB1 (RGGRLSYSRRRFSTSTGRA; SEQ ID NO:158), biotin-TAT(47-57) (biotin-YGRKKRRQRRR; SEQ ID NO:159), TAT(47-57) (YGRKKRRQRRR; SEQ ID NO:160), TAT(47-57) GGG-Cys(Npys) (YGRKKRRQRRRGGG-C(Npys)-NH$_2$; SEQ ID NO:161), TAT(48-57) (GRKKRRQRRR; SEQ ID NO:162), Tat-C(48-57) (CGRKKRRQRRR; SEQ ID NO:163), transdermal peptide (ACSSSPSKHCG; SEQ ID NO:164), transportan (GWTLNSAGYLLGKINLKA-LAALAKKIL; SEQ ID NO:165), and transportan 10 (AGYLLGKINLKALAALAKKIL-NH$_2$; SEQ ID NO:166).

Polypeptide Vectors Capable of Entering or Accumulating in Cells

We have developed polypeptides capable of entering and accumulating in cells types such as liver, lungs, kidneys, spleen, and muscle. See, e.g., PCT Publication WO 2008/144919. Such peptides include Angiopep-7 (TFFYGGSR-GRRNNFRTEEY; SEQ ID NO:112), which is capable of entering these cell types, but does not efficiently cross the blood-brain barrier. Other peptides capable of entering and accumulating in these cell types include the Angiopep peptides described below, which also cross the BBB.

In certain embodiments, the polypeptide includes an amino acid sequence substantially identical to Angiopep-7. The polypeptide may include a sequence having 0, 1, 2, 3, 4, 5, 6, 7, 8, 9, or 10 amino acid substitutions as compared to the Angiopep-7 sequence, or may be a fragment of Angiopep-7 (e.g., a fragment capable of accumulating in at least cell type selected from the group consisting of liver, lung, spleen, muscle, or pancreas). In certain embodiments, the Angiopep-7 polypeptide may include either an N-terminal or a C-terminal cysteine residue (e.g., CTFFYGGSRGRRNNFR-TEEY (SEQ ID NO:115) and TFFYGGSRGRRNNFR-TEEYC (SEQ ID NO:116)).

In certain embodiments, the polypeptide includes an amino acid sequence having the formula:

X1-X2-X3-X4-X5-X6-X7-X8-X9-X10-X11-X12-X13-X14-X15-X16-X17-X18-X19 where each of X1-X19 (e.g., X1-X6, X8, X9, X11-X14, and X16-X19) is, independently, any amino acid (e.g., a naturally occurring amino acid such as Ala, Arg, Asn, Asp, Cys, Gln, Glu, Gly, His, Ile, Leu, Lys, Met, Phe, Pro, Ser, Thr, Trp, Tyr, and Val) or absent and at least one (e.g., 2 or 3) of X1, X10, and X15 is arginine. In some embodiments, X7 is Ser or Cys; or X10 and X15 each are independently Arg or Lys. In some embodiments, the residues from X1 through X19, inclusive, are substantially identical to any of the amino acid sequences of any one of SEQ ID NOS:1-105 and 107-116 (e.g., Angiopep-1, Angiopep-2, Angiopep-3, Angiopep-4a, Angiopep-4b, Angiopep-5, Angiopep-6, and Angiopep-7). In some embodiments, at least one (e.g., 2, 3, 4, or 5) of the amino acids X1-X19 is Arg. In some embodiments, the polypeptide has one or more additional cysteine residues at the N-terminal of the polypeptide, the C-terminal of the polypeptide, or both. The polypeptide may be capable of accumulating in particular cell types, and may (or may not) efficiently cross the BBB.

Delivery Vectors Capable of Crossing the Blood-Brain Barrier

In certain embodiments, the therapeutic is attached to a delivery vector capable of crossing the blood-brain barrier. Such polypeptides include the aprotinin-derived Angiopep series of peptides and analogs thereof, including aprotinin (e.g., as described in U.S. Patent Application No. 2006/0189515), antibodies, and others described herein.

Angiopep Peptides

In certain embodiments, the therapeutic is attached to a polypeptide substantially identical to any of the sequences set Table 1, or a fragment thereof. Particular examples of such polypeptides are those having the sequence of Angiopep-1 (SEQ ID NO:67), Angiopep-2 (SEQ ID NO:97), Angiopep-3 (SEQ ID NO:107), Angiopep-4a (SEQ ID NO:108), Angiopep-4b (SEQ ID NO:109), Angiopep-5 (SEQ ID NO:110), or Angiopep-6 (SEQ ID NO:111). The peptide vector may be of any length, for example, at least 6, 7, 8, 9, 10, 11, 12, 13, 14, 15, 16, 17, 18, 19, 20, 21, 25, 35, 50, 75, 100, 200, or 500 amino acids, or any range between these numbers. In certain embodiments, the peptide vector is 10 to 50 amino acids in length. The polypeptide may be produced by recombinant genetic technology or chemical synthesis. The polypeptide may contain a C-terminal cysteine, an N-terminal cysteine, or both.

TABLE 1

Exemplary Polypeptides

| SEQ ID NO: | | | | | | | | | | | | | | | | | | | |
|---|---|---|---|---|---|---|---|---|---|---|---|---|---|---|---|---|---|---|---|
| 1 | T | F | V | Y | G | G | C | R | A | K | R | N | N | F | K | S | A | E | D |
| 2 | T | F | Q | Y | G | G | C | M | G | N | G | N | N | F | V | T | E | K | E |
| 3 | P | F | F | Y | G | G | C | G | G | N | R | N | N | F | D | T | E | E | Y |
| 4 | S | F | Y | Y | G | G | C | L | G | N | K | N | N | Y | L | R | E | E | E |
| 5 | T | F | F | Y | G | G | C | R | A | K | R | N | N | F | K | R | A | K | Y |
| 6 | T | F | F | Y | G | G | C | R | G | K | R | N | N | F | K | R | A | K | Y |
| 7 | T | F | F | Y | G | G | C | R | A | K | K | N | N | Y | K | R | A | K | Y |
| 8 | T | F | F | Y | G | G | C | R | G | K | K | N | N | F | K | R | A | K | Y |
| 9 | T | F | Q | Y | G | G | C | R | A | K | R | N | N | F | K | R | A | K | Y |
| 10 | T | F | Q | Y | G | G | C | R | G | K | K | N | N | F | K | R | A | K | Y |
| 11 | T | F | F | Y | G | G | C | L | G | K | R | N | N | F | K | R | A | K | Y |
| 12 | T | F | F | Y | G | G | S | L | G | K | R | N | N | F | K | R | A | K | Y |

TABLE 1 -continued

Exemplary Polypeptides

| SEQ ID NO: | |
|---|---|
| 13 | P F F Y G G C G G K K N N F K R A K Y |
| 14 | T F F Y G G C R G K G N N Y K R A K Y |
| 15 | P F F Y G G C R G K R N N F L R A K Y |
| 16 | T F F Y G G C R G K R N N F K R E K Y |
| 17 | P F F Y G G C R A K K N N F K R A K E |
| 18 | T F F Y G G C R G K R N N F K R A K D |
| 19 | T F F Y G G C R A K R N N F D R A K Y |
| 20 | T F F Y G G C R G K K N N F K R A E Y |
| 21 | P F F Y G G C G A N R N N F K R A K Y |
| 22 | T F F Y G G C G G K K N N F K T A K Y |
| 23 | T F F Y G G C R G N R N N F L R A K Y |
| 24 | T F F Y G G C R G N R N N F K T A K Y |
| 25 | T F F Y G G S R G N R N N F K T A K Y |
| 26 | T F F Y G G C L G N G N N F K R A K Y |
| 27 | T F F Y G G C L G N R N N F L R A K Y |
| 28 | T F F Y G G C L G N R N N F K T A K Y |
| 29 | T F F Y G G C R G N G N N F K S A K Y |
| 30 | T F F Y G G C R G K K N N F D R E K Y |
| 31 | T F F Y G G C R G K R N N F L R E K E |
| 32 | T F F Y G G C R G K G N N F D R A K Y |
| 33 | T F F Y G G S R G K G N N F D R A K Y |
| 34 | T F F Y G G C R G N G N N F V T A K Y |
| 35 | P F F Y G G C G G K G N N Y V T A K Y |
| 36 | T F F Y G G C L G K G N N F L T A K Y |
| 37 | S F F Y G G C L G N K N N F L T A K Y |
| 38 | T F F Y G G C G G N K N N F V R E K Y |
| 39 | T F F Y G G C M G N K N N F V R E K Y |
| 40 | T F F Y G G S M G N K N N F V R E K Y |
| 41 | P F F Y G G C L G N R N N Y V R E K Y |
| 42 | T F F Y G G C L G N R N N F V R E K Y |
| 43 | T F F Y G G C L G N K N N Y V R E K Y |
| 44 | T F F Y G G C G G N G N N F L T A K Y |
| 45 | T F F Y G G C R G N R N N F L T A E Y |
| 46 | T F F Y G G C R G N G N N F K S A E Y |
| 47 | P F F Y G G C L G N K N N F K T A E Y |
| 48 | T F F Y G G C R G N R N N F K T E E Y |
| 49 | T F F Y G G C R G K R N N F K T E E D |
| 50 | P F F Y G G C G G N G N N F V R E K Y |
| 51 | S F F Y G G C M G N G N N F V R E K Y |
| 52 | P F F Y G G C G G N G N N F L R E K Y |
| 53 | T F F Y G G C L G N G N N F V R E K Y |
| 54 | S F F Y G G C L G N G N N Y L R E K Y |
| 55 | T F F Y G G S L G N G N N F V R E K Y |
| 56 | T F F Y G G C R G N G N N F V T A E Y |
| 57 | T F F Y G G C L G K G N N F V S A E Y |
| 58 | T F F Y G G C L G N R N N F D R A E Y |
| 59 | T F F Y G G C L G N R N N F L R E E Y |
| 60 | T F F Y G G C L G N K N N Y L R E E Y |
| 61 | P F F Y G G C G G N R N N Y L R E E Y |
| 62 | P F F Y G G S G G N R N N Y L R E E Y |
| 63 | M R P D F C L E P P Y T G P C V A R I |
| 64 | A R I I R Y F Y N A K A G L C Q T F V Y G |
| 65 | Y G G C R A K R N N Y K S A E D C M R T C G |
| 66 | P D F C L E P P Y T G P C V A R I I R Y F Y |
| 67 | T F F Y G G C R G K R N N F K T E E Y |
| 68 | K F F Y G G C R G K R N N F K T E E Y |
| 69 | T F Y Y G G C R G K R N N Y K T E E Y |
| 70 | T F F Y G G S R G K R N N F K T E E Y |
| 71 | C T F F Y G C C R G K R N N F K T E E Y |
| 72 | T F F Y G G C R G K R N N F K T E E Y C |
| 73 | C T F F Y G S C R G K R N N F K T E E Y |
| 74 | T F F Y G G S R G K R N N F K T E E Y C |
| 75 | P F F Y G G C R G K R N N F K T E E Y |
| 76 | T F F Y G G C R G K R N N F K T K E Y |
| 77 | T F F Y G G K R G K R N N F K T E E Y |
| 78 | T F F Y G G C R G K R N N F K T K R Y |
| 79 | T F F Y G G K R G K R N N F K T A E Y |
| 80 | T F F Y G G K R G K R N N F K T A G Y |
| 81 | T F F Y G G K R G K R N N F K R E K Y |
| 82 | T F F Y G G K R G K R N N F K R A K Y |
| 83 | T F F Y G G C L G N R N N F K T E E Y |
| 84 | T F F Y G C C R G K R N N F K T E E Y |
| 85 | T F F Y G G R C G K R N N F K T E E Y |
| 86 | T F F Y G G C L G N G N N F D T E E E |

TABLE 1 -continued

Exemplary Polypeptides

| SEQ ID NO: | |
|---|---|
| 87 | T F Q Y G G C R G K R N N F K T E E Y |
| 88 | Y N K E F G T F N T K G C E R G Y R F |
| 89 | R F K Y G G C L G N M N N F E T L E E |
| 90 | R F K Y G G C L G N K N N F L R L K Y |
| 91 | R F K Y G G C L G N K N N Y L R L K Y |
| 92 | K T K R K R K K Q R V K I A Y E E I F K N Y |
| 93 | K T K R K R K K Q R V K I A Y |
| 94 | R G G R L S Y S R R F S T S T G R |
| 95 | R R L S Y S R R R F |
| 96 | R Q I K I W F Q N R R M K W K K |
| 97 | T F F Y G G S R G K R N N F K T E E Y |
| 98 | M R P D F C L E P P Y T G P C V A R I I R Y F Y N A K A G L C Q T F V Y G G C R A K R N N F K S A E D C M R T C G G A |
| 99 | T F F Y G G C R G K R N N F K T K E Y |
| 100 | R F K Y G G C L G N K N N Y L R L K Y |
| 101 | T F F Y G G C R A K R N N F K R A K Y |
| 102 | N A K A G L C Q T F V Y G G C L A K R N N F E S A E D C M R T C G G A |
| 103 | Y G G C R A K R N N F K S A E D C M R T C G G A |
| 104 | G L C Q T F V Y G G C R A K R N N F K S A E |
| 105 | L C Q T F V Y G G C E A K R N N F K S A |
| 107 | T F F Y G G S R G K R N N F K T E E Y |
| 108 | R F F Y G G S R G K R N N F K T E E Y |
| 109 | R F F Y G G S R G K R N N F K T E E Y |
| 110 | R F F Y G G S R G K R N N F R T E E Y |
| 111 | T F F Y G G S R G K R N N F R T E E Y |
| 113 | C T F F Y G G S R G K R N N F K T E E Y |
| 114 | T F F Y G G S R G K R N N F K T E E Y C |

Polypeptides Nos. 5, 67, 76, and 91, include the sequences of SEQ ID NOS: 5, 67, 76, and 91, respectively, and are amidated at the C-terminus.
Polypeptides Nos. 107, 109, and 110 include the sequences of SEQ ID NOS: 97, 109, and 110, respectively, and are acetylated at the N-terminus.

In certain embodiments, the Angiopep polypeptide is capable of efficiently crossing the BBB and includes an amino acid sequence having the formula:

X1-X2-X3-X4-X5-X6-X7-X8-X9-X10-X11-X12-X13-X14-X15-X16-X17-X18-X19 where each of X1-X19 (e.g., X1-X6, X8, X9, X11-X14, and X16-X19) is, independently, any amino acid (e.g., a naturally occurring amino acid such as Ala, Arg, Asn, Asp, Cys, Gln, Glu, Gly, His, Ile, Leu, Lys, Met, Phe, Pro, Ser, Thr, Trp, Tyr, and Val) or absent and at least one (e.g., 2 or 3) of X1, X10, and X15 is arginine. In some embodiments, X7 is Ser or Cys; or X10 and X15 each are independently Arg or Lys. In some embodiments, the residues from X1 through X19, inclusive, are substantially identical to any of the amino acid sequences of any one of SEQ ID NOS:1-105 and 107-116 (e.g., Angiopep-1, Angiopep-2, Angiopep-3, Angiopep-4a, Angiopep-4b, Angiopep-5, Angiopep-6, and Angiopep-7). In some embodiments, at least one (e.g., 2, 3, 4, or 5) of the amino acids X1-X19 is Arg. In some embodiments, the polypeptide has one or more additional cysteine residues at the N-terminal of the polypeptide, the C-terminal of the polypeptide, or both.

Antibodies

In certain embodiments, an antibody or antibody fragment that binds a receptor capable of mediating transcytosis across the BBB is used as a delivery vector to transport the MT1-MMP inhibitor across the BBB. Following binding to the receptor, the antibody can be transported across the BBB.

Accordingly, such antibodies can be used to transport agents across the BBB, when the agent is conjugated to, or otherwise associated with, such an antibody. These antibodies include anti-insulin receptor antibodies (described in U.S. Patent Application Publication No. 2004/0101904), anti-transferrin receptor antibodies (described in Pardridge et al., Pharmacol. Exp. Ther. 256:66-70, 1991).

Additional antibodies targeted to receptors capable of mediating transcytosis can be generated using methods well known in the art. In certain embodiments, the antibodies are human or are humanized.

Other Peptides

Other peptides capable of crossing the BBB that can be used as delivery vectors include rabies virus glycoprotein (RVG; YTIWMPENPRPGTPCDIFTNSRGKRASNG; SEQ ID NO:167), p97, transferrin, insulin, receptor-associated protein (RAP), tissue-type plasminogen activator (tPA), and lactoferrin. LRP ligands, insulin-like growth factor (IGF), leptin, low density lipoprotein (LDL), which may be capable of crossing the BBB, are also described in U.S. Patent Application Publication Nos. 2003/0129186 and 2004/0102369. Still other peptides, such as the H.8 region of the *Neisseria gonorrhoeae* F62 Laz protein (CSQEPAAPAAEATPAGEA-PASEAPAAEAAPADAAEAPAA; SEQ ID NO:168) or peptides having at least 4 perfect or imperfect AAEAP repeats are described U.S. Patent Application Publication No. 2008/0213185. Such peptides are capable of crossing the BBB.

Still other polypeptides include Kunitz domain-containing polypeptides, such as aprotinin, bikunin, amyloid beta precursor protein, and Kunitz inhibitor proteins.

Liposomal Delivery Systems

The MT1-MMP inhibitor can also be delivered to particular tissues using liposomes. In certain embodiments, the MT1-MMP inhibitory therapeutic (e.g., a polypeptide) is delivered to target cells using an immunoliposomes. In this approach, the polypeptide is encapsulated in a liposome (e.g., any suitable liposome known in the art), where the liposome is conjugated on its exterior surface to an antibody capable of binding to a antigen expressed on the target cell. In one example, the immunoliposome targeted to a cancer cell. Such immunoliposomes can use anti-EGF receptor antibodies (e.g., as described in Mamot et al., Cancer Res 63:3154-61, 2003), anti-HER2 antibodies (e.g., as described in Kirpotin et al., Biochemistry, 36:66-75, 1997 and in Park et al., Proc Natl Acad Sci USA 92:1327-1331, 1995), anti-MUC1 antibodies (e.g., as described in Moase et al., Biochim Biophys Acta 1510:43-55, 2001), anti-CC52 antibodies (Kamps et al., J Drug Target 8:235-45, 2000), antiganglioside G(M3) antibodies (DH2) or anti-Le(x) antibodies (SH1) (e.g., as described in Nam et al., Oncol Res 11:9-16, 1999).

Delivery across the BBB can also be accomplished similarly. For example, a liposome containing an MT1-MMP inhibitor can be conjugated to an antibody directed to a receptor capable of mediating transcytosis across the BBB. Such antibodies are described above and include anti-transferrin receptor antibodies and anti-insulin receptor antibodies.

Polypeptide Derivatives and Peptidomimetics

In addition to polypeptides consisting of naturally occurring amino acids, peptidomimetics or polypeptide analogs are also encompassed by the present invention and can form the delivery vectors or MT1-MMP inhibitors used in the compositions of the invention. Polypeptide analogs are commonly used in the pharmaceutical industry as non-peptide drugs with properties analogous to those of the template polypeptide. The non-peptide compounds are termed "peptide mimetics" or peptidomimetics (Fauchere et al., Infect. Immun. 54:283-287,1986 and Evans et al., J. Med. Chem. 30:1229-1239, 1987). Peptide mimetics that are structurally related to therapeutically useful peptides or polypeptides may be used to produce an equivalent or enhanced therapeutic or prophylactic effect. Generally, peptidomimetics are structurally similar to the paradigm polypeptide (i.e., a polypeptide that has a biological or pharmacological activity) such as naturally-occurring receptor-binding polypeptides, but have one or more peptide linkages optionally replaced by linkages such as —CH$_2$NH—, —CH$_2$S—, —CH═CH— (cis and trans), —CH$_2$SO—, —CH(OH)CH$_2$—, —COCH$_2$— etc., by methods well known in the art (Spatola, Peptide Backbone Modifications, Vega Data, 1:267, 1983; Spatola et al., Life Sci. 38:1243-1249, 1986; Hudson et al., Int. J. Pept. Res. 14:177-185, 1979; and Weinstein, 1983, Chemistry and Biochemistry, of Amino Acids, Peptides and Proteins, Weinstein eds, Marcel Dekker, New York). Such polypeptide mimetics may have significant advantages over naturally occurring polypeptides including more economical production, greater chemical stability, enhanced pharmacological properties (e.g., half-life, absorption, potency, efficiency), reduced antigenicity, and others.

While the peptide vectors described herein may efficiently cross the BBB or target particular cell types (e.g., those described herein), their effectiveness may be reduced by the presence of proteases. Likewise, the effectiveness of MT1-MMP inhibitors used in the invention may be similarly reduced. Serum proteases have specific substrate requirements, including L-amino acids and peptide bonds for cleavage. Furthermore, exopeptidases, which represent the most prominent component of the protease activity in serum, usually act on the first peptide bond of the polypeptide and require a free N-terminus (Powell et al., Pharm. Res. 10:1268-1273, 1993). In light of this, it is often advantageous to use modified versions of polypeptides. The modified polypeptides retain the structural characteristics of the original L-amino acid polypeptides, but advantageously are not readily susceptible to cleavage by protease and/or exopeptidases.

Systematic substitution of one or more amino acids of a consensus sequence with D-amino acid of the same type (e.g., an enantiomer; D-lysine in place of L-lysine) may be used to generate more stable polypeptides. Thus, a polypeptide derivative or peptidomimetic as described herein may be all L-, all D-, or mixed D, L polypeptides. The presence of an N-terminal or C-terminal D-amino acid increases the in vivo stability of a polypeptide because peptidases cannot utilize a D-amino acid as a substrate (Powell et al., Pharm. Res. 10:1268-1273, 1993). Reverse-D polypeptides are polypeptides containing D-amino acids, arranged in a reverse sequence relative to a polypeptide containing L-amino acids. Thus, the C-terminal residue of an L-amino acid polypeptide becomes N-terminal for the D-amino acid polypeptide, and so forth. Reverse D-polypeptides retain the same tertiary conformation and therefore the same activity, as the L-amino acid polypeptides, but are more stable to enzymatic degradation in vitro and in vivo, and thus have greater therapeutic efficacy than the original polypeptide (Brady and Dodson, Nature 368:692-693, 1994; Jameson et al., Nature 368:744-746, 1994). In addition to reverse-D-polypeptides, constrained polypeptides comprising a consensus sequence or a substantially identical consensus sequence variation may be generated by methods well known in the art (Rizo et al., Ann. Rev. Biochem. 61:387-418, 1992). For example, constrained polypeptides may be generated by adding cysteine residues capable of forming disulfide bridges and, thereby, resulting in a cyclic polypeptide. Cyclic polypeptides have no free N- or C-termini. Accordingly, they are not susceptible to proteolysis by exopeptidases, although they are, of course, susceptible to endopeptidases, which do not cleave at polypeptide termini. The amino acid sequences of the polypeptides with N-terminal or C-terminal D-amino acids and of the cyclic polypeptides are usually identical to the sequences of the polypeptides to which they correspond, except for the presence of N-terminal or C-terminal D-amino acid residue, or their circular structure, respectively.

A cyclic derivative containing an intramolecular disulfide bond may be prepared by conventional solid phase synthesis while incorporating suitable S-protected cysteine or homocysteine residues at the positions selected for cyclization such as the amino and carboxy termini (Sah et al., J. Pharm. Pharmacol. 48:197, 1996). Following completion of the chain assembly, cyclization can be performed either (1) by selective removal of the S-protecting group with a consequent on-support oxidation of the corresponding two free SH-functions, to form a S—S bonds, followed by conventional removal of the product from the support and appropriate purification procedure or (2) by removal of the polypeptide from the support along with complete side chain de-protection, followed by oxidation of the free SH-functions in highly dilute aqueous solution.

The cyclic derivative containing an intramolecular amide bond may be prepared by conventional solid phase synthesis while incorporating suitable amino and carboxyl side chain protected amino acid derivatives, at the position selected for cyclization. The cyclic derivatives containing intramolecular —S-alkyl bonds can be prepared by conventional solid phase chemistry while incorporating an amino acid residue with a suitable amino-protected side chain, and a suitable S-protected cysteine or homocysteine residue at the position selected for cyclization.

Another effective approach to confer resistance to peptidases acting on the N-terminal or C-terminal residues of a polypeptide is to add chemical groups at the polypeptide termini, such that the modified polypeptide is no longer a substrate for the peptidase. One such chemical modification is glycosylation of the polypeptides at either or both termini. Certain chemical modifications, in particular N-terminal glycosylation, have been shown to increase the stability of polypeptides in human serum (Powell et al., Pharm. Res. 10:1268-1273, 1993). Other chemical modifications which enhance serum stability include, but are not limited to, the addition of an N-terminal alkyl group, consisting of a lower alkyl of from one to twenty carbons, such as an acetyl group, and/or the addition of a C-terminal amide or substituted amide group. In particular, the present invention includes modified polypeptides consisting of polypeptides bearing an N-terminal acetyl group and/or a C-terminal amide group.

Also included by the present invention are other types of polypeptide derivatives containing additional chemical moieties not normally part of the polypeptide, provided that the derivative retains the desired functional activity of the polypeptide. Examples of such derivatives include (1) N-acyl derivatives of the amino terminal or of another free amino group, wherein the acyl group may be an alkanoyl group (e.g., acetyl, hexanoyl, octanoyl) an aroyl group (e.g., benzoyl) or a blocking group such as F-moc (fluorenylmethyl-O—CO—); (2) esters of the carboxy terminal or of another free carboxy or hydroxyl group; (3) amide of the carboxy-terminal or of another free carboxyl group produced by reaction with ammonia or with a suitable amine; (4) phosphorylated derivatives; (5) derivatives conjugated to an antibody or other biological ligand and other types of derivatives.

Longer polypeptide sequences which result from the addition of additional amino acid residues to the polypeptides described herein are also encompassed in the present invention. Such longer polypeptide sequences can be expected to have the same biological activity and specificity (e.g., cell tropism) as the polypeptides described above. While polypeptides having a substantial number of additional amino acids are not excluded, it is recognized that some large polypeptides may assume a configuration that masks the effective sequence, thereby preventing binding to a target. These derivatives could act as competitive antagonists. Thus, while the present invention encompasses polypeptides or derivatives of the polypeptides described herein having an extension, desirably the extension does not destroy the cell targeting activity of the polypeptides or its derivatives.

Other derivatives included in the present invention are dual polypeptides consisting of two of the same, or two different polypeptides, as described herein, covalently linked to one another either directly or through a spacer, such as by a short stretch of alanine residues or by a putative site for proteolysis (e.g., by cathepsin, see e.g., U.S. Pat. No. 5,126,249 and European Patent No. 495 049). Multimers of the polypeptides described herein consist of a polymer of molecules formed from the same or different polypeptides or derivatives thereof.

The present invention also encompasses polypeptide derivatives that are chimeric or fusion proteins containing a polypeptide described herein, or fragment thereof, linked at its amino- or carboxy-terminal end, or both, to an amino acid sequence of a different protein. Such a chimeric or fusion protein may be produced by recombinant expression of a nucleic acid encoding the protein. For example, a chimeric or fusion protein may contain at least 6 amino acids shared with one of the described polypeptides which desirably results in a chimeric or fusion protein that has an equivalent or greater functional activity.

Assays to Identify Peptidomimetics

As described above, non-peptidyl compounds generated to replicate the backbone geometry and pharmacophore display (peptidomimetics) of the polypeptides described herein often possess attributes of greater metabolic stability, higher potency, longer duration of action, and better bioavailability.

Peptidomimetics compounds can be obtained using any of the numerous approaches in combinatorial library methods known in the art, including biological libraries, spatially addressable parallel solid phase or solution phase libraries, synthetic library methods requiring deconvolution, the 'one-bead one-compound' library method, and synthetic library methods using affinity chromatography selection. The biological library approach is limited to peptide libraries, while the other four approaches are applicable to peptide, non-peptide oligomer, or small molecule libraries of compounds (Lam, Anticancer Drug Des. 12:145, 1997). Examples of methods for the synthesis of molecular libraries can be found in the art, for example, in: DeWitt et al. (Proc. Natl. Acad. Sci. USA 90:6909, 1993); Erb et al. (Proc. Natl. Acad. Sci. USA 91:11422, 1994); Zuckermann et al. (J. Med. Chem. 37:2678, 1994); Cho et al. (Science 261:1303, 1993); Carell et al. (Angew. Chem, Int. Ed. Engl. 33:2059, 1994 and ibid 2061); and in Gallop et al. (Med. Chem. 37:1233, 1994). Libraries of compounds may be presented in solution (e.g., Houghten, Biotechniques 13:412-421, 1992) or on beads (Lam, Nature 354:82-84, 1991), chips (Fodor, Nature 364:555-556, 1993), bacteria or spores (U.S. Pat. No. 5,223,409), plasmids (Cull et al., Proc. Natl. Acad. Sci. USA 89:1865-1869, 1992) or on phage (Scott and Smith, Science 249:386-390, 1990), or luciferase, and the enzymatic label detected by determination of conversion of an appropriate substrate to product.

Once a polypeptide as described herein is identified, it can be isolated and purified by any number of standard methods including, but not limited to, differential solubility (e.g., precipitation), centrifugation, chromatography (e.g., affinity, ion exchange, and size exclusion), or by any other standard techniques used for the purification of peptides, peptidomimetics, or proteins. The functional properties of an identified polypeptide of interest may be evaluated using any functional assay known in the art. Desirably, assays for evaluating downstream receptor function in intracellular signaling are used (e.g., cell proliferation).

For example, the peptidomimetics compounds of the present invention may be obtained using the following three-phase process: (1) scanning the polypeptides described herein to identify regions of secondary structure necessary for targeting the particular cell types described herein; (2) using conformationally constrained dipeptide surrogates to refine the backbone geometry and provide organic platforms corresponding to these surrogates; and (3) using the best organic platforms to display organic pharmocophores in libraries of candidates designed to mimic the desired activity of the native polypeptide. In more detail the three phases are as follows. In phase 1, the lead candidate polypeptides are scanned and their structure abridged to identify the requirements for their activity. A series of polypeptide analogs of the original are synthesized. In phase 2, the best polypeptide analogs are investigated using the conformationally constrained dipeptide surrogates. Indolizidin-2-one, indolizidin-9-one and quinolizidinone amino acids ($I^2aa$, $I^9aa$ and Qaa respectively) are used as platforms for studying backbone geometry of the best peptide candidates. These and related platforms (reviewed in Halab et al., Biopolymers 55:101-122, 2000 and Hanessian et al., Tetrahedron 53:12789-12854, 1997) may be introduced at specific regions of the polypeptide to orient the pharmacophores in different directions. Biological evaluation of these analogs identifies improved lead polypeptides that mimic the geometric requirements for activity. In phase 3, the platforms from the most active lead polypeptides are used to display organic surrogates of the pharmacophores responsible for activity of the native peptide. The pharmacophores and scaffolds are combined in a parallel synthesis format. Derivation of polypeptides and the above phases can be accomplished by other means using methods known in the art.

Structure function relationships determined from the polypeptides, polypeptide derivatives, peptidomimetics or other small molecules described herein may be used to refine and prepare analogous molecular structures having similar or better properties. Accordingly, the compounds of the present invention also include molecules that share the structure, polarity, charge characteristics and side chain properties of the polypeptides described herein.

In summary, based on the disclosure herein, those skilled in the art can develop peptides and peptidomimetics screening assays which are useful for identifying compounds for targeting an agent to particular cell types (e.g., those described herein). The assays of this invention may be developed for low-throughput, high-throughput, or ultra-high throughput screening formats. Assays of the present invention include assays amenable to automation.

Linkers

In embodiments where the MT1-MMP is covalently bound to a delivery vector, the MT1-MMP inhibitor can be bound to a delivery vector either directly (e.g., through a covalent bond such as a peptide bond) or can be bound through a linker. Linkers include chemical linking agents (e.g., cleavable linkers) and peptides.

In some embodiments, the linker is a chemical linking agent. The MT1-MMP inhibitor (e.g. a polypeptide or peptidomimetic) and vector peptide may be conjugated through sulfhydryl groups, amino groups (amines), and/or carbohydrates or any appropriate reactive group. Homobifunctional and heterobifunctional cross-linkers (conjugation agents) are available from many commercial sources. Regions available for cross-linking may be found on the polypeptides of the present invention. The cross-linker may comprise a flexible arm, e.g., 2, 3, 4, 5, 6, 7, 8, 9, 10, 11, 12, 13, 14, or 15 carbon atoms. Exemplary cross-linkers include BS3 ([Bis(sulfosuccinimidyl)suberate]; BS3 is a homobifunctional N-hydroxysuccinimide ester that targets accessible primary amines), NHS/EDC (N-hydroxysuccinimide and 1-ethyl-3-[3-dimethylaminopropyl]carbodiimide; NHS/EDC allows for the conjugation of primary amine groups with carboxyl groups), sulfo-EMCS ([N-e-maleimidocaproic acid]hydrazide; sulfo-EMCS are heterobifunctional reactive groups (maleimide and NHS-ester) that are reactive toward sulfhydryl and amino groups), hydrazide (most proteins contain exposed carbohydrates and hydrazide is a useful reagent for linking carboxyl groups to primary amines), and SATA (N-succinimidyl-S-acetylthioacetate; SATA is reactive towards amines and adds protected sulfhydryls groups).

To form covalent bonds, one can use as a chemically reactive group a wide variety of active carboxyl groups (e.g., esters) where the hydroxyl moiety is physiologically acceptable at the levels required to modify the peptide. Particular agents include N-hydroxysuccinimide (NHS), N-hydroxy-sulfosuccinimide (sulfo-NHS), maleimide-benzoyl-succinimide (MBS), gamma-maleimido-butyryloxy succinimide ester (GMBS), maleimido propionic acid (MPA) maleimido hexanoic acid (MHA), and maleimido undecanoic acid (MUA).

Primary amines are the principal targets for NHS esters. Accessible α-amine groups present on the N-termini of proteins and the ε-amine of lysine react with NHS esters. An amide bond is formed when the NHS ester conjugation reaction reacts with primary amines releasing N-hydroxysuccinimide. These succinimide containing reactive groups are herein referred to as succinimidyl groups. In certain embodiments of the invention, the functional group on the protein will be a thiol group and the chemically reactive group will be a maleimido-containing group such as gamma-maleimide-butrylamide (GMBA or MPA). Such maleimide containing groups are referred to herein as maleido groups.

The maleimido group is most selective for sulfhydryl groups on peptides when the pH of the reaction mixture is 6.5-7.4. At pH 7.0, the rate of reaction of maleimido groups with sulfhydryls (e.g., thiol groups on proteins such as serum albumin or IgG) is 1000-fold faster than with amines. Thus, a stable thioether linkage between the maleimido group and the sulfhydryl can be formed.

In other embodiments, the linker includes at least one amino acid (e.g., a peptide of at least 2, 3, 4, 5, 6, 7, 10, 15, 20, 25, 40, or 50 amino acids). In certain embodiments, the linker is a single amino acid (e.g., any naturally occurring amino acid such as Cys). In other embodiments, a glycine-rich peptide such as a peptide having the sequence [Gly-Gly-Gly-Gly-Ser]$_n$ where n is 1, 2, 3, 4, 5 or 6 is used (SEQ ID NOS:169-174), as described in U.S. Pat. No. 7,271,149. In other embodiments, a serine-rich peptide linker is used, as described in U.S. Pat. No. 5,525,491. Serine rich peptide linkers include those of the formula [X-X-X-X-Gly]$_y$, where up to two of the X are Thr, and the remaining X are Ser, and y is 1 to 5 (e.g., Ser-Ser-Ser-Ser-Gly (SEQ ID NO:175), where y is greater than 1). In some cases, the linker is a single amino acid (e.g., any amino acid, such as Gly or Cys).

Examples of suitable linkers are succinic acid, Lys, Glu, and Asp, or a dipeptide such as Gly-Lys. When the linker is succinic acid, one carboxyl group thereof may form an amide bond with an amino group of the amino acid residue, and the other carboxyl group thereof may, for example, form an amide bond with an amino group of the peptide or substituent. When the linker is Lys, Glu, or Asp, the carboxyl group thereof may form an amide bond with an amino group of the amino acid residue, and the amino group thereof may, for example, form an amide bond with a carboxyl group of the substituent. When Lys is used as the linker, a further linker may be inserted between the ε-amino group of Lys and the substituent. In one particular embodiment, the further linker is succinic acid, which, e.g., forms an amide bond with the ε-amino group of Lys and with an amino group present in the substituent. In one embodiment, the further linker is Glu or Asp (e.g., which forms an amide bond with the ε-amino group of Lys and another amide bond with a carboxyl group present in the substituent), that is, the substituent is an N$^ε$-acylated lysine residue.

Treatment of Disease

As MT1-MMP has been linked to diseases including cancer, heart or vascular disease, and arthritis, the MT1-MMP inhibitors described herein and compositions including the inhibitors (e.g., pharmaceutical compositions) may be used to treat (e.g., prophylactically) any disease where MT1-MMP inhibition is desirable.

Exemplary cancers that can be treated according to the invention include cancers such as glioblastoma, glioma, astrocytoma, medulloblastoma, craniopharyngioma, ependymoma, pinealoma, hemangioblastoma, acoustic neuroma, oligodendroglioma, schwannoma, meningioma, melanoma, neuroblastoma, retinoblastoma, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), lung cancer (e.g., squamous cell carcinoma, adenocarinoma, or large cell carcinoma), colorectal cancer, ovarian cancer (e.g., ovarian adenocarcinoma), prostate cancer, polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, and epithelial carcinoma. In some cases, the cancer is a brain cancer (e.g., glioblastoma, astrocytoma, glioma, meduloblastoma, and oligodendroma, neuroglioma, ependymoma, and meningioma).

Types of arthritis that may be treated using the compositions of the invention include osteoarthritis, rheumatoid arthritis, juvenile rheumatoid arthritis, psoriatic arthritis, polymyalgia rheumatica, and ankylosing spondylitis.

Heart and vascular diseases that may be treated using the compositions of the invention include hypertensive heart disease, atherosclerosis, restinosis, abdominal aortic aneurysm (AAA), thoracic aortic aneurysm, carotid artery disease, peripheral arterial disease (PAD), and renal artery disease.

Formulation, Administration, and Dosage

The present invention also features pharmaceutical compositions that contain a therapeutically effective amount of an MT1-MMP inhibitory compound of the invention. The composition can be formulated for use in a variety of drug delivery systems. One or more physiologically acceptable excipients or carriers can also be included in the composition for proper formulation. Suitable formulations for use in the present invention are found in *Remington's Pharmaceutical Sciences*, Mack Publishing Company, Philadelphia, Pa., 17th ed., 1985. For a brief review of methods for drug delivery, see, e.g., Langer (Science 249:1527-1533, 1990).

The pharmaceutical compositions are intended for parenteral, intranasal, topical, oral, or local administration, such as by a transdermal means, for prophylactic and/or therapeutic treatment. The pharmaceutical compositions can be administered parenterally (e.g., by intravenous, intramuscular, or subcutaneous injection), or by oral ingestion, or by topical application or intraarticular injection at areas affected by the vascular or cancer condition. Additional routes of administration include intravascular, intra-arterial, intratumor, intraperitoneal, intraventricular, intraepidural, as well as nasal, ophthalmic, intrascleral, intraorbital, rectal, topical, or aerosol inhalation administration. Sustained release administration is also specifically included in the invention, by such means as depot injections or erodible implants or components. Thus, the invention provides compositions for parenteral administration that comprise the above mention agents dissolved or suspended in an acceptable carrier, preferably an aqueous carrier, e.g., water, buffered water, saline, PBS, and the like. The compositions may contain pharmaceutically acceptable auxiliary substances as required to approximate physiological conditions, such as pH adjusting and buffering agents, tonicity adjusting agents, wetting agents, detergents and the like. The invention also provides compositions for oral delivery, which may contain inert ingredients such as binders or fillers for the formulation of a tablet, a capsule, and the like. Furthermore, this invention provides compositions for local administration, which may contain inert ingredients such as solvents or emulsifiers for the formulation of a cream, an ointment, and the like.

These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the preparations typically will be between 3 and 11, between 5 and 9 or between 6 and 8 (e.g., between 7 and 8 or 7 to 7.5). The resulting compositions in solid form may be packaged in multiple single dose units, each containing a fixed amount of the above-mentioned agent or agents, such as in a sealed package of tablets or capsules. The composition in solid form can also be packaged in a container for a flexible quantity, such as in a squeezable tube designed for a topically applicable cream or ointment.

The compositions containing an effective amount can be administered for prophylactic or therapeutic treatments. In prophylactic applications, compositions can be administered to a subject with a clinically determined predisposition or increased susceptibility to a disease associated with MT1-MMP activity. Compositions of the invention can be administered to the subject (e.g., a human) in an amount sufficient to delay, reduce, or preferably prevent the onset of clinical disease. In therapeutic applications, compositions are administered to a subject (e.g., a human) already suffering from disease in an amount sufficient to cure or at least partially arrest the symptoms of the condition and its complications. An amount adequate to accomplish this purpose is defined as a "therapeutically effective amount," an amount of a compound sufficient to substantially improve some symptom associated with a disease or a medical condition. For example, in prophylactic treatment of a disease associated with MT1-MMP activity (e.g., those described herein), an agent or compound that decreases, prevents, delays, suppresses, or arrests any symptom of the disease or condition would be therapeutically effective. A therapeutically effective amount of an agent or compound is not required to cure a disease or condition but will provide a treatment for a disease or condition such that the onset of the disease or condition is delayed, hindered, or prevented, or the disease or condition symptoms are ameliorated, or the term of the disease or condition is changed or, for example, is less severe or recovery is accelerated in an individual.

Effective amounts of the compositions described herein can depend on the severity of the disease or condition and the weight and general state of the patient, but generally range from about 0.05 µg to about 1 g (e.g., 0.5-100 mg) of an equivalent amount of the agent or agents per dose per patient. Suitable regimes for initial administration and booster administrations are typified by an initial administration followed by repeated doses at one or more hourly, daily, weekly, or monthly intervals by a subsequent administration. The total effective amount of an agent present in the compositions of the invention can be administered to a mammal as a single dose, either as a bolus or by infusion over a relatively short period of time, or can be administered using a fractionated treatment protocol, in which multiple doses are administered over a more prolonged period of time (e.g., a dose every 4-6, 8-12, 14-16, or 18-24 hours, or every 2-4 days, 1-2 weeks, once a month). Alternatively, continuous intravenous infusion sufficient to maintain therapeutically effective concentrations in the blood are contemplated.

The therapeutically effective amount of one or more agents present within the compositions of the invention and used in the methods of this invention applied to mammals (e.g., humans) can be determined by the ordinarily-skilled artisan with consideration of individual differences in age, weight, and the condition of the mammal. The agents of the invention are administered to a subject (e.g. a mammal, such as a human) in an effective amount, which is an amount that produces a desirable result in a treated subject (e.g. reduction in MT1-MMP activity). Therapeutically effective amounts can also be determined empirically by those of skill in the art.

The patient may also receive an agent in the range of about 0.05 to 1 g dose one or more times per week (e.g., 2, 3, 4, 5, 6, or 7 or more times per week), 0.1 to 2,500 (e.g., 2,000, 1,500, 1,000, 500, 100, 10, 1, 0.5, or 0.1) µg dose per week. A patient may also receive an agent of the composition in the range of 0.1 to 3,000 µg per dose once every two or three weeks.

Single or multiple administrations of the compositions of the invention comprising an effective amount can be carried out with dose levels and pattern being selected by the treating physician. The dose and administration schedule can be determined and adjusted based on the severity of the disease or condition in the patient, which may be monitored throughout the course of treatment according to the methods commonly practiced by clinicians or those described herein.

The compounds of the present invention may be used in combination with either conventional methods of treatment or therapy or may be used separately from conventional methods of treatment or therapy.

When the compounds of this invention are administered in combination therapies with other agents, they may be administered sequentially or concurrently to an individual. Alternatively, pharmaceutical compositions according to the present invention may be comprised of a combination of a compound of the present invention in association with a pharmaceutically acceptable excipient, as described herein, and another therapeutic or prophylactic agent known in the art.

Combination Therapy

The compositions of the invention may be formulated or administered with any other therapy regimen known in the art. For example, when a composition of the invention is used to treat cancer, the composition may be administered in conjunction with any antiproliferative agent known in the art (e.g., those described herein).

Additional therapeutics for treating cancer include those shown in Table 2 below.

TABLE 2

| | | |
|---|---|---|
| Alkylating agents | cyclophosphamide | lomustine |
| | busulfan | procarbazine |
| | ifosfamide | altretamine |
| | melphalan | estramustine phosphate |
| | hexamethylmelamine | mechlorethamine |
| | thiotepa | streptozocin |
| | chlorambucil | temozolomide |
| | dacarbazine | semustine |
| | carmustine | |
| Platinum agents | cisplatin | carboplatinum |
| | oxaliplatin | ZD-0473 (AnorMED) |
| | spiroplatinum | lobaplatin (Aeterna) |
| | carboxyphthalatoplatinum | satraplatin (Johnson Matthey) |
| | tetraplatin | BBR-3464 (Hoffmann-La Roche) |
| | ormiplatin | |
| | iproplatin | SM-11355 (Sumitomo) |
| | | AP-5280 (Access) |
| Antimetabolites | azacytidine | trimetrexate |
| | gemcitabine | deoxycoformycin |
| | capecitabine | fludarabine |
| | 5-fluorouracil | pentostatin |
| | floxuridine | raltitrexed |
| | 2-chlorodeoxyadenosine | hydroxyurea |
| | 6-mercaptopurine | decitabine (SuperGen) |
| | 6-thioguanine | clofarabine (Bioenvision) |
| | cytarabin | irofulven (MGI Pharma) |
| | 2-fluorodeoxy cytidine | DMDC (Hoffmann-La Roche) |
| | methotrexate | |
| | idatrexate | ethynylcytidine (Taiho) |
| | tomudex | |
| Topoisomerase inhibitors | amsacrine | exatecan mesylate (Daiichi) |
| | epirubicin | quinamed (ChemGenex) |
| | etoposide | gimatecan (Sigma-Tau) |
| | epirubicin | diflomotecan (Beaufour-Ipsen) |
| | teniposide or mitoxantrone | |
| | irinotecan | TAS-103 (Taiho) |
| | 7-ethyl-10-hydroxy-camptothecin | elsamitrucin (Spectrum) |
| | topotecan | J-107088 (Merck & Co) |
| | dexrazoxanet (TopoTarget) | BNP-1350 (BioNumerik) |
| | pixantrone (Novuspharma) | CKD-602 (Chong Kun Dang) |
| | rebeccamycin analogue (Exelixis) | |
| | BBR-3576 (Novuspharma) | KW-2170 (Kyowa Hakko) |
| | rubitecan (SuperGen) | |
| Antitumor antibiotics | dactinomycin (actinomycin D) | amonafide |
| | doxorubicin (adriamycin) | azonafide |
| | deoxyrubicin | anthrapyrazole |
| | valrubicin | oxantrazole |
| | daunorubicin (daunomycin) | losoxantrone |
| | therarubicin | bleomycin sulfate (blenoxane) |
| | idarubicin | |
| | rubidazone | bleomycinic acid |
| | plicamycinp | bleomycin A |
| | porfiromycin | bleomycin B |
| | cyanomorpholinodoxorubicin | mitomycin C |
| | mitoxantrone (novantrone) | MEN-10755 (Menarini) |

TABLE 2-continued

| | | |
|---|---|---|
| Antimitotic agents | paclitaxel<br>docetaxel<br>colchicine<br>vinblastine<br>vincristine<br>vinorelbine<br>vindesine<br>dolastatin 10 (NCI)<br>rhizoxin (Fujisawa)<br>mivobulin (Warner-Lambert)<br>cemadotin (BASF)<br>RPR 109881A (Aventis)<br>TXD 258 (Aventis)<br>epothilone B (Novartis)<br>T 900607 (Tularik)<br>T 138067 (Tularik)<br>cryptophycin 52 (Eli Lilly)<br>vinflunine (Fabre)<br>auristatin PE (Teikoku Hormone)<br>BMS 247550 (BMS)<br>BMS 184476 (BMS)<br>BMS 188797 (BMS)<br>taxoprexin (Protarga) | GPX-100 (Gem Pharmaceuticals)<br>SB 408075 (GlaxoSmithKline)<br>E7010 (Abbott)<br>PG-TXL (Cell Therapeutics)<br>IDN 5109 (Bayer)<br>A 105972 (Abbott)<br>A 204197 (Abbott)<br>LU 223651 (BASF)<br>D 24851 (ASTAMedica)<br>ER-86526 (Eisai)<br>combretastatin A4 (BMS)<br>isohomohalichondrin-B (PharmaMar)<br>ZD 6126 (AstraZeneca)<br>PEG-paclitaxel (Enzon)<br>AZ10992 (Asahi)<br>IDN-5109 (Indena)<br>AVLB (Prescient NeuroPharma)<br>azaepothilone B (BMS)<br>BNP-7787 (BioNumerik)<br>CA-4 prodrug (OXiGENE)<br>dolastatin-10 (NIH)<br>CA-4 (OXiGENE) |
| Aromatase inhibitors | aminoglutethimide<br>letrozole<br>anastrazole<br>formestane | exemestane<br>atamestane (BioMedicines)<br>YM-511 (Yamanouchi) |
| Thymidylate synthase inhibitors | pemetrexed (Eli Lilly)<br>ZD-9331 (BTG) | nolatrexed (Eximias)<br>CoFactor ™ (BioKeys) |
| DNA antagonists | trabectedin (PharmaMar)<br>glufosfamide (Baxter International)<br>albumin + 32P (Isotope Solutions)<br>thymectacin (NewBiotics)<br>edotreotide (Novartis) | mafosfamide (Baxter International)<br>apaziquone (Spectrum Pharmaceuticals)<br>O6 benzyl guanine (Paligent) |
| Farnesyltransferase inhibitors | arglabin (NuOncology Labs)<br>lonafarnib (Schering-Plough)<br>BAY-43-9006 (Bayer) | tipifarnib (Johnson & Johnson)<br>perillyl alcohol (DOR BioPharma) |
| Pump inhibitors | CBT-1 (CBA Pharma)<br>tariquidar (Xenova)<br>MS-209 (Schering AG) | zosuquidar trihydrochloride (Eli Lilly)<br>biricodar dicitrate (Vertex) |
| Histone acetyltransferase inhibitors | tacedinaline (Pfizer)<br>SAHA (Aton Pharma)<br>MS-275 (Schering AG) | pivaloyloxymethyl butyrate (Titan)<br>depsipeptide (Fujisawa) |
| Metalloproteinase inhibitors | Neovastat (Aeterna Laboratories)<br>marimastat (British Biotech) | CMT-3 (CollaGenex)<br>BMS-275291 (Celltech) |
| Ribonucleoside reductase inhibitors | gallium maltolate (Titan)<br>triapine (Vion) | tezacitabine (Aventis)<br>didox (Molecules for Health) |
| TNF alpha agonists/antagonists | virulizin (Lorus Therapeutics)<br>CDC-394 (Celgene) | revimid (Celgene) |
| Endothelin A receptor antagonist | atrasentan (Abbott)<br>ZD-4054 (AstraZeneca) | YM-598 (Yamanouchi) |
| Retinoic acid receptor agonists | fenretinide (Johnson & Johnson)<br>LGD-1550 (Ligand) | alitretinoin (Ligand) |
| Immuno-modulators | interferon<br>oncophage (Antigenics)<br>GMK (Progenics)<br>adenocarcinoma vaccine (Biomira)<br>CTP-37 (AVI BioPharma)<br>IRX-2 (Immuno-Rx)<br>PEP-005 (Peplin Biotech)<br>synchrovax vaccines (CTL Immuno)<br>melanoma vaccine (CTL Immuno)<br>p21 RAS vaccine (GemVax)<br>cepharanthine | dexosome therapy (Anosys)<br>pentrix (Australian Cancer Technology)<br>ISF-154 (Tragen)<br>cancer vaccine (Intercell)<br>norelin (Biostar)<br>BLP-25 (Biomira)<br>MGV (Progenics)<br>β-alethine (Dovetail)<br>CLL therapy (Vasogen) |
| Hormonal and antihormonal agents | estrogens<br>conjugated estrogens<br>ethinyl estradiol<br>chlortrianisen<br>idenestrol<br>hydroxyprogesterone caproate<br>medroxyprogesterone<br>testosterone | methylprednisolone<br>prednisolone<br>aminoglutethimide<br>leuprolide<br>goserelin<br>leuporelin<br>bicalutamide<br>flutamide |

TABLE 2-continued

| | | |
|---|---|---|
| | testosterone propionate; fluoxymesterone<br>methyltestosterone<br>diethylstilbestrol<br>megestrol<br>Tamoxifen<br>toremofine<br>dexamethasone<br>prednisone | octreotide<br>nilutamide<br>mitotane<br>P-04 (Novogen)<br>2-methoxyestradiol<br>(EntreMed)<br>arzoxifene (Eli Lilly)<br>raloxifene |
| Photodynamic agents | talaporfin (Light Sciences)<br>Theralux (Theratechnologies)<br>motexafin gadolinium (Pharmacyclics) | Pd-bacteriopheophorbide<br>(Yeda)<br>lutetium texaphyrin<br>(Pharmacyclics)<br>hypericin |
| Tyrosine Kinase Inhibitors | imatinib<br>leflunomide (Sugen/Pharmacia)<br>ZD1839 (AstraZeneca)<br>erlotinib (Oncogene Science)<br>gefitinib<br>canertinib (Pfizer)<br>squalamine (Genaera)<br>SU5416 (Pharmacia)<br>SU6668 (Pharmacia)<br>ZD4190 (AstraZeneca)<br>ZD6474 (AstraZeneca)<br>vatalanib (Novartis)<br>PKI166 (Novartis)<br>GW2016 (GlaxoSmithKline)<br>EKB-509 (Wyeth)<br>EKB-569 (Wyeth) | kahalide F (PharmaMar)<br>CEP-701 (Cephalon)<br>CEP-751 (Cephalon)<br>MLN518 (Millenium)<br>PKC412 (Novartis)<br>phenoxodiol ( )<br>trastuzumab (Genentech)<br>C225 (ImClone)<br>rhu-Mab (Genentech)<br>MDX-H210 (Medarex)<br>2C4 (Genentech)<br>MDX-447 (Medarex)<br>ABX-EGF (Abgenix)<br>IMC-1C11 (ImClone) |

| Miscellaneous agents | |
|---|---|
| SR-27897 (CCK A inhibitor, Sanofi-Synthelabo)<br>tocladesine (cyclic AMP agonist, Ribapharm)<br>alvocidib (CDK inhibitor, Aventis)<br>CV-247 (COX-2 inhibitor, Ivy Medical)<br>P54 (COX-2 inhibitor, Phytopharm)<br>CapCell ™ (CYP450 stimulant, Bavarian Nordic)<br>GCS-100 (gal3 antagonist, GlycoGenesys)<br>G17DT immunogen (gastrin inhibitor, Aphton)<br>efaproxiral (oxygenator, Allos Therapeutics)<br>PI-88 (heparanase inhibitor, Progen)<br>tesmilifene (histamine antagonist, YM BioSciences)<br>histamine (histamine H2 receptor agonist, Maxim)<br>tiazofurin (IMPDH inhibitor, Ribapharm)<br>cilengitide (integrin antagonist, Merck KGaA)<br>SR-31747 (IL-1 antagonist, Sanofi-Synthelabo)<br>CCI-779 (mTOR kinase inhibitor, Wyeth)<br>exisulind (PDE V inhibitor, Cell Pathways)<br>CP-461 (PDE V inhibitor, Cell Pathways)<br>AG-2037 (GART inhibitor, Pfizer)<br>WX-UK1 (plasminogen activator inhibitor, Wilex)<br>PBI-1402 (PMN stimulant, ProMetic LifeSciences)<br>bortezomib (proteasome inhibitor, Millennium)<br>SRL-172 (T cell stimulant, SR Pharma)<br>TLK-286 (glutathione S transferase inhibitor, Telik)<br>PT-100 (growth factor agonist, Point Therapeutics)<br>midostaurin (PKC inhibitor, Novartis)<br>bryostatin-1 (PKC stimulant, GPC Biotech)<br>CDA-II (apoptosis promoter, Everlife)<br>SDX-101 (apoptosis promoter, Salmedix)<br>ceflatonin (apoptosis promoter, ChemGenex) | BCX-1777 (PNP inhibitor, BioCryst)<br>ranpirnase (ribonuclease stimulant,<br>Alfacell)<br>galarubicin (RNA synthesis inhibitor,<br>Dong-A)<br>tirapazamine (reducing agent, SRI<br>International)<br>N-acetylcysteine (reducing agent,<br>Zambon)<br>R-flurbiprofen (NF-kappaB inhibitor,<br>Encore)<br>3CPA (NF-kappaB inhibitor, Active<br>Biotech)<br>seocalcitol (vitamin D receptor agonist,<br>Leo)<br>131-I-TM-601 (DNA antagonist,<br>TransMolecular)<br>eflornithine (ODC inhibitor, ILEX<br>Oncology)<br>minodronic acid (osteoclast inhibitor,<br>Yamanouchi)<br>indisulam (p53 stimulant, Eisai)<br>aplidine (PPT inhibitor, PharmaMar)<br>rituximab (CD20 antibody, Genentech)<br>gemtuzumab (CD33 antibody, Wyeth<br>Ayerst)<br>PG2 (hematopoiesis enhancer,<br>Pharmagenesis)<br>Immunol ™ (triclosan oral rinse, Endo)<br>triacetyluridine (uridine prodrug,<br>Wellstat)<br>SN-4071 (sarcoma agent, Signature<br>BioScience)<br>TransMID-107 ™ (immunotoxin, KS<br>Biomedix)<br>PCK-3145 (apoptosis promoter,<br>Procyon)<br>doranidazole (apoptosis promoter,<br>Pola)<br>CHS-828 (cytotoxic agent, Leo)<br>trans-retinoic acid (differentiator, NIH)<br>MX6 (apoptosis promoter, MAXIA)<br>apomine (apoptosis promoter, ILEX<br>Oncology)<br>urocidin (apoptosis promoter,<br>Bioniche)<br>Ro-31-7453 (apoptosis promoter, La<br>Roche) |

TABLE 2-continued brostallicin (apoptosis promoter, Pharmacia)

Additional therapeutics for treating a vascular or heart disease include agents such as anti-inflammatory agents, e.g., non-steroidal anti-inflammatory drugs (NSAIDs; e.g., detoprofen, diclofenac, diflunisal, etodolac, fenoprofen, flurbiprofen, ibuprofen, indomethacin, ketoprofen, meclofenameate, mefenamic acid, meloxicam, nabumeone, naproxen sodium, oxaprozin, piroxicam, sulindac, tolmetin, celecoxib, rofecoxib, aspirin, choline salicylate, salsalte, and sodium and magnesium salicylate) steroids (e.g., cortisone, dexamethasone, hydrocortisone, methylprednisolone, prednisolone, prednisone, triamcinolone), antibacterial agents (e.g., azithromycin, clarithromycin, erythromycin, roxythromycin, gatifloxacin, levofloxacin, amoxicillin, or metronidazole), platelet aggregation inhibitors (e.g., abciximab, aspirin, cilostazol, clopidogrel, dipyridamole, eptifibatide, ticlopidine, or tirofiban), anticoagulants (e.g., dalteparin, danaparoid, enoxaparin, heparin, tinzaparin, or warfarin), antipyretics (e.g., acetaminophen), ticlopidine, clopidogrel, angiotensin converting enzyme inhibitors, beta blockers, pentoxifylline, cilostazol, estrogen replacement therapy, lipid-lowering agents (e.g., cholestyramine, colestipol, nicotinic acid, gemfibrozil, probucol, ezetimibe, or statins such as atorvastatin, rosuvastatin, lovastatin simvastatin, pravastatin, cerivastatin, and fluvastatin).

Additional therapeutics for treating rheumatoid arthritis include CD20 binding antibodies (e.g., rituximab, ocrelizumab, ofatumumab, HuMax-CD20, and variants thereof), DMARDS (disease-modifying anti-rheumatic drugs), NSAIDs (non-steroidal anti-inflammatory drugs), immunosuppressants (e.g., azathioprine; mycophenolate mofetil (CellCept®; Roche)), analgesics, corticosteroids (e.g., prednisone), glucocorticosteroids, cyclophosphamides, HUMIRA™ (adalimumab; Abbott Laboratories), ARAVA® (leflunomide), REMICADE® (infliximab; Centocor, Inc.), ENBREL (etanercept; Amgen), ACTEMRA (tocilizumab; Roche, Switzerland), and COX-2 inhibitors (e.g., GW406381). DMARDs include methotrexate, hydroxycloroquine, sulfasalazine, leflunomide, etanercept, infliximab, azathioprine, D-penicillamine, gold or gold salts (oral or intramuscular), minocycline, cyclosporine, cyclosporine A, Staphylococcal protein A immunoadsorptionm and interleukin-1 blockers (e.g., anakinra and interleukin-1 receptor antagonist). The DMARD may be a TNFα blocker (e.g., adalimumab (human monoclonal anti-TNFα antibody), CDP870 (UCB), pegsunercept, and atacicept), infliximab (chimeric monoclonal anti-TNFα antibody), and etanercept ("immunoadhesin" fusion protein consisting of the extracellular ligand binding portion of the human 75 kD (p75) tumor necrosis factor receptor (TNFR) and the Fc portion of a human IgG1). ACTEMRA (tocilizumab) is a humanized antihuman interleukin-6 (IL-6) receptor. NSAIDs include acetaminophen, ibuprofen, aspirin, an opiate, or lidocaine (topical). Other agents used to treat rheumatoid arthritis include pioglitazone, canakinumab, p38 kinase inhibitors (e.g., SCIO-469, VX-702, BMS-582949, and PH-797804), MEK inhibitors (e.g., ARRY-438162), rosiglitazone, Tripterygium wilfordi Hook F, SBI-087, Cura-100, AZD5672 (AstraZeneca), paclitaxel, lumiracoxib, golimumab, estrogen receptor-β agonist (e.g., ERB-041), A3 adenosine receptor agonist (e.g., CF101; Can-Fite BioPharma), roxithromycin, ADL5859 (Adolor Corp.), GW856553 (GlaxoSmithKline), ASK8007 (Astellas Pharma, Inc.), HE3286 (Hollis-Eden Pharmaceuticals, San Diego, Calif.), TRU-015 (Wyeth), belimumab, AZD9056 (AstraZeneca), ACZ885 (Novartis), GSK3152314A (GlaxoSmithKline), anti-IL-17 antibodies (e.g., AIN457 (Novartis) and AMG 827 (Amgen)), Fentanyl transdermal patch (Janssen Pharmaceutica N.V., Belgium), valdecoxib, CNTO 136 (Centocor, Inc.), imatinib (Novartis), JAK-3 inhibitors (e.g., CP-690,550 (Pfizer)), cathepsin-S inhibitors (e.g., RWJ-445380 (Johnson & Johnson)), ISIS 104838 (Isis Pharmaceuticals), MM-093 (Merrimack Pharmaceuticals), bovine type II collagen, lovastatin, anti-RANK ligand antibodies (e.g., denosumab (Amgen)), dnaj peptide, Etoricoxib (Merck), SB-681323 (GlaxoSmithKline), Rofecoxib (Merck), omegaven, anti-CD19 antibodies (e.g., MDX-1342 (Medarex)), AMG 108 (Amgen), TMI-005 (Wyeth), Abatacept (Bristol-Myers-Squibb), baminercept (BiogenIdec), fostamatinib disodium (Rigel Pharmaceuticals), temsirolimus (Wyeth), ARRY-371797 (Array BioPharma), Natalizumab (Elan Pharmaceuticals), AMG 719 (Amgen), CE-224,535 (Pfizer), TAK-715 (Takeda), TAK-783 (Takeda), BG9924 (Biogen Idec), GW274150 (GlaxoSmithKline), GSK1827771 (GlaxoSmithKline), CH-1504 (Chelsea Therapeutics), Certolizumab pegol (UCB), tramadol, LY2127399 (Eli Lily), curcumin, MTRX1011A (Tolerex/Genetech), AMG 714 (Amgen), CAM-3001 (MedImmune), BIIB023 (Biogen Idec), SSR150106 (Sanofi-Aventis), STA 5326 (Synta Pharmaceuticals), P38 Inhibitor (4) (Hoffman-La Roche), etoricoxib (Merck), MEDI-522 (MedImmune), γ-linolenic acid, Ramipril (Sanofi-Aventis), CRx-102 (CombinatoRx), efalizumab, LY2189102 (Eli Lily), MK-0873 (Merck), fontolizumab (PDL BioPharma), Maraviroc (Pfizer), HuMax-CD4 (Genmab), CP-195,543 (Pfizer), meloxicam (Boehringer Ingelheim Pharmaceuticals), bucillamine, PD 0360324 (Pfizer), FANG(30), PLA-695 (Wyeth), PG-760564 (Procter and Gamble), MK0812 (Merck), tgAAC94 (Targeted Genetics), SMP-114 (Dainippon Sumitomo Pharma Europe), RhuDex (Medigene), MK0359 (Merck). For conventional treatment of RA, see, e.g., "Guidelines for the management of rheumatoid arthritis" *Arthritis & Rheumatism* 46:328-346 (2002).

These additional therapeutic agents may be administered within 14 days, 7 days, 2 days, 1 day, 12 hours, 6 hours, or 1 hour of administration of a MT1-MMP inhibitory therapeutic, or simultaneously therewith. The additional therapeutic agent may be present in the same or different pharmaceutical compositions as the MT1-MMP inhibitory therapeutic of the invention. When present in different pharmaceutical compositions, different routes of administration may be used. For example, the MT1-MMP inhibitory therapeutic may be administered orally, while a second agent may be administered by intravenous, intramuscular, or subcutaneous injection.

The following examples are intended to illustrate, rather than limit, the invention Example 1

Generation of MT1-MMP Derived Peptides

In performing the experiments described in the examples below, the following peptides were generated. First, a peptide having the sequence of the cytoplasmic domain of MT1-MMP (RRHGTPRRLLYCQRSLLDKV; SEQ ID NO:117), as well as a nonphosphorylatable form of this peptide (RRHGTPRRLLFCQRSLLDKV; SEQ ID NO:118), which has a phenylalanine in place of a tyrosine at the position corresponding to amino acid 573 of the human MT1-MMP sequence were generated. The nonphosphorylatable peptide has been termed "M-14."

In addition, peptides having the M-14 sequence fused to the cell penetrating third helix of the homeodomain of Antennapedia protein (RQIKIWFQNRRMKWKK; SEQ ID NO:119) were generated. This fusion peptide is called ACM-14 and has the sequence Biotin-Ahx-RQIKIWFQNRRMK-WKK-RRHGTPRRLLFCQRSLLDKV (SEQ ID NO:176). For use as a control, a version of the fusion peptide, where the cytoplamsic MT1-MMP domain sequence is scrambled was generated. This peptide has the sequence Biotin-Ahx-RQIKI-WFQNRRMKWKK-TLRQRRCLPHFDSGLRKVRL (SEQ ID NO:177) and is termed scACM-14. These peptides are shown in FIG. 1.

Example 2

Expression of Y573F MT1-MMP Inhibits Tumor Growth

Figure 2:
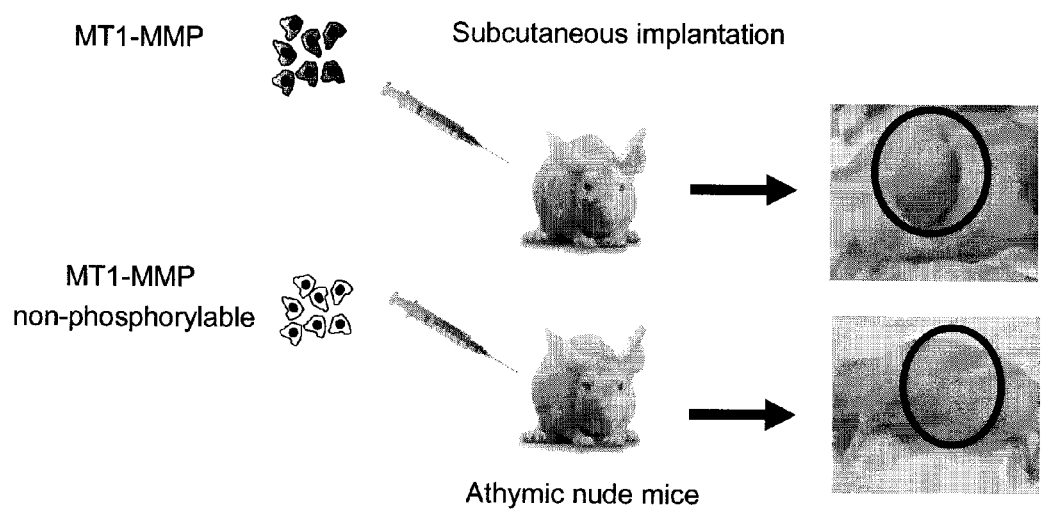
FIG. 2 is a set of images showing that expression of nonphosphorylatable MT1-MMP in HT-1080 fibrosarcoma cells reduces tumor growth of those cells when implanted into athymic nude mice.

HT1080 fibrosarcoma cells were stably transfected with either WT MT1-MMP or Y573F MT1-MMP. HT1080 cells are very aggressive cancer cells that express elevated levels of MT1-MMP. Both groups of cells were transplanted subcutaneously into athymic nude mice, and tumor growth was monitored. As shown in FIG. 2, cells expressing the cytoplasmic domain of MT1-MMP exhibited significant tumor growth, whereas no tumor growth was observed in the mice that received cells expressing Y573F mutant.

Example 3

ACM-14 and scACM-14 are efficiently Taken Up by Fibrosacrcoma Cells

Figure 3:
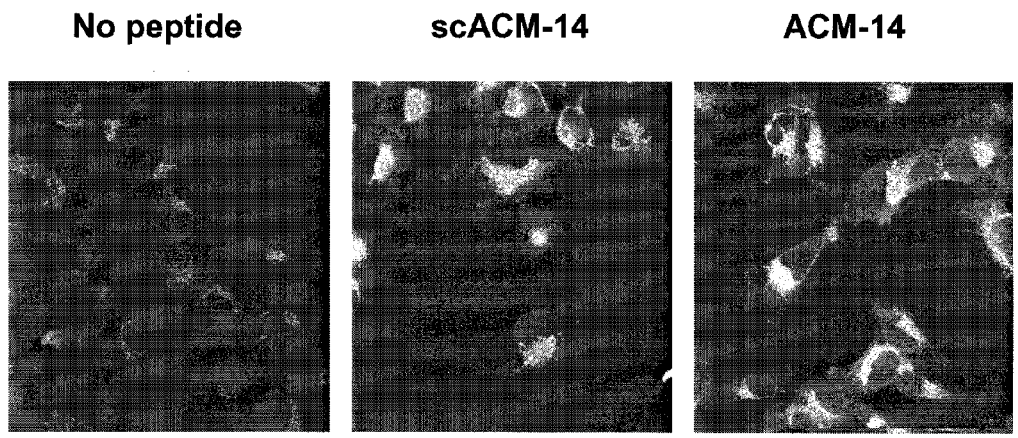
FIG. 3 is a set of photomicrographs showing uptake of scACM-14 and ACM-14 into cells.

To determine whether ACM-14 and scACM-14 were capable of entering tumor cells, HT-1080 fibrosarcoma cells were incubated with each peptide (1 µM) for one hour, and peptide uptake was analyzed by immunofluorescence and confocal microscopy. As shown in FIG. 3, both ACM-14 and its scrambled version (scACM-14) were visualized in the cells, indicated efficient and rapid cellular uptake.

Example 4

Selective Inhibition of MT1-MMP Phosphorylation

Figure 4:
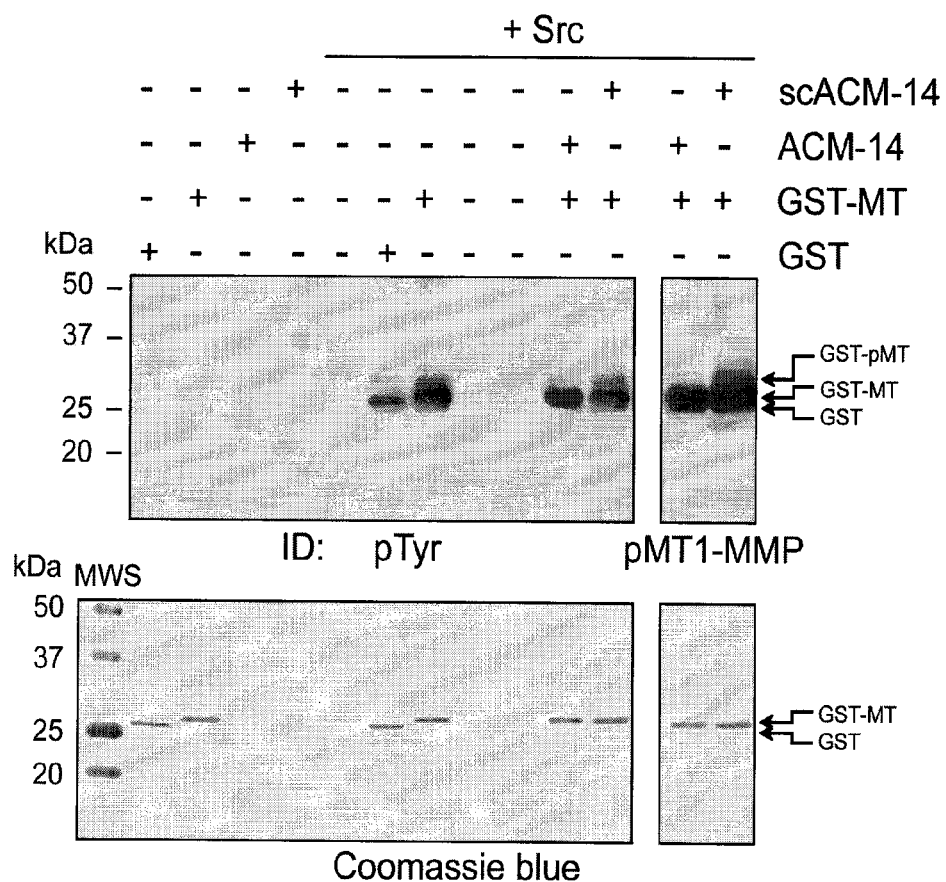
FIG. 4 is a photograph of a western blot showing inhibition of MT1-MMP phosphorylation by ACM-14, but not scACM-14.

We have shown that overexpression of the Y573F mutant of full length MT1-MMP in fibrosarcoma cells reduces the Src-mediated phosphorylation of endogenous MT1-MMP (Nyalendo et al., J Biol Chem 282, 15690-15699, 2007). In order to determine the effect of ACM-14 in this process, we have performed an in vitro phosphorylation assay. The GST-MT1-MMP cytoplasmic tail fusion protein (GST-MT) was incubated with recombinant Src kinase in the presence of ATP and the phosphorylation products were analyzed by western blotting. As shown in FIG. 4, Src-mediated tyrosine phosphorylation of GST-MT was completely inhibited by incubation with ACM-14. The inhibition was not observed with the control peptide scACM-14, indicating that ACM-14 selectively inhibits MT1-MMP phosphorylation in vitro. These surprising results suggest that a nonphosphorylatable form of the cytoplasmic domain of MT1-MMP alone is sufficient to inhibit MT1-MMP phosphorylation in the absence of other portions of the MT1-MMP protein.

Example 5

Inhibition of Tumor Cell Proliferation Within 3D Collagen Matrix

Figure 5:
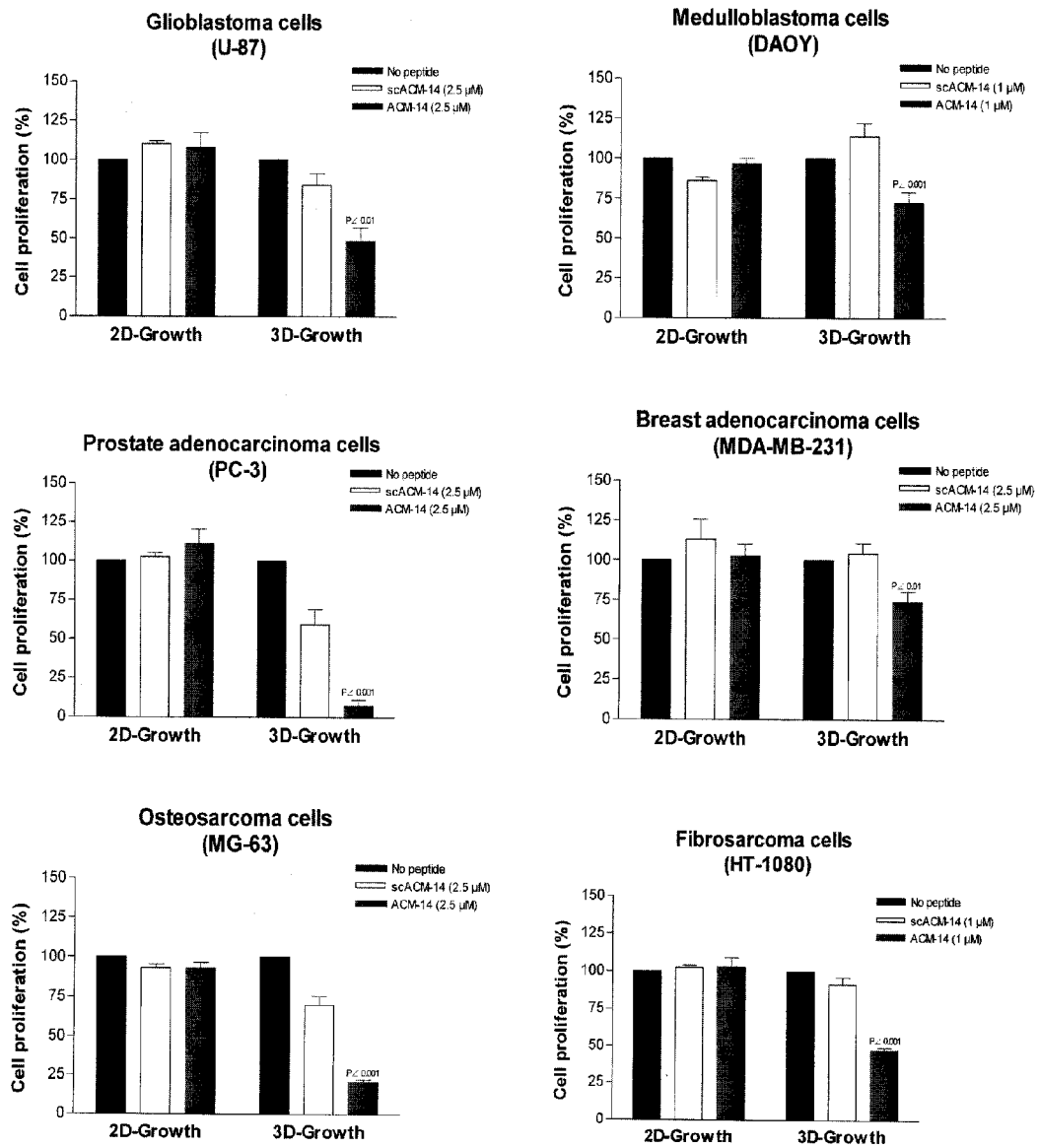
FIG. 5 is a set of graphs showing tumor growth in 2D and 3D culture of glioblastoma cells (U-87), medulloblastoma cells (DAOY), prostate adinocarcinoma cells (PC-3), breast adenocarcinoma cells (MDA-MB-231), osteosarcoma cells (MG-63), and fibrosarcoma cells (HT-1080) in the presence or absence of ACM-14 or scACM-14. Three dimensional tumor growth reduction in the presence of ACM-14 was observed in all cells.

The effect of ACM-14 on tumor cell proliferation under planar conditions (2D) and tumorigenic conditions (3D) was evaluated. Different tumor cell lines were incubated with the peptides and grown atop of a collagen film (2D) or within a collagen gel (3D). As presented in FIG. 5, ACM-14 does not affect tumor cell proliferation in 2D conditions. By contrast, ACM-14 significantly reduces the proliferation of several tumor cells grown in 3D collagen gels. Indeed, treatment of human brain cancer cells with ACM-14 decreases their proliferation in 3D matrix (50% reduction for glioblastoma cells and 35% for medulloblastoma cells), whereas treatment with the scrambled peptide (scACM-14) has no effect on the proliferation of these cells. ACM-14 also inhibits 3D proliferation of prostate cancer, breast cancer, bone cancer, and fibrosarcoma cells.

Example 6

Inhibition of Tumor Growth in vivo

Figure 6:
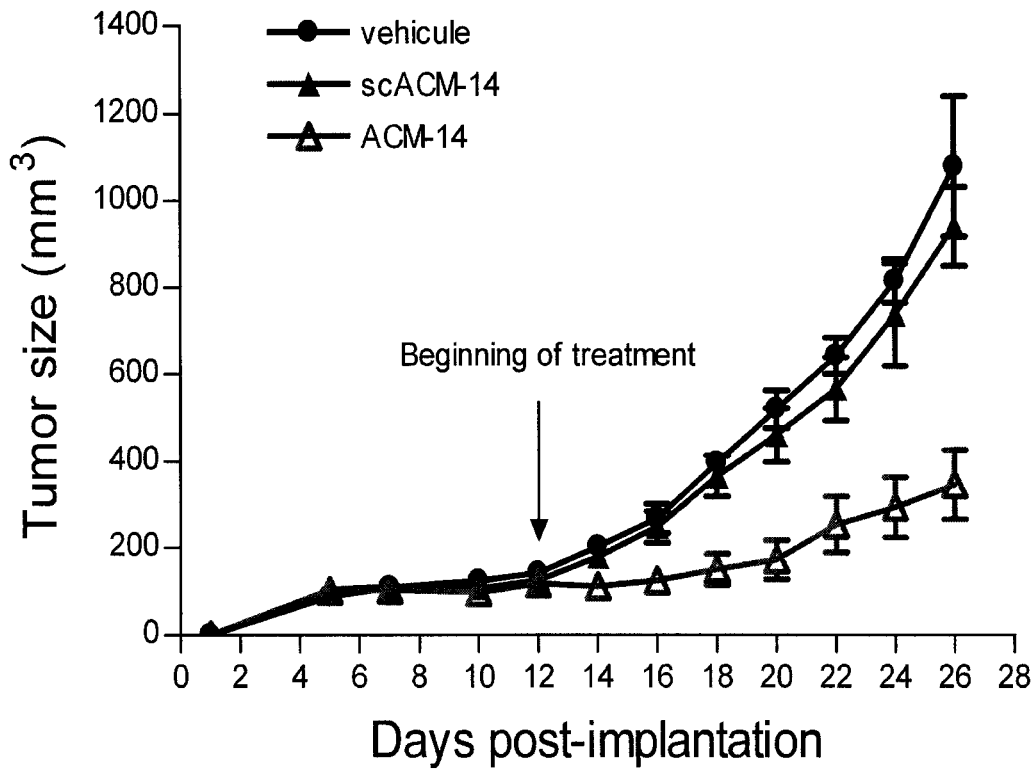
FIG. 6 is a graph showing tumor size of implanted fibrosarcoma cells in nude, athymic mice with treatment of vehicle alone, scACM-14, or ACM-14. ACM-14 treatment is observed to reduce tumor size significantly.
Figure 7:
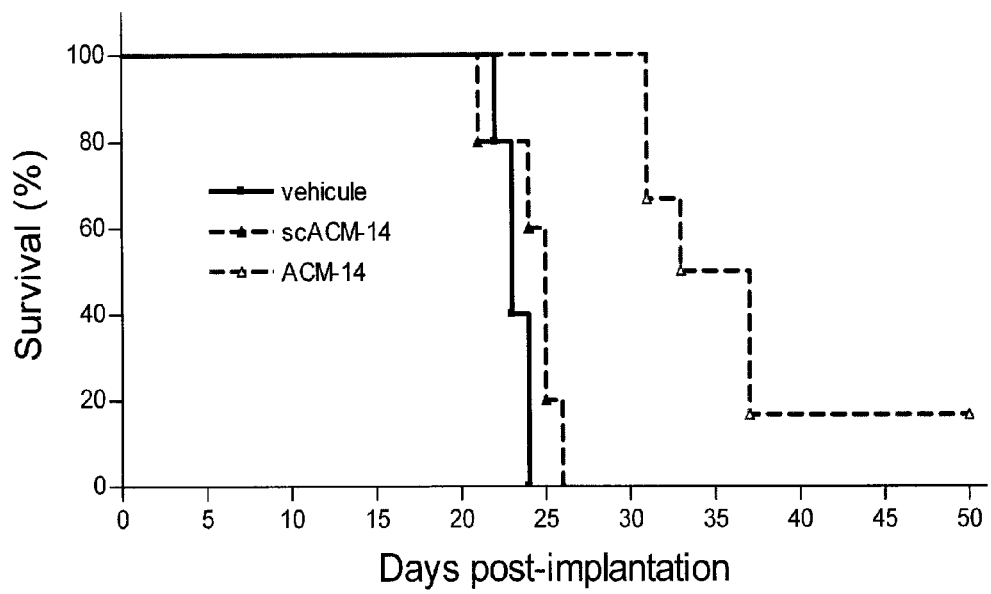
FIG. 7 is a graph showing survival of nude athymic mice with implanted fibrosarcoma cells receiving vehicle alone, scACM-14, or ACM-14. Mice receiving ACM-14 exhibited longer survival times than mice receiving the vehicle or scACM-14.

The effects of ACM-14 on xenograft tumor formation in vivo were also investigated. Fibrosarcoma cells were implanted subcutaneously into the flank of athymic nude mice. Tumors were allowed to grow until approximately 100 mm$^3$ before the mice were randomly separated into three groups for treatment (vehicle, scACM-14, and ACM-14). Mice were given daily subcutaneous administrations of 10 mg/kg of peptides or vehicle. ACM-14 strongly reduces tumor growth by 70% 26 days post-implantation (FIG. 6). The survival of mice that have received ACM-14 was dramatically increased by 10 days (FIG. 7). Furthermore, 17% of tumors completely regressed and totally disappeared following ACM-14 administration.

Example 7

Angiopep-M14 Conjugate

Figure 8:
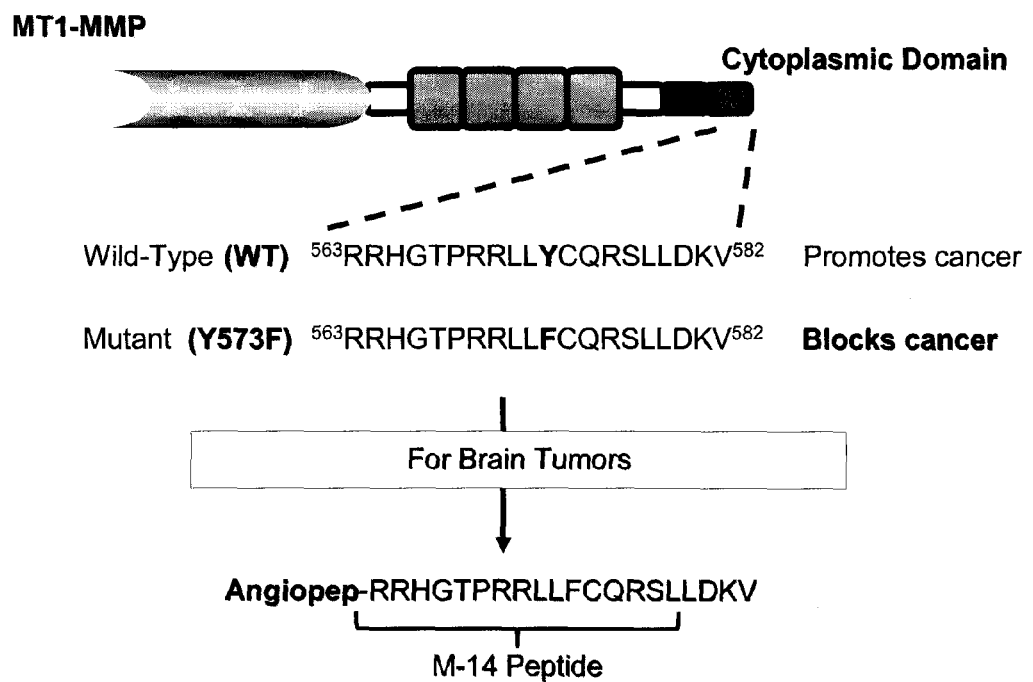
FIG. 8 is a schematic diagram of an Angiopep-ACM-14 conjugate. Wild-Type (WT): SEQ ID NO: 117; Mutant (Y573F)/M14 Peptide: SEQ ID NO: 118.

For delivery of the M14 peptide across the BBB, a fusion peptide containing the M14 sequence and an Angiopep peptide sequence (e.g., SEQ ID NO:178) is produced. In this example, the Angiopep peptide has the sequence of Angiopep-2, which is capable of crossing the BBB of a mammalian subject (FIG. 8).

Other Embodiments

All patents; patent applications, including U.S. Provisional Application No. 61/138,375, filed Dec. 17, 2008; and publications mentioned in this specification are herein incorporated by reference to the same extent as if each independent patent, patent application, or publication was specifically and individually indicated to be incorporated by reference.

What is claimed is:

1. A composition comprising a soluble polypeptide consisting of the amino acid sequence RRHGTPRRLLFCQRSLLDKV (SEQ ID NO:118), wherein said polypeptide is capable of inhibiting membrane type-1 metalloproteinase (MT1-MMP) activity.

2. A composition comprising a conjugate comprising a soluble polypeptide consisting of the amino acid sequence RRHGTPRRLLFCQRSLLDKV (SEQ ID NO:118) and an amino acid sequence capable of penetrating a cellular membrane, capable of entering a particular cell type, or capable of crossing the blood-brain barrier (BBB).

3. The composition of claim 2, wherein said amino acid sequence capable of penetrating a cell membrane is the third helix of the homeodomain of the antennapedia protein (RQIKIWFQNRRMKWKK; SEQ ID NO:119).

4. The composition of claim 3, wherein said polypeptide comprises the sequence RQIKIWFQNRRMKWKKRRHGTPRRLLFCQRSLLDKV (SEQ ID NO:176).

5. The composition of claim 2, wherein said amino acid sequence capable of crossing the BBB is at least 90% identical to Angiopep-2 (SEQ ID NO:97) or Angiopep-1 (SEQ ID NO:67).

6. The composition of claim 5, wherein said amino acid sequence capable of crossing the BBB is Angiopep-1 (SEQ ID NO:67) or Angiopep-2 (SEQ ID NO:97).

7. The composition of claim 6, wherein said polypeptide comprises both Angiopep-2 (SEQ ID NO:97) and the sequence RRHGTPRRLLFCQRSLLDKV (SEQ ID NO:118).

8. The composition of claim 7, wherein said polypeptide comprises the sequence TFFYGGSRGKRNNFKTEEYRRHGTPRRLLFCQRSLLDKV (SEQ ID NO:178).

9. The composition of claim 2, wherein amino acid sequence capable of entering a particular cell type is at least 90% identical to Angiopep-7 (SEQ ID NO:112).

10. The composition of claim 9, wherein said amino acid sequence capable of entering a particular cell type is Angiopep-7 (SEQ ID NO:112).

11. The composition of claim 1, wherein said composition is a liposomal formulation.

12. The composition of claim 11, wherein said liposome comprises a peptide vector, wherein said vector peptide is on the exterior surface of said liposome.

13. The composition of claim 2, wherein said composition is formulated with a pharmaceutically acceptable carrier.

14. A method of reducing MT1-MMP phosphorylation in a cell, said method comprising administering a composition of claim 1 to said cell.

15. The method of claim 14, wherein said cell is in a subject.

16. A method of treating fibrosarcoma, said method comprising administering the composition of claim 1 or 2 to a subject having fibrosarcoma in an amount sufficient to treat said fibrosarcoma.

17. The method of claim 15, wherein said subject is a human.

* * * * *

SEQUENCE LISTING

<160> NUMBER OF SEQ ID NOS: 179

<210> SEQ ID NO 1
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Thr Phe Val Tyr Gly Gly Cys Arg Ala Lys Arg Asn Asn Phe Lys Ser
1               5                   10                  15

Ala Glu Asp

<210> SEQ ID NO 2
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Thr Phe Gln Tyr Gly Gly Cys Met Gly Asn Gly Asn Asn Phe Val Thr
1               5                   10                  15

Glu Lys Glu

<210> SEQ ID NO 3
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Pro Phe Phe Tyr Gly Gly Cys Gly Gly Asn Arg Asn Asn Phe Asp Thr
1               5                   10                  15

Glu Glu Tyr

<210> SEQ ID NO 4
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ser Phe Tyr Tyr Gly Gly Cys Leu Gly Asn Lys Asn Asn Tyr Leu Arg
1               5                   10                  15

Glu Glu Glu

<210> SEQ ID NO 5
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Thr Phe Phe Tyr Gly Gly Cys Arg Ala Lys Arg Asn Asn Phe Lys Arg
1               5                   10                  15

Ala Lys Tyr

```
<210> SEQ ID NO 6
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6
```

Thr Phe Phe Tyr Gly Gly Cys Arg Gly Lys Arg Asn Asn Phe Lys Arg
1               5                   10                  15

Ala Lys Tyr

```
<210> SEQ ID NO 7
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7
```

Thr Phe Phe Tyr Gly Gly Cys Arg Ala Lys Lys Asn Asn Tyr Lys Arg
1               5                   10                  15

Ala Lys Tyr

```
<210> SEQ ID NO 8
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8
```

Thr Phe Phe Tyr Gly Gly Cys Arg Gly Lys Lys Asn Asn Phe Lys Arg
1               5                   10                  15

Ala Lys Tyr

```
<210> SEQ ID NO 9
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9
```

Thr Phe Gln Tyr Gly Gly Cys Arg Ala Lys Arg Asn Asn Phe Lys Arg
1               5                   10                  15

Ala Lys Tyr

```
<210> SEQ ID NO 10
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10
```

Thr Phe Gln Tyr Gly Gly Cys Arg Gly Lys Lys Asn Asn Phe Lys Arg

```
1               5                   10                  15

Ala Lys Tyr

<210> SEQ ID NO 11
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Thr Phe Phe Tyr Gly Gly Cys Leu Gly Lys Arg Asn Asn Phe Lys Arg
1               5                   10                  15

Ala Lys Tyr

<210> SEQ ID NO 12
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Thr Phe Phe Tyr Gly Gly Ser Leu Gly Lys Arg Asn Asn Phe Lys Arg
1               5                   10                  15

Ala Lys Tyr

<210> SEQ ID NO 13
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Pro Phe Phe Tyr Gly Gly Cys Gly Gly Lys Lys Asn Asn Phe Lys Arg
1               5                   10                  15

Ala Lys Tyr

<210> SEQ ID NO 14
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Thr Phe Phe Tyr Gly Gly Cys Arg Gly Lys Gly Asn Asn Tyr Lys Arg
1               5                   10                  15

Ala Lys Tyr

<210> SEQ ID NO 15
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15
```

```
Pro Phe Phe Tyr Gly Gly Cys Arg Gly Lys Arg Asn Asn Phe Leu Arg
1               5                   10                  15

Ala Lys Tyr

<210> SEQ ID NO 16
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Thr Phe Phe Tyr Gly Gly Cys Arg Gly Lys Arg Asn Asn Phe Lys Arg
1               5                   10                  15

Glu Lys Tyr

<210> SEQ ID NO 17
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Pro Phe Phe Tyr Gly Gly Cys Arg Ala Lys Lys Asn Asn Phe Lys Arg
1               5                   10                  15

Ala Lys Glu

<210> SEQ ID NO 18
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Thr Phe Phe Tyr Gly Gly Cys Arg Gly Lys Arg Asn Asn Phe Lys Arg
1               5                   10                  15

Ala Lys Asp

<210> SEQ ID NO 19
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Thr Phe Phe Tyr Gly Gly Cys Arg Ala Lys Arg Asn Asn Phe Asp Arg
1               5                   10                  15

Ala Lys Tyr

<210> SEQ ID NO 20
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20
```

Thr Phe Phe Tyr Gly Gly Cys Arg Gly Lys Lys Asn Asn Phe Lys Arg
1               5                   10                  15

Ala Glu Tyr

<210> SEQ ID NO 21
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Pro Phe Phe Tyr Gly Gly Cys Gly Ala Asn Arg Asn Asn Phe Lys Arg
1               5                   10                  15

Ala Lys Tyr

<210> SEQ ID NO 22
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Thr Phe Phe Tyr Gly Gly Cys Gly Gly Lys Lys Asn Asn Phe Lys Thr
1               5                   10                  15

Ala Lys Tyr

<210> SEQ ID NO 23
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Thr Phe Phe Tyr Gly Gly Cys Arg Gly Asn Arg Asn Asn Phe Leu Arg
1               5                   10                  15

Ala Lys Tyr

<210> SEQ ID NO 24
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Thr Phe Phe Tyr Gly Gly Cys Arg Gly Asn Arg Asn Asn Phe Lys Thr
1               5                   10                  15

Ala Lys Tyr

<210> SEQ ID NO 25
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 25

Thr Phe Phe Tyr Gly Gly Ser Arg Gly Asn Arg Asn Phe Lys Thr
1               5                   10                  15

Ala Lys Tyr

<210> SEQ ID NO 26
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Thr Phe Phe Tyr Gly Gly Cys Leu Gly Asn Gly Asn Asn Phe Lys Arg
1               5                   10                  15

Ala Lys Tyr

<210> SEQ ID NO 27
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Thr Phe Phe Tyr Gly Gly Cys Leu Gly Asn Arg Asn Asn Phe Leu Arg
1               5                   10                  15

Ala Lys Tyr

<210> SEQ ID NO 28
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Thr Phe Phe Tyr Gly Gly Cys Leu Gly Asn Arg Asn Asn Phe Lys Thr
1               5                   10                  15

Ala Lys Tyr

<210> SEQ ID NO 29
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Thr Phe Phe Tyr Gly Gly Cys Arg Gly Asn Gly Asn Asn Phe Lys Ser
1               5                   10                  15

Ala Lys Tyr

<210> SEQ ID NO 30
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 30

Thr Phe Phe Tyr Gly Gly Cys Arg Gly Lys Lys Asn Asn Phe Asp Arg
1               5                   10                  15

Glu Lys Tyr

<210> SEQ ID NO 31
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Thr Phe Phe Tyr Gly Gly Cys Arg Gly Lys Arg Asn Asn Phe Leu Arg
1               5                   10                  15

Glu Lys Glu

<210> SEQ ID NO 32
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Thr Phe Phe Tyr Gly Gly Cys Arg Gly Lys Gly Asn Asn Phe Asp Arg
1               5                   10                  15

Ala Lys Tyr

<210> SEQ ID NO 33
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Thr Phe Phe Tyr Gly Gly Ser Arg Gly Lys Gly Asn Asn Phe Asp Arg
1               5                   10                  15

Ala Lys Tyr

<210> SEQ ID NO 34
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Thr Phe Phe Tyr Gly Gly Cys Arg Gly Asn Gly Asn Asn Phe Val Thr
1               5                   10                  15

Ala Lys Tyr

<210> SEQ ID NO 35
<211> LENGTH: 19
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 35

Pro Phe Phe Tyr Gly Gly Cys Gly Gly Lys Gly Asn Asn Tyr Val Thr
1               5                   10                  15

Ala Lys Tyr

<210> SEQ ID NO 36
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Thr Phe Phe Tyr Gly Gly Cys Leu Gly Lys Gly Asn Asn Phe Leu Thr
1               5                   10                  15

Ala Lys Tyr

<210> SEQ ID NO 37
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ser Phe Phe Tyr Gly Gly Cys Leu Gly Asn Lys Asn Asn Phe Leu Thr
1               5                   10                  15

Ala Lys Tyr

<210> SEQ ID NO 38
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Thr Phe Phe Tyr Gly Gly Cys Gly Gly Asn Lys Asn Asn Phe Val Arg
1               5                   10                  15

Glu Lys Tyr

<210> SEQ ID NO 39
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Thr Phe Phe Tyr Gly Gly Cys Met Gly Asn Lys Asn Asn Phe Val Arg
1               5                   10                  15

Glu Lys Tyr

<210> SEQ ID NO 40
<211> LENGTH: 19
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 40

Thr Phe Phe Tyr Gly Gly Ser Met Gly Asn Lys Asn Phe Val Arg
1               5                   10                  15

Glu Lys Tyr

<210> SEQ ID NO 41
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Pro Phe Phe Tyr Gly Gly Cys Leu Gly Asn Arg Asn Tyr Val Arg
1               5                   10                  15

Glu Lys Tyr

<210> SEQ ID NO 42
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Thr Phe Phe Tyr Gly Gly Cys Leu Gly Asn Arg Asn Phe Val Arg
1               5                   10                  15

Glu Lys Tyr

<210> SEQ ID NO 43
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Thr Phe Phe Tyr Gly Gly Cys Leu Gly Asn Lys Asn Tyr Val Arg
1               5                   10                  15

Glu Lys Tyr

<210> SEQ ID NO 44
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Thr Phe Phe Tyr Gly Gly Cys Gly Gly Asn Gly Asn Phe Leu Thr
1               5                   10                  15

Ala Lys Tyr

<210> SEQ ID NO 45
<211> LENGTH: 19
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 45

Thr Phe Phe Tyr Gly Gly Cys Arg Gly Asn Arg Asn Asn Phe Leu Thr
1               5                   10                  15

Ala Glu Tyr

<210> SEQ ID NO 46
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Thr Phe Phe Tyr Gly Gly Cys Arg Gly Asn Gly Asn Asn Phe Lys Ser
1               5                   10                  15

Ala Glu Tyr

<210> SEQ ID NO 47
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Pro Phe Phe Tyr Gly Gly Cys Leu Gly Asn Lys Asn Asn Phe Lys Thr
1               5                   10                  15

Ala Glu Tyr

<210> SEQ ID NO 48
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Thr Phe Phe Tyr Gly Gly Cys Arg Gly Asn Arg Asn Asn Phe Lys Thr
1               5                   10                  15

Glu Glu Tyr

<210> SEQ ID NO 49
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Thr Phe Phe Tyr Gly Gly Cys Arg Gly Lys Arg Asn Asn Phe Lys Thr
1               5                   10                  15

Glu Glu Asp

<210> SEQ ID NO 50
<211> LENGTH: 19
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 50

Pro Phe Phe Tyr Gly Gly Cys Gly Gly Asn Gly Asn Asn Phe Val Arg
1               5                   10                  15

Glu Lys Tyr

<210> SEQ ID NO 51
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ser Phe Phe Tyr Gly Gly Cys Met Gly Asn Gly Asn Asn Phe Val Arg
1               5                   10                  15

Glu Lys Tyr

<210> SEQ ID NO 52
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Pro Phe Phe Tyr Gly Gly Cys Gly Gly Asn Gly Asn Asn Phe Leu Arg
1               5                   10                  15

Glu Lys Tyr

<210> SEQ ID NO 53
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Thr Phe Phe Tyr Gly Gly Cys Leu Gly Asn Gly Asn Asn Phe Val Arg
1               5                   10                  15

Glu Lys Tyr

<210> SEQ ID NO 54
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ser Phe Phe Tyr Gly Gly Cys Leu Gly Asn Gly Asn Asn Tyr Leu Arg
1               5                   10                  15

Glu Lys Tyr

<210> SEQ ID NO 55
<211> LENGTH: 19
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Thr Phe Phe Tyr Gly Gly Ser Leu Gly Asn Gly Asn Asn Phe Val Arg
1               5                   10                  15

Glu Lys Tyr

<210> SEQ ID NO 56
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Thr Phe Phe Tyr Gly Gly Cys Arg Gly Asn Gly Asn Asn Phe Val Thr
1               5                   10                  15

Ala Glu Tyr

<210> SEQ ID NO 57
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Thr Phe Phe Tyr Gly Gly Cys Leu Gly Lys Gly Asn Asn Phe Val Ser
1               5                   10                  15

Ala Glu Tyr

<210> SEQ ID NO 58
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Thr Phe Phe Tyr Gly Gly Cys Leu Gly Asn Arg Asn Asn Phe Asp Arg
1               5                   10                  15

Ala Glu Tyr

<210> SEQ ID NO 59
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Thr Phe Phe Tyr Gly Gly Cys Leu Gly Asn Arg Asn Asn Phe Leu Arg
1               5                   10                  15

Glu Glu Tyr

<210> SEQ ID NO 60
```

-continued

```
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Thr Phe Phe Tyr Gly Gly Cys Leu Gly Asn Lys Asn Asn Tyr Leu Arg
1               5                   10                  15

Glu Glu Tyr

<210> SEQ ID NO 61
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Pro Phe Phe Tyr Gly Gly Cys Gly Gly Asn Arg Asn Asn Tyr Leu Arg
1               5                   10                  15

Glu Glu Tyr

<210> SEQ ID NO 62
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Pro Phe Phe Tyr Gly Gly Ser Gly Gly Asn Arg Asn Asn Tyr Leu Arg
1               5                   10                  15

Glu Glu Tyr

<210> SEQ ID NO 63
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Met Arg Pro Asp Phe Cys Leu Glu Pro Pro Tyr Thr Gly Pro Cys Val
1               5                   10                  15

Ala Arg Ile

<210> SEQ ID NO 64
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ala Arg Ile Ile Arg Tyr Phe Tyr Asn Ala Lys Ala Gly Leu Cys Gln
1               5                   10                  15

Thr Phe Val Tyr Gly
            20
```

<210> SEQ ID NO 65
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Tyr Gly Gly Cys Arg Ala Lys Arg Asn Asn Tyr Lys Ser Ala Glu Asp
1               5                   10                  15

Cys Met Arg Thr Cys Gly
            20

<210> SEQ ID NO 66
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Pro Asp Phe Cys Leu Glu Pro Pro Tyr Thr Gly Pro Cys Val Ala Arg
1               5                   10                  15

Ile Ile Arg Tyr Phe Tyr
            20

<210> SEQ ID NO 67
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Thr Phe Phe Tyr Gly Gly Cys Arg Gly Lys Arg Asn Asn Phe Lys Thr
1               5                   10                  15

Glu Glu Tyr

<210> SEQ ID NO 68
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Lys Phe Phe Tyr Gly Gly Cys Arg Gly Lys Arg Asn Asn Phe Lys Thr
1               5                   10                  15

Glu Glu Tyr

<210> SEQ ID NO 69
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Thr Phe Tyr Tyr Gly Gly Cys Arg Gly Lys Arg Asn Asn Tyr Lys Thr
1               5                   10                  15

Glu Glu Tyr

<210> SEQ ID NO 70
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

```
Thr Phe Phe Tyr Gly Gly Ser Arg Gly Lys Arg Asn Asn Phe Lys Thr
1               5                   10                  15
Glu Glu Tyr
```

<210> SEQ ID NO 71
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

```
Cys Thr Phe Phe Tyr Gly Cys Cys Arg Gly Lys Arg Asn Asn Phe Lys
1               5                   10                  15
Thr Glu Glu Tyr
            20
```

<210> SEQ ID NO 72
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

```
Thr Phe Phe Tyr Gly Gly Cys Arg Gly Lys Arg Asn Asn Phe Lys Thr
1               5                   10                  15
Glu Glu Tyr Cys
            20
```

<210> SEQ ID NO 73
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

```
Cys Thr Phe Phe Tyr Gly Ser Cys Arg Gly Lys Arg Asn Asn Phe Lys
1               5                   10                  15
Thr Glu Glu Tyr
            20
```

<210> SEQ ID NO 74
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 74

Thr Phe Phe Tyr Gly Gly Ser Arg Gly Lys Arg Asn Asn Phe Lys Thr
1               5                   10                  15

Glu Glu Tyr Cys
            20

<210> SEQ ID NO 75
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Pro Phe Phe Tyr Gly Gly Cys Arg Gly Lys Arg Asn Asn Phe Lys Thr
1               5                   10                  15

Glu Glu Tyr

<210> SEQ ID NO 76
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Thr Phe Phe Tyr Gly Gly Cys Arg Gly Lys Arg Asn Asn Phe Lys Thr
1               5                   10                  15

Lys Glu Tyr

<210> SEQ ID NO 77
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Thr Phe Phe Tyr Gly Gly Lys Arg Gly Lys Arg Asn Asn Phe Lys Thr
1               5                   10                  15

Glu Glu Tyr

<210> SEQ ID NO 78
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Thr Phe Phe Tyr Gly Gly Cys Arg Gly Lys Arg Asn Asn Phe Lys Thr
1               5                   10                  15

Lys Arg Tyr

<210> SEQ ID NO 79
<211> LENGTH: 19
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 79

Thr Phe Phe Tyr Gly Gly Lys Arg Gly Lys Arg Asn Asn Phe Lys Thr
1               5                   10                  15

Ala Glu Tyr

<210> SEQ ID NO 80
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Thr Phe Phe Tyr Gly Gly Lys Arg Gly Lys Arg Asn Asn Phe Lys Thr
1               5                   10                  15

Ala Gly Tyr

<210> SEQ ID NO 81
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Thr Phe Phe Tyr Gly Gly Lys Arg Gly Lys Arg Asn Asn Phe Lys Arg
1               5                   10                  15

Glu Lys Tyr

<210> SEQ ID NO 82
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Thr Phe Phe Tyr Gly Gly Lys Arg Gly Lys Arg Asn Asn Phe Lys Arg
1               5                   10                  15

Ala Lys Tyr

<210> SEQ ID NO 83
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Thr Phe Phe Tyr Gly Gly Cys Leu Gly Asn Arg Asn Asn Phe Lys Thr
1               5                   10                  15

Glu Glu Tyr

<210> SEQ ID NO 84
<211> LENGTH: 19
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 84

Thr Phe Phe Tyr Gly Cys Gly Arg Gly Lys Arg Asn Asn Phe Lys Thr
1               5                   10                  15

Glu Glu Tyr

<210> SEQ ID NO 85
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Thr Phe Phe Tyr Gly Gly Arg Cys Gly Lys Arg Asn Asn Phe Lys Thr
1               5                   10                  15

Glu Glu Tyr

<210> SEQ ID NO 86
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Thr Phe Phe Tyr Gly Gly Cys Leu Gly Asn Gly Asn Asn Phe Asp Thr
1               5                   10                  15

Glu Glu Glu

<210> SEQ ID NO 87
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Thr Phe Gln Tyr Gly Gly Cys Arg Gly Lys Arg Asn Asn Phe Lys Thr
1               5                   10                  15

Glu Glu Tyr

<210> SEQ ID NO 88
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Tyr Asn Lys Glu Phe Gly Thr Phe Asn Thr Lys Gly Cys Glu Arg Gly
1               5                   10                  15

Tyr Arg Phe

<210> SEQ ID NO 89
<211> LENGTH: 19
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 89

Arg Phe Lys Tyr Gly Gly Cys Leu Gly Asn Met Asn Asn Phe Glu Thr
1               5                   10                  15

Leu Glu Glu

<210> SEQ ID NO 90
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Arg Phe Lys Tyr Gly Gly Cys Leu Gly Asn Lys Asn Asn Phe Leu Arg
1               5                   10                  15

Leu Lys Tyr

<210> SEQ ID NO 91
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Arg Phe Lys Tyr Gly Gly Cys Leu Gly Asn Lys Asn Asn Tyr Leu Arg
1               5                   10                  15

Leu Lys Tyr

<210> SEQ ID NO 92
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Lys Thr Lys Arg Lys Arg Lys Lys Gln Arg Val Lys Ile Ala Tyr Glu
1               5                   10                  15

Glu Ile Phe Lys Asn Tyr
            20

<210> SEQ ID NO 93
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Lys Thr Lys Arg Lys Arg Lys Lys Gln Arg Val Lys Ile Ala Tyr
1               5                   10                  15

<210> SEQ ID NO 94
<211> LENGTH: 17
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 94

Arg Gly Gly Arg Leu Ser Tyr Ser Arg Arg Phe Ser Thr Ser Thr Gly
1               5                   10                  15

Arg

<210> SEQ ID NO 95
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Arg Arg Leu Ser Tyr Ser Arg Arg Arg Phe
1               5                   10

<210> SEQ ID NO 96
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Arg Gln Ile Lys Ile Trp Phe Gln Asn Arg Arg Met Lys Trp Lys Lys
1               5                   10                  15

<210> SEQ ID NO 97
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Thr Phe Phe Tyr Gly Gly Ser Arg Gly Lys Arg Asn Asn Phe Lys Thr
1               5                   10                  15

Glu Glu Tyr

<210> SEQ ID NO 98
<211> LENGTH: 59
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Met Arg Pro Asp Phe Cys Leu Glu Pro Pro Tyr Thr Gly Pro Cys Val
1               5                   10                  15

Ala Arg Ile Ile Arg Tyr Phe Tyr Asn Ala Lys Ala Gly Leu Cys Gln
                20                  25                  30

Thr Phe Val Tyr Gly Gly Cys Arg Ala Lys Arg Asn Asn Phe Lys Ser
            35                  40                  45

Ala Glu Asp Cys Met Arg Thr Cys Gly Gly Ala
        50                  55
```

```
<210> SEQ ID NO 99
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Thr Phe Phe Tyr Gly Gly Cys Arg Gly Lys Arg Asn Asn Phe Lys Thr
1               5                   10                  15

Lys Glu Tyr

<210> SEQ ID NO 100
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Arg Phe Lys Tyr Gly Gly Cys Leu Gly Asn Lys Asn Asn Tyr Leu Arg
1               5                   10                  15

Leu Lys Tyr

<210> SEQ ID NO 101
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Thr Phe Phe Tyr Gly Gly Cys Arg Ala Lys Arg Asn Asn Phe Lys Arg
1               5                   10                  15

Ala Lys Tyr

<210> SEQ ID NO 102
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Asn Ala Lys Ala Gly Leu Cys Gln Thr Phe Val Tyr Gly Gly Cys Leu
1               5                   10                  15

Ala Lys Arg Asn Asn Phe Glu Ser Ala Glu Asp Cys Met Arg Thr Cys
            20                  25                  30

Gly Gly Ala
        35

<210> SEQ ID NO 103
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Tyr Gly Gly Cys Arg Ala Lys Arg Asn Asn Phe Lys Ser Ala Glu Asp
```

```
1               5                   10                  15

Cys Met Arg Thr Cys Gly Gly Ala
            20

<210> SEQ ID NO 104
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gly Leu Cys Gln Thr Phe Val Tyr Gly Gly Cys Arg Ala Lys Arg Asn
1               5                   10                  15

Asn Phe Lys Ser Ala Glu
            20

<210> SEQ ID NO 105
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Leu Cys Gln Thr Phe Val Tyr Gly Gly Cys Glu Ala Lys Arg Asn Asn
1               5                   10                  15

Phe Lys Ser Ala
            20

<210> SEQ ID NO 106

<400> SEQUENCE: 106

000

<210> SEQ ID NO 107
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (19)..(19)
<223> OTHER INFORMATION: N-term acetylated

<400> SEQUENCE: 107

Thr Phe Phe Tyr Gly Gly Ser Arg Gly Lys Arg Asn Asn Phe Lys Thr
1               5                   10                  15

Glu Glu Tyr

<210> SEQ ID NO 108
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Arg Phe Phe Tyr Gly Gly Ser Arg Gly Lys Arg Asn Asn Phe Lys Thr
1               5                   10                  15
```

```
<210> SEQ ID NO 109
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Arg Phe Phe Tyr Gly Gly Ser Arg Gly Lys Arg Asn Asn Phe Lys Thr
1               5                   10                  15

Glu Glu Tyr

<210> SEQ ID NO 110
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Arg Phe Phe Tyr Gly Gly Ser Arg Gly Lys Arg Asn Asn Phe Arg Thr
1               5                   10                  15

Glu Glu Tyr

<210> SEQ ID NO 111
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Thr Phe Phe Tyr Gly Gly Ser Arg Gly Lys Arg Asn Asn Phe Arg Thr
1               5                   10                  15

Glu Glu Tyr

<210> SEQ ID NO 112
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Thr Phe Phe Tyr Gly Gly Ser Arg Gly Arg Arg Asn Asn Phe Arg Thr
1               5                   10                  15

Glu Glu Tyr

<210> SEQ ID NO 113
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Cys Thr Phe Phe Tyr Gly Gly Ser Arg Gly Lys Arg Asn Asn Phe Lys
```

```
1               5                   10                  15

Thr Glu Glu Tyr
            20

<210> SEQ ID NO 114
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Thr Phe Phe Tyr Gly Gly Ser Arg Gly Lys Arg Asn Asn Phe Lys Thr
1               5                   10                  15

Glu Glu Tyr Cys
            20

<210> SEQ ID NO 115
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Cys Thr Phe Phe Tyr Gly Gly Ser Arg Gly Arg Arg Asn Asn Phe Arg
1               5                   10                  15

Thr Glu Glu Tyr
            20

<210> SEQ ID NO 116
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Thr Phe Phe Tyr Gly Gly Ser Arg Gly Arg Arg Asn Asn Phe Arg Thr
1               5                   10                  15

Glu Glu Tyr Cys
            20

<210> SEQ ID NO 117
<211> LENGTH: 20
<212> TYPE: PRT
<213> ORGANISM: Homo sapiens

<400> SEQUENCE: 117

Arg Arg His Gly Thr Pro Arg Arg Leu Leu Tyr Cys Gln Arg Ser Leu
1               5                   10                  15

Leu Asp Lys Val
            20

<210> SEQ ID NO 118
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 118

Arg Arg His Gly Thr Pro Arg Arg Leu Leu Phe Cys Gln Arg Ser Leu
1               5                   10                  15

Leu Asp Lys Val
            20

<210> SEQ ID NO 119
<211> LENGTH: 16
<212> TYPE: PRT
<213> ORGANISM: Unknown
<220> FEATURE:
<223> OTHER INFORMATION: Description of Unknown: Antennapedia peptide

<400> SEQUENCE: 119

Arg Gln Ile Lys Ile Trp Phe Gln Asn Arg Arg Met Lys Trp Lys Lys
1               5                   10                  15

<210> SEQ ID NO 120
<211> LENGTH: 17
<212> TYPE: PRT
<213> ORGANISM: Unknown
<220> FEATURE:
<223> OTHER INFORMATION: Description of Unknown: Antennapedia leader
      peptide

<400> SEQUENCE: 120

Lys Lys Trp Lys Met Arg Arg Asn Gln Phe Trp Val Lys Val Gln Arg
1               5                   10                  15

Gly

<210> SEQ ID NO 121
<211> LENGTH: 16
<212> TYPE: PRT
<213> ORGANISM: Unknown
<220> FEATURE:
<223> OTHER INFORMATION: Description of Unknown: Antennapedia peptide
      amide
<220> FEATURE:
<221> NAME/KEY: MISC_FEATURE
<222> LOCATION: (16)..(16)
<223> OTHER INFORMATION: C-term amidated

<400> SEQUENCE: 121

Arg Gln Ile Lys Ile Trp Phe Gln Asn Arg Arg Met Lys Trp Lys Lys
1               5                   10                  15

<210> SEQ ID NO 122
<211> LENGTH: 17
<212> TYPE: PRT
<213> ORGANISM: Unknown
<220> FEATURE:
<223> OTHER INFORMATION: Description of Unknown: Cys(Npys)-Antennapedia
      peptide amide
<220> FEATURE:
<221> NAME/KEY: MOD_RES
<222> LOCATION: (1)..(1)
<223> OTHER INFORMATION: Cys(3-nitro-2-pyridinesulfenyl)
<220> FEATURE:
<221> NAME/KEY: MISC_FEATURE
<222> LOCATION: (17)..(17)
<223> OTHER INFORMATION: C-term amidated

<400> SEQUENCE: 122

Cys Arg Gln Ile Lys Ile Trp Phe Gln Asn Arg Arg Met Lys Trp Lys
1               5                   10                  15

Lys
```

<210> SEQ ID NO 123
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Tyr Gly Arg Arg Ala Arg Arg Arg Arg Arg Arg
1               5                   10

<210> SEQ ID NO 124
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Tyr Gly Arg Arg Ala Arg Arg Arg Ala Arg Arg
1               5                   10

<210> SEQ ID NO 125
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Tyr Gly Arg Arg Ala Arg Arg Ala Ala Arg Arg
1               5                   10

<210> SEQ ID NO 126
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Tyr Lys Arg Lys Ala Arg Arg Ala Ala Arg Arg
1               5                   10

<210> SEQ ID NO 127
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Tyr Ala Arg Lys Ala Arg Arg Ala Ala Arg Arg
1               5                   10

<210> SEQ ID NO 128
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 128

Tyr Lys Arg Ala Ala Arg Arg Ala Ala Arg Arg
1               5                   10

<210> SEQ ID NO 129
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Tyr Glu Arg Glu Ala Arg Arg Ala Ala Arg Arg
1               5                   10

<210> SEQ ID NO 130
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Tyr Ala Arg Glu Ala Arg Arg Ala Ala Arg Arg
1               5                   10

<210> SEQ ID NO 131
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Tyr Gly Arg Ala Ala Arg Arg Ala Ala Arg Arg
1               5                   10

<210> SEQ ID NO 132
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Tyr Arg Arg Ala Ala Arg Arg Ala Ala Arg Ala
1               5                   10

<210> SEQ ID NO 133
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Tyr Pro Arg Ala Ala Arg Arg Ala Ala Arg Arg
1               5                   10

<210> SEQ ID NO 134
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 134

Pro Ala Arg Ala Ala Arg Arg Ala Ala Arg Arg
1               5                   10

<210> SEQ ID NO 135
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Tyr Gly Arg Arg Arg Arg Arg Arg Arg Arg Arg
1               5                   10

<210> SEQ ID NO 136
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Tyr Arg Arg Arg Arg Arg Arg Arg Arg Arg Arg
1               5                   10

<210> SEQ ID NO 137
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Arg Arg Arg Arg Arg Arg Arg Arg Arg
1               5

<210> SEQ ID NO 138
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys(3-nitro-2-pyridinesulfenyl)

<400> SEQUENCE: 138

Cys Arg Arg Arg Arg Arg Arg Arg Arg Arg
1               5                   10

<210> SEQ ID NO 139
<211> LENGTH: 17
<212> TYPE: PRT
<213> ORGANISM: Unknown
<220> FEATURE:
<223> OTHER INFORMATION: Description of Unknown: [Cys58]105Y Cell
      penetrating peptide
```

```
<400> SEQUENCE: 139

Cys Ser Ile Pro Pro Glu Val Lys Phe Asn Lys Pro Phe Val Tyr Leu
1               5                   10                  15

Ile

<210> SEQ ID NO 140
<211> LENGTH: 16
<212> TYPE: PRT
<213> ORGANISM: Unknown
<220> FEATURE:
<223> OTHER INFORMATION: Description of Unknown: 105Y peptide

<400> SEQUENCE: 140

Ser Ile Pro Pro Glu Val Lys Phe Asn Lys Pro Phe Val Tyr Leu Ile
1               5                   10                  15

<210> SEQ ID NO 141
<211> LENGTH: 21
<212> TYPE: PRT
<213> ORGANISM: Unknown
<220> FEATURE:
<223> OTHER INFORMATION: Description of Unknown: Buforin peptide

<400> SEQUENCE: 141

Thr Arg Ser Ser Arg Ala Gly Leu Gln Phe Pro Val Gly Arg Val His
1               5                   10                  15

Arg Leu Leu Arg Lys
            20

<210> SEQ ID NO 142
<211> LENGTH: 41
<212> TYPE: PRT
<213> ORGANISM: Rabies virus

<400> SEQUENCE: 142

Tyr Thr Ile Trp Met Pro Glu Asn Pro Arg Pro Gly Thr Pro Cys Asp
1               5                   10                  15

Ile Phe Thr Asn Ser Arg Gly Lys Arg Ala Ser Asn Gly Gly Gly Gly
            20                  25                  30

Arg Arg Arg Arg Arg Arg Arg Arg
            35                  40

<210> SEQ ID NO 143
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys(3-nitro-2-pyridinesulfenyl)
<220> FEATURE:
<221> NAME/KEY: MISC_FEATURE
<222> LOCATION: (12)..(12)
<223> OTHER INFORMATION: C-term amidated

<400> SEQUENCE: 143

Cys Tyr Gly Arg Lys Lys Arg Arg Gln Arg Arg Arg
1               5                   10

<210> SEQ ID NO 144
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (12)..(12)
<223> OTHER INFORMATION: C-term amidated

<400> SEQUENCE: 144

Cys Tyr Gly Arg Lys Lys Arg Arg Gln Arg Arg Arg
1               5                   10

<210> SEQ ID NO 145
<211> LENGTH: 15
<212> TYPE: PRT
<213> ORGANISM: Unknown
<220> FEATURE:
<223> OTHER INFORMATION: Description of Unknown: Lipid membrane
      translocating peptide

<400> SEQUENCE: 145

Lys Lys Ala Ala Ala Val Leu Leu Pro Val Leu Leu Ala Ala Pro
1               5                   10                  15

<210> SEQ ID NO 146
<211> LENGTH: 14
<212> TYPE: PRT
<213> ORGANISM: Unknown
<220> FEATURE:
<223> OTHER INFORMATION: Description of Unknown: Mastoparan peptide
<220> FEATURE:
<221> NAME/KEY: MISC_FEATURE
<222> LOCATION: (14)..(14)
<223> OTHER INFORMATION: C-term amidated

<400> SEQUENCE: 146

Ile Asn Leu Lys Ala Leu Ala Ala Leu Ala Lys Lys Ile Leu
1               5                   10

<210> SEQ ID NO 147
<211> LENGTH: 14
<212> TYPE: PRT
<213> ORGANISM: Unknown
<220> FEATURE:
<223> OTHER INFORMATION: Description of Unknown: Mastoparan 7 peptide
<220> FEATURE:
<221> NAME/KEY: MISC_FEATURE
<222> LOCATION: (14)..(14)
<223> OTHER INFORMATION: C-term amidated

<400> SEQUENCE: 147

Ile Asn Leu Lys Ala Leu Ala Ala Leu Ala Lys Ala Leu Leu
1               5                   10

<210> SEQ ID NO 148
<211> LENGTH: 14
<212> TYPE: PRT
<213> ORGANISM: Unknown
<220> FEATURE:
<223> OTHER INFORMATION: Description of Unknown: Mastoparan X peptide
<220> FEATURE:
<221> NAME/KEY: MISC_FEATURE
<222> LOCATION: (14)..(14)
<223> OTHER INFORMATION: C-term amidated

<400> SEQUENCE: 148

Ile Asn Trp Lys Gly Ile Ala Ala Met Ala Lys Lys Leu Leu
1               5                   10
```

```
<210> SEQ ID NO 149
<211> LENGTH: 13
<212> TYPE: PRT
<213> ORGANISM: Unknown
<220> FEATURE:
<223> OTHER INFORMATION: Description of Unknown: MEK1 derived peptide
      inhibitor 1

<400> SEQUENCE: 149

Met Pro Lys Lys Lys Pro Thr Pro Ile Gln Leu Asn Pro
1               5                   10

<210> SEQ ID NO 150
<211> LENGTH: 13
<212> TYPE: PRT
<213> ORGANISM: Unknown
<220> FEATURE:
<223> OTHER INFORMATION: Description of Unknown: Myristoyl-MEK1 derived
      peptide inhibitor 1
<220> FEATURE:
<221> NAME/KEY: MOD_RES
<222> LOCATION: (1)..(1)
<223> OTHER INFORMATION: Myristoyl-Met

<400> SEQUENCE: 150

Met Pro Lys Lys Lys Pro Thr Pro Ile Gln Leu Asn Pro
1               5                   10

<210> SEQ ID NO 151
<211> LENGTH: 13
<212> TYPE: PRT
<213> ORGANISM: Unknown
<220> FEATURE:
<223> OTHER INFORMATION: Description of Unknown: Stearyl-MEK-1 derived
      peptide inhibitor 1 amide
<220> FEATURE:
<221> NAME/KEY: MOD_RES
<222> LOCATION: (1)..(1)
<223> OTHER INFORMATION: Stearyl-Met
<220> FEATURE:
<221> NAME/KEY: MISC_FEATURE
<222> LOCATION: (13)..(13)
<223> OTHER INFORMATION: C-term amidated

<400> SEQUENCE: 151

Met Pro Lys Lys Lys Pro Thr Pro Ile Gln Leu Asn Pro
1               5                   10

<210> SEQ ID NO 152
<211> LENGTH: 16
<212> TYPE: PRT
<213> ORGANISM: Unknown
<220> FEATURE:
<223> OTHER INFORMATION: Description of Unknown: Membrane-permeable
      sequence

<400> SEQUENCE: 152

Ala Ala Val Ala Leu Leu Pro Ala Val Leu Leu Ala Leu Leu Ala Lys
1               5                   10                  15

<210> SEQ ID NO 153
<211> LENGTH: 27
<212> TYPE: PRT
<213> ORGANISM: Unknown
<220> FEATURE:
<223> OTHER INFORMATION: Description of Unknown: HIV related MPG

<400> SEQUENCE: 153

Gly Ala Leu Phe Leu Gly Phe Leu Gly Ala Ala Gly Ser Thr Met Gly
```

```
                1               5                  10                  15
Ala Trp Ser Gln Pro Lys Ser Lys Arg Lys Val
                20                  25
```

<210> SEQ ID NO 154
<211> LENGTH: 6
<212> TYPE: PRT
<213> ORGANISM: Unknown
<220> FEATURE:
<223> OTHER INFORMATION: Description of Unknown: NGR peptide
<220> FEATURE:
<221> NAME/KEY: misc_feature
<222> LOCATION: (1)..(5)
<223> OTHER INFORMATION: Disulfide bridge

<400> SEQUENCE: 154

```
Cys Asn Gly Arg Cys Gly
1               5
```

<210> SEQ ID NO 155
<211> LENGTH: 11
<212> TYPE: PRT
<213> ORGANISM: Unknown
<220> FEATURE:
<223> OTHER INFORMATION: Description of Unknown: NGR peptide 2
<220> FEATURE:
<221> NAME/KEY: misc_feature
<222> LOCATION: (1)..(5)
<223> OTHER INFORMATION: Disulfide bridge

<400> SEQUENCE: 155

```
Cys Asn Gly Arg Cys Gly Gly Leu Val Thr Thr
1               5                  10
```

<210> SEQ ID NO 156
<211> LENGTH: 5
<212> TYPE: PRT
<213> ORGANISM: Unknown
<220> FEATURE:
<223> OTHER INFORMATION: Description of Unknown: NGR peptide 3
<220> FEATURE:
<221> NAME/KEY: misc_feature
<222> LOCATION: (1)..(5)
<223> OTHER INFORMATION: Disulfide bridge
<220> FEATURE:
<221> NAME/KEY: MISC_FEATURE
<222> LOCATION: (5)..(5)
<223> OTHER INFORMATION: C-term amidated

<400> SEQUENCE: 156

```
Cys Asn Gly Arg Cys
1               5
```

<210> SEQ ID NO 157
<211> LENGTH: 21
<212> TYPE: PRT
<213> ORGANISM: Unknown
<220> FEATURE:
<223> OTHER INFORMATION: Description of Unknown: Pep-1 peptide

<400> SEQUENCE: 157

```
Lys Glu Thr Trp Trp Glu Thr Trp Trp Thr Glu Trp Ser Gln Pro Lys
1               5                  10                  15

Lys Lys Arg Lys Val
                20
```

<210> SEQ ID NO 158
<211> LENGTH: 19

```
<212> TYPE: PRT
<213> ORGANISM: Unknown
<220> FEATURE:
<223> OTHER INFORMATION: Description of Unknown: SynB1 peptide

<400> SEQUENCE: 158

Arg Gly Gly Arg Leu Ser Tyr Ser Arg Arg Arg Phe Ser Thr Ser Thr
1               5                   10                  15

Gly Arg Ala

<210> SEQ ID NO 159
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Biotin-Tyr

<400> SEQUENCE: 159

Tyr Gly Arg Lys Lys Arg Arg Gln Arg Arg Arg
1               5                   10

<210> SEQ ID NO 160
<211> LENGTH: 11
<212> TYPE: PRT
<213> ORGANISM: Human immunodeficiency virus 1

<400> SEQUENCE: 160

Tyr Gly Arg Lys Lys Arg Arg Gln Arg Arg Arg
1               5                   10

<210> SEQ ID NO 161
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Cys(3-nitro-2-pyridinesulfenyl)
<220> FEATURE:
<221> NAME/KEY: MISC_FEATURE
<222> LOCATION: (15)..(15)
<223> OTHER INFORMATION: C-term amidated

<400> SEQUENCE: 161

Tyr Gly Arg Lys Lys Arg Arg Gln Arg Arg Arg Gly Gly Gly Cys
1               5                   10                  15

<210> SEQ ID NO 162
<211> LENGTH: 10
<212> TYPE: PRT
<213> ORGANISM: Human immunodeficiency virus 1

<400> SEQUENCE: 162

Gly Arg Lys Lys Arg Arg Gln Arg Arg Arg
1               5                   10

<210> SEQ ID NO 163
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 163

Cys Gly Arg Lys Lys Arg Arg Gln Arg Arg
1               5                   10

<210> SEQ ID NO 164
<211> LENGTH: 11
<212> TYPE: PRT
<213> ORGANISM: Unknown
<220> FEATURE:
<223> OTHER INFORMATION: Description of Unknown: Transdermal peptide

<400> SEQUENCE: 164

Ala Cys Ser Ser Ser Pro Ser Lys His Cys Gly
1               5                   10

<210> SEQ ID NO 165
<211> LENGTH: 27
<212> TYPE: PRT
<213> ORGANISM: Unknown
<220> FEATURE:
<223> OTHER INFORMATION: Description of Unknown: Transportan peptide

<400> SEQUENCE: 165

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 166
<211> LENGTH: 21
<212> TYPE: PRT
<213> ORGANISM: Unknown
<220> FEATURE:
<223> OTHER INFORMATION: Description of Unknown: Transportan 10 peptide
<220> FEATURE:
<221> NAME/KEY: MISC_FEATURE
<222> LOCATION: (21)..(21)
<223> OTHER INFORMATION: C-term amidated

<400> SEQUENCE: 166

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 167
<211> LENGTH: 29
<212> TYPE: PRT
<213> ORGANISM: Rabies virus

<400> SEQUENCE: 167

Tyr Thr Ile Trp Met Pro Glu Asn Pro Arg Pro Gly Thr Pro Cys Asp
1               5                   10                  15

Ile Phe Thr Asn Ser Arg Gly Lys Arg Ala Ser Asn Gly
            20                  25

<210> SEQ ID NO 168
<211> LENGTH: 39
<212> TYPE: PRT
<213> ORGANISM: Neisseria gonorrhoeae

<400> SEQUENCE: 168
```

```
Cys Ser Gln Glu Pro Ala Ala Pro Ala Glu Ala Thr Pro Ala Gly
1               5                   10                  15

Glu Ala Pro Ala Ser Glu Ala Pro Ala Glu Ala Ala Pro Ala Asp
                20                  25                  30

Ala Ala Glu Ala Pro Ala Ala
            35

<210> SEQ ID NO 169
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Gly Gly Gly Gly Ser
1               5

<210> SEQ ID NO 170
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Gly Gly Gly Gly Ser Gly Gly Gly Gly Ser
1               5                   10

<210> SEQ ID NO 171
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Gly Gly Gly Gly Ser Gly Gly Gly Gly Ser Gly Gly Gly Gly Ser
1               5                   10                  15

<210> SEQ ID NO 172
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Gly Gly Gly Gly Ser Gly Gly Gly Gly Ser Gly Gly Gly Gly Ser Gly
1               5                   10                  15

Gly Gly Gly Ser
            20

<210> SEQ ID NO 173
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173
```

-continued

Gly Gly Gly Gly Ser Gly Gly Gly Ser Gly Gly Gly Ser Gly
1               5                  10                 15

Gly Gly Gly Ser Gly Gly Gly Ser
            20                  25

<210> SEQ ID NO 174
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Gly Gly Gly Gly Ser Gly Gly Gly Ser Gly Gly Gly Ser Gly
1               5                  10                 15

Gly Gly Gly Ser Gly Gly Gly Ser Gly Gly Gly Ser
            20                  25                  30

<210> SEQ ID NO 175
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Ser Ser Ser Ser Gly
1               5

<210> SEQ ID NO 176
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Biotin-Amino hexanoic acid

<400> SEQUENCE: 176

Xaa Arg Gln Ile Lys Ile Trp Phe Gln Asn Arg Arg Met Lys Trp Lys
1               5                  10                  15

Lys Arg Arg His Gly Thr Pro Arg Arg Leu Leu Phe Cys Gln Arg Ser
            20                  25                  30

Leu Leu Asp Lys Val
        35

<210> SEQ ID NO 177
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Biotin-Amino hexanoic acid

<400> SEQUENCE: 177

Xaa Arg Gln Ile Lys Ile Trp Phe Gln Asn Arg Arg Met Lys Trp Lys
1               5                  10                  15

```
Lys Thr Leu Arg Gln Arg Arg Cys Leu Pro His Phe Asp Ser Gly Leu
            20                  25                  30

Arg Lys Val Arg Leu
        35

<210> SEQ ID NO 178
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Thr Phe Phe Tyr Gly Gly Ser Arg Gly Lys Arg Asn Asn Phe Lys Thr
1               5                   10                  15

Glu Glu Tyr Arg Arg His Gly Thr Pro Arg Arg Leu Leu Phe Cys Gln
            20                  25                  30

Arg Ser Leu Leu Asp Lys Val
        35

<210> SEQ ID NO 179
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Ala Ala Glu Ala Pro
1               5
```